(12) United States Patent
Chang

(10) Patent No.: US 9,844,583 B2
(45) Date of Patent: Dec. 19, 2017

(54) ROLE OF A CLUSTER OF LONG NONCODING RNA TRANSCRIPTS IN PROTECTING THE HEART FROM PATHOLOGICAL HYPERTROPHY

(71) Applicant: Indiana University Research & Technology Corporation, Indianapolis, IN (US)

(72) Inventor: Ching-Pin Chang, Indianapolis, IN (US)

(73) Assignee: Indiana University Research and Technology Corp., Indianapolis, IN (US)

(*) Notice: Subject to any disclaimer, the term of this patent is extended or adjusted under 35 U.S.C. 154(b) by 0 days.

(21) Appl. No.: 14/884,827

(22) Filed: Oct. 16, 2015

(65) Prior Publication Data
US 2016/0114004 A1 Apr. 28, 2016

Related U.S. Application Data

(60) Provisional application No. 62/068,041, filed on Oct. 24, 2014.

(51) Int. Cl.
| | |
|---|---|
| *A01K 67/00* | (2006.01) |
| *C07H 21/04* | (2006.01) |
| *A61K 31/70* | (2006.01) |
| *A61K 38/43* | (2006.01) |
| *A61K 9/00* | (2006.01) |
| *C07K 14/47* | (2006.01) |
| *C12N 9/14* | (2006.01) |
| *A01K 67/027* | (2006.01) |
| *C07K 1/00* | (2006.01) |
| *A61K 48/00* | (2006.01) |

(52) U.S. Cl.
CPC .......... *A61K 38/43* (2013.01); *A01K 67/0275* (2013.01); *A61K 9/0019* (2013.01); *C07K 14/4716* (2013.01); *C12N 9/14* (2013.01); *C12Y 306/04* (2013.01); *A01K 2217/052* (2013.01); *A01K 2217/203* (2013.01); *A01K 2217/206* (2013.01); *A01K 2227/105* (2013.01); *A01K 2267/0375* (2013.01); *A61K 48/00* (2013.01); *C12N 2310/14* (2013.01)

(58) Field of Classification Search
CPC ...... A61K 38/43; A61K 48/00; A61K 9/0019; A01K 67/0275; A01K 2217/052; A01K 2217/203; C12N 2310/14
See application file for complete search history.

(56) References Cited

U.S. PATENT DOCUMENTS

| | | |
|---|---|---|
| 2013/0109738 A1 | 5/2013 | Chang et al. |
| 2014/0105828 A1 | 4/2014 | Yang |
| 2016/0153000 A1* | 6/2016 | Glorioso ............... A61K 35/763 514/44 R |

OTHER PUBLICATIONS

Pei Han et al. Long non-coding RNA and chromatin remodeling. RNA Biology 12:1094-1098, 2015.*
Lingjie Li et al. Physiological roles of long noncoding RNAs: Insights from knockout mice. Trends Cell Biol. 24:594-602, 2014.*
Hahn, M. A., Wu, X., Li, A. X., Hahn, T. & Pfeifer, G. P. Relationship between gene body DNA methylation and intragenic H3K9me3 and H3K36me3 chromatin marks. PLoS ONE 6, e18844 (2011).
Mikkelsen, T. S. et al. Genome-wide maps of chromatin state in pluripotent and lineage-committed cells. Nature 448, 553-560 (2007).
Musselman, C. A. et al. Molecular basis for H3K36me3 recognition by the Tudor domain of PHF1. Nature Struct. Mol. Biol. 19, 1266-1272 (2012).
Liu, R. et al. Regulation of CSF1 promoter by the SWI/SNF-like BAF complex. Cell 106, 309-318 (2001).
Muchardt, C. & Yaniv, M. A human homologue of *Saccharomyces cerevisiae* SNF2/ SWI2 and *Drosophila* brm genes potentiates transcriptional activation by the glucocorticoid receptor. EMBO J. 12, 4279-4290 (1993).
Szabó, G. et al. Poly(ADP-ribose) polymerase inhibition reduces reperfusion injury after heart transplantation. Circ. Res. 90, 100-106 (2002).
Hesselberth, J. R. et al. Global mapping of protein—DNA interactions in vivo by digital genomic footprinting. Nature Methods 6, 283-289 (2009).
Gupta, M. P. Factors controlling cardiac myosin-isoform shift during hypertrophy and heart failure. J. Mol. Cell. Cardiol. 13, 388-403 (2007).
Clapier, C. R. & Cairns, B. R. The biology of chromatin remodeling complexes. Annu. Rev. Biochem. 78, 273-304 (2009).
Jankowsky, E. & Fairman, M. E. RNA helicases—one fold for many functions. Curr. Opin. Struct. Biol. 17, 316-324 (2007).
Mallam, A. L., Del Campo, M., Gilman, B., Sidote, D. J. & Lambowitz, A. M. Structural basis for RNA-duplex recognition and unwinding by the DEAD-box helicase Mss116p. Nature 490, 121-125 (2012).
Dürr, H., Korner, C., Muller, M., Hickmann, V. & Hopfner, K. P. X-ray structures of the Sulfolobus solfataricus SWI2/SNF2 ATPase core and its complex with DNA. Cell 121, 363-373 (2005).
Feng, Y. et al. Histone H4 acetylation differentially modulates arginine methylation by an in cis mechanism. J. Biol. Chem. 286, 20323-20334 (2011).
Zuker, M. On finding all suboptimal foldings of an RNA molecule. Science 244, 48-52 (1989).
Wu, B. et al. Inducible cardiomyocyte-specific gene disruption directed by the rat Tnnt2 promoter in the mouse. Genesis 48, 63-72 (2010).

(Continued)

*Primary Examiner* — Quang Nguyen
(74) *Attorney, Agent, or Firm* — Miles & Stockbridge P.C.; Ajay A. Jagtiana

(57) ABSTRACT

Nucleic acids encoding modified myosin heavy-chain-associated RNA transcripts are provided. The modified myosin heavy-chain-associated RNA transcripts belongs to a cluster of long noncoding RNAs (lncRNA) and bind to chromatin remodeler Brg1 to inhibit Brg1's genomic targeting and gene regulation function. The modified myosin heavy-chain-associated RNA transcripts expressed in an individual inhibit Brg1's gene regulation function and protect the heart of the individual from myopathy and failure. One of the modified heavy-chain-associated RNAs is a 400 base pair fragment segmented from a natural 779 base pair sequence of Mhrt (Mhrt779) and has the same cardioprotective effects as the Mhrt779.

32 Claims, 22 Drawing Sheets

(56) References Cited

OTHER PUBLICATIONS

Wei, K., Kuhnert, F. & Kuo, C. J. Recombinant adenovirus as a methodology for exploration of physiologic functions of growth factor pathways. J. Mol. Med. (Berl.) 86, 161-169 (2008).
Kuhnert, F. et al. Essential regulation of CNS angiogenesis by the orphan G protein—coupled receptor GPR124. Science 330, 985-989 (2010).
Xiong, Y. et al. Brg1 governs a positive feedback circuit in the hair follicle for tissue regeneration and repair. Dev. Cell 25, 169-181 (2013).
Langmead, B. & Salzberg, S. L Fast gapped-read alignment with Bowtie 2. Nature Methods 9, 357-359 (2012).
Li, H. et al. The Sequence Alignment/Map format and SAMtools. Bioinformatics 25, 2078-2079 (2009).
Quinlan, A. R. & Hall, I. M. BEDTools: a flexible suite of utilities for comparing genomic features. Bioinformatics 26, 841-842 (2010).
Trapnell, C. et al. Differential gene and transcript expression analysis of RNA-seq experiments with TopHat and Cufflinks. Nature Protocols 7, 562-578 (2012).
Khavari, P. A., Peterson, C. L., Tamkun, J. W., Mendel, D. B. & Crabtree, G. R. BRG1 contains a conserved domain of the SWI2/SNF2 family necessary for normal mitotic growth and transcription. Nature 366, 170-174 (1993).
Grote, P. et al. The tissue-specific lncRNA Fendrr is an essential regulator of heart and body wall development in the mouse. Dev. Cell 24, 206-214 (2013).
Klattenhoff, C. A. et al. Braveheart, a long noncoding RNA required for cardiovascular lineage commitment. Cell 152, 570-583 (2013).
van der Vlag, J., den Blaauwen, J. L., Sewalt, R. G., van Driel, R. & Otte, A. P. Transcriptional repression mediated by polycomb group proteins and other chromatin-associated repressors is selectively blocked by insulators. J. Biol. Chem. 275, 697-704 (2000).
Sengoku, T., Nureki, O., Nakamura, A., Kobayashi, S. & Yokoyama, S. Structural basis for RNA unwinding by the DEAD-box protein *Drosophila* Vasa. Cell 125, 287-300 (2006).
Thomä, N. H. et al. Structure of the SWI2/SNF2 chromatin-remodeling domain of eukaryotic Rad54. Nature Struct. Mol. Biol. 12, 350-356 (2005).
Hauk, G., McKnight, J. N., Nodelman, I. M. & Bowman, G. D. The chromodomains of the Chd1 chromatin remodeler regulate DNA access to the ATPase motor. Mol. Cell 39, 711-723 (2010).
Zuker, M. & Stiegler, P. Optimal computer folding of large RNA sequences using thermodynamics and auxiliary information. Nucleic Acids Res. 9, 133-148 (1981).
Gruber, A. R., Lorenz, R., Bernhart, S. H., Neubock, R. & Hofacker, I. L. The Vienna RNA websuite. Nucleic Acids Res. 36, W70-W74 (2008).
Wan, Y., Kertesz, M., Spitale, R. C., Segal, E. & Chang, H. Y. Understanding the transcriptome through RNA structure. Nature Rev. Genet. 12, 641-655 (2011).
Fu, X. M., Yao, Y. J., Yang, Z., Xiang, L. & Gao, J. [Alteration and its significance to expression of aquaporin-4 in cultured neonatal rat astrocytes in the model of hypoxic damage.] Sichuan Da Xue Xue Bao Yi Xue Ban 36, 641-644 (2005).
Yang, J. et al. C-reactive protein augments hypoxia-induced apoptosis through mitochondrion-dependent pathway in cardiac myocytes. Mol. Cell. Biochem. 310, 215-226 (2008).
Han et al., "A long noncoding RNA protects the heart from pathological hypertrophy", Nature, vol. 514, Issue 7520, pp. 102-106 (2014).
Liu et al., "An Epigenetic "LINK(RNA)" to Pathological Cardiac Hypertrophy", Cell Metabolism 20, pp. 555-557 (2014).
van Rooij, E. et al. Control of stress-dependent cardiac growth and gene expression by a microRNA. Science 316, 575-579 (2007).
Herron, T. J. & McDonald, K. S. Small amounts of α-myosin heavy chain isoform expression significantly increase power output of rat cardiac myocyte fragments. Circ. Res. 90, 1150-1152 (2002).
Krenz, M. & Robbins, J. Impact of b-myosin heavy chain expression on cardiac function during stress. J. Am. Coll. Cardiol. 44, 2390-2397 (2004).
James, J. et al. Forced expression of α-myosin heavy chain in the rabbit ventricle results in cardioprotection under cardiomyopathic conditions. Circulation 111, 2339-2346 (2005).
Miyata, S., Minobe, W., Bristow, M. R. & Leinwand, L. A. Myosin heavy chain isoform expression in the failing and nonfailing human heart. Circ. Res. 86, 386-390 (2000).
Abraham, W. T. et al. Coordinate changes in myosin heavy chain isoform gene expression are selectively associated with alterations in dilated cardiomyopathy phenotype. Mol. Med. 8, 750-760 (2002).
Lowes, B. D. et al. Myocardial gene expression in dilated cardiomyopathy treated with b-blocking agents. N. Engl. J. Med. 346, 1357-1365 (2002).
Blaxall, B. C., Tschannen-Moran, B. M., Milano, C. A. & Koch, W. J. Differential gene expression and genomic patient stratification following left ventricular assist device support J. Am. Coll. Cardiol. 41, 1096-1106 (2003).
Geisterfer-Lowrance, A. A. et al. A mouse model of familial hypertrophic cardiomyopathy. Science 272, 731-734 (1996).
Schmitt, J. P. et al. Cardiac myosin missense mutations cause dilated cardiomyopathy in mouse models and depress molecular motor function. Proc. Natl Acad. Sci. USA 103, 14525-14530 (2006).
Lowes, B. D. et al. Changes in gene expression in the intact human heart. Downregulation of α-myosin heavy chain in hypertrophied, failing ventricular myocardium. J. Clin. Invest. 100, 2315-2324 (1997).
McKinsey, T. A. & Olson, E. N. Toward transcriptional therapies for the failing heart: chemical screens to modulate genes. J. Clin. Invest. 115, 538-546 (2005).
Ho, L. & Crabtree, G. R. Chromatin remodelling during development. Nature 463, 474-484 (2010).
Bultman, S. et al. A Brg1 null mutation in the mouse reveals functional differences among mammalian SWI/SNF complexes. Mol. Cell 6, 1287-1295 (2000).
Backs, J. & Olson, E. N. Control of cardiac growth by histone acetylation/ deacetylation. Circ. Res. 98, 15-24 (2006).
Schreiber, V., Dantzer, F., Ame, J. C. & de Murcia, G. Poly(ADP-ribose): novel functions for an old molecule. Nature Rev. Mol. Cell Biol. 7, 517-528 (2006).
Bartha, E. et al. PARP inhibition delays transition of hypertensive cardiopathy to heart failure in spontaneously hypertensive rats. Cardiovasc. Res. 83, 501-510 (2009).
Kong, Y. et al. Suppression of class I and II histone deacetylases blunts pressure—overload cardiac hypertrophy. Circulation 113, 2579-2588 (2006).
Antos, C. L et al. Dose-dependent blockade to cardiomyocyte hypertrophy by histone deacetylase inhibitors. J. Biol. Chem. 278, 28930-28937 (2003).
Trivedi, C. M. et al. Hdac2 regulates the cardiac hypertrophic response by modulating Gsk3 beta activity. Nature Med. 13, 324-331 (2007).
Kee, H. J. et al. Inhibition of histone deacetylation blocks cardiac hypertrophy induced by angiotensin II infusion and aortic banding. Circulation 113, 51-59 (2006).
Pillai, J. B. et al. Poly(ADP-ribose) polymerase-1-deficient mice are protected from angiotensin II-induced cardiac hypertrophy. Am. J. Physiol. Heart Circ. Physiol. 291, H1545-H1553 (2006).
Stankunas, K. et al. Endocardial Brg1 represses ADAMTS1 to maintain the microenvironment for myocardial morphogenesis. Dev. Cell 14, 298-311 (2008).
Sumi-Ichinose, C., Ichinose, H., Metzger, D. & Chambon, P. SNF2b-BRG1 is essential for the viability of F9 murine embryonal carcinoma cells. Mol. Cell. Biol. 17, 5976-5986 (1997).
Chen, H. et al. BMP10 is essential for maintaining cardiac growth during murine cardiogenesis. Development 131, 2219-2231 (2004).
Chang, C. P. et al. A field of myocardial-endocardial NFAT signaling underlies heart valve morphogenesis. Cell 118, 649-663 (2004).
Verzi, M. P., McCulley, D. J., De Val, S., Dodou, E. & Black, B. L. The right ventricle, outflow tract, and ventricular septum comprise a restricted expression domain within the secondary/anterior heart field. Dev. Biol. 287, 134-145 (2005).

(56) References Cited

OTHER PUBLICATIONS

Pandya, K. et al. Discordant on/off switching of gene expression in myocytes during cardiac hypertrophy in vivo. Proc. Natl Acad. Sci. USA 105, 13063-13068 (2008).
Wu, B. et al. Inducible cardiomyocyte-specific gene disruption directed by the rat Tnnt2 promoter in the mouse. Genesis 48, 63-72 (2009).
Szabo, G. et al. Poly(ADP-Ribose) polymerase inhibition reduces reperfusion injury after heart transplantation. Circ. Res. 90, 100-106 (2002).
Wang, Z. et al. Genome-wide mapping of HATs and HDACs reveals distinct functions in active and inactive genes. Cell 138, 1019-1031 (2009).
Morrow, A. G. & Brockenbrough, E. C. Surgical treatment of idiopathic hypertrophic subaortic stenosis: technic and hemodynamic results of subaortic ventriculomyotomy. Ann. Surg. 154, 181-189 (1961).
Kinugawa, K et al. Regulation of thyroid hormone receptor isoforms in physiological and pathological cardiac hypertrophy. Circ. Res. 89, 591-598 (2001).
Molkentin, J. D. et al. A calcineurin-dependent transcriptional pathway for cardiac hypertrophy. Cell 93, 215-228 (1998).
Boucher, P., Gotthardt, M., Li, W. P., Anderson, R. G. & Herz, J. LRP: role in vascular wall integrity and protection from atherosclerosis. Science 300, 329-332 (2003).
RIKEN Genome Exploration Research Group and Genome Science Group (Genome Network Project Core Group) and the FANTOM Consortium. Antisense transcription in the mammalian transcriptome. Science 309, 1564-1566 (2005).
Haddad, F., Bodell, P. W., Qin, A. X., Giger, J. M. & Baldwin, K. M. Role of antisense RNA in coordinating cardiac myosin heavy chain gene switching. J. Biol. Chem. 278, 37132-37138 (2003).
Hang, C. T. et al. Chromatin regulation by Brg1 underlies heart muscle development and disease. Nature 466, 62-67 (2010).
Hung, T. et al. Extensive and coordinated transcription of noncoding RNAs within cell-cycle promoters. Nature Genet. 43, 621-629 (2011).
Lin, M. F., Jungreis, I. & Kellis, M. PhyloCSF: a comparative genomics method to distinguish protein coding and non-coding regions. Bioinformatics 27, i275-i282 (2011).
Ingolia, N. T., Brar, G. A., Rouskin, S., McGeachy, A. M. & Weissman, J. S. The ribosome profiling strategy for monitoring translation in vivo by deep sequencing of ribosome-protected mRNA fragments. Nature Protocols 7, 1534-1550 (2012).
Lompre, A. M. et al. Myosin isoenzyme redistribution in chronic heart overload. Nature 282, 105-107 (1979).
Schultz, J. J. et al. TGF-b1 mediates the hypertrophic cardiomyocyte growth induced by angiotensin II. J. Clin. Invest. 109, 787-796 (2002).
Molkentin, J. D. & Dorn, G. W. II. Cytoplasmic signaling pathways that regulate cardiac hypertrophy. Annu. Rev. Physiol. 63, 391-426 (2001).
López, B. et al. Osteopontin-mediated myocardial fibrosis in heart failure: a role for lysyl oxidase? Cardiovasc. Res. 99, 111-120 (2013).
Frey, N. & Olson, E. N. Cardiac hypertrophy: the good, the bad, and the ugly. Annu. Rev. Physiol. 65, 45-79 (2003).
Guttman, M. et al. Chromatin signature reveals over a thousand highly conserved large non-coding RNAs in mammals. Nature 458, 223-227 (2009).
Rando, O. J. & Chang, H. Y. Genome-wide views of chromatin structure. Annu. Rev. Biochem. 78, 245-271 (2009).

\* cited by examiner

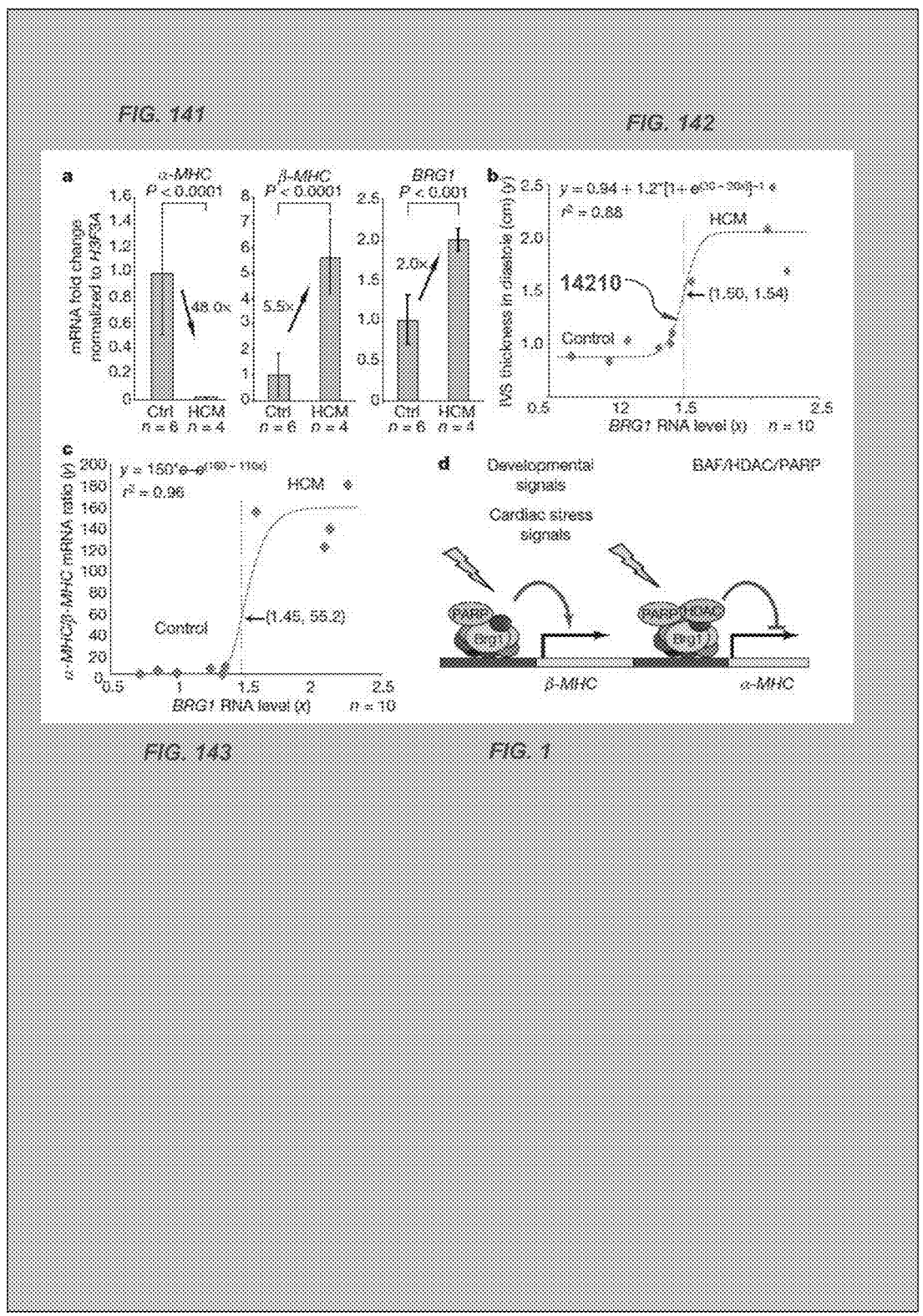

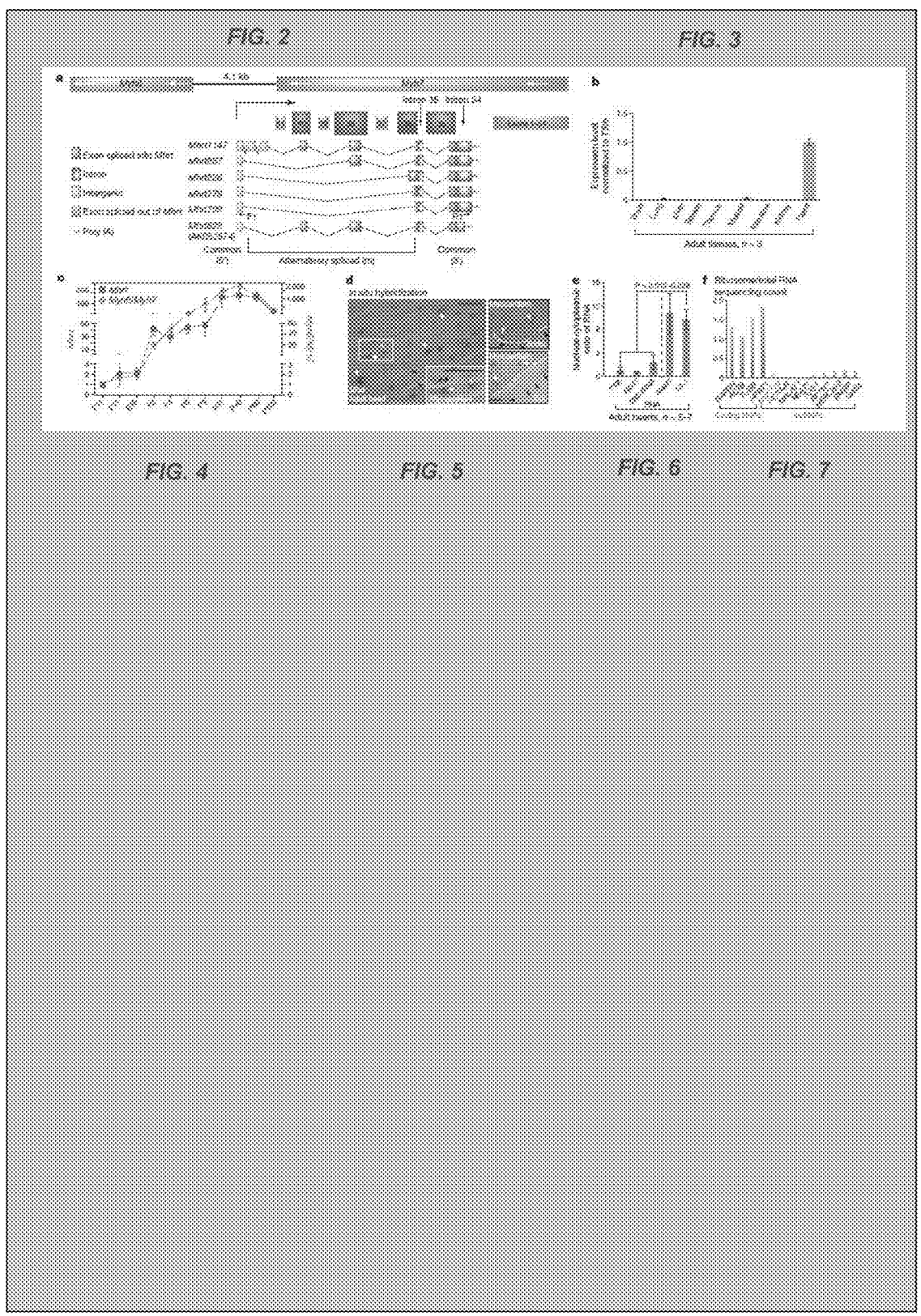

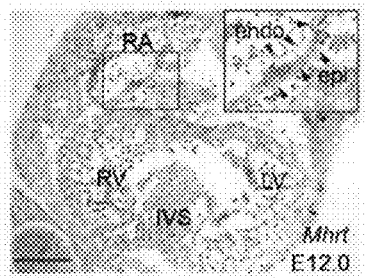
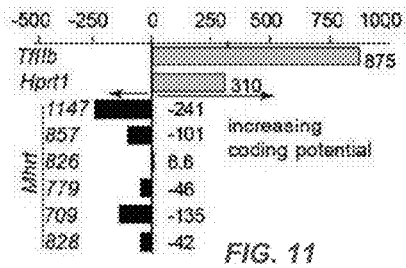
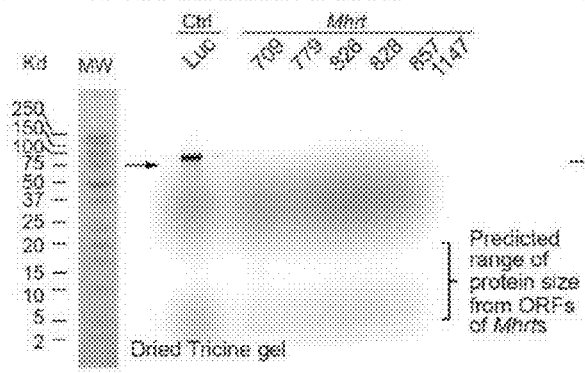
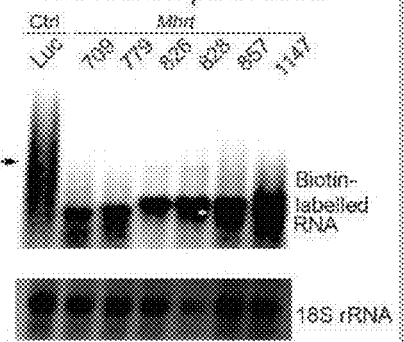
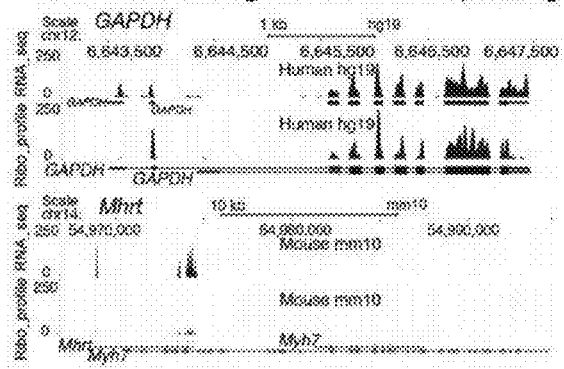
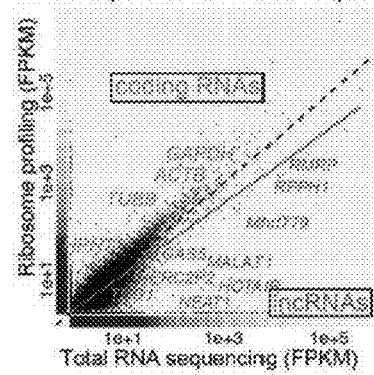

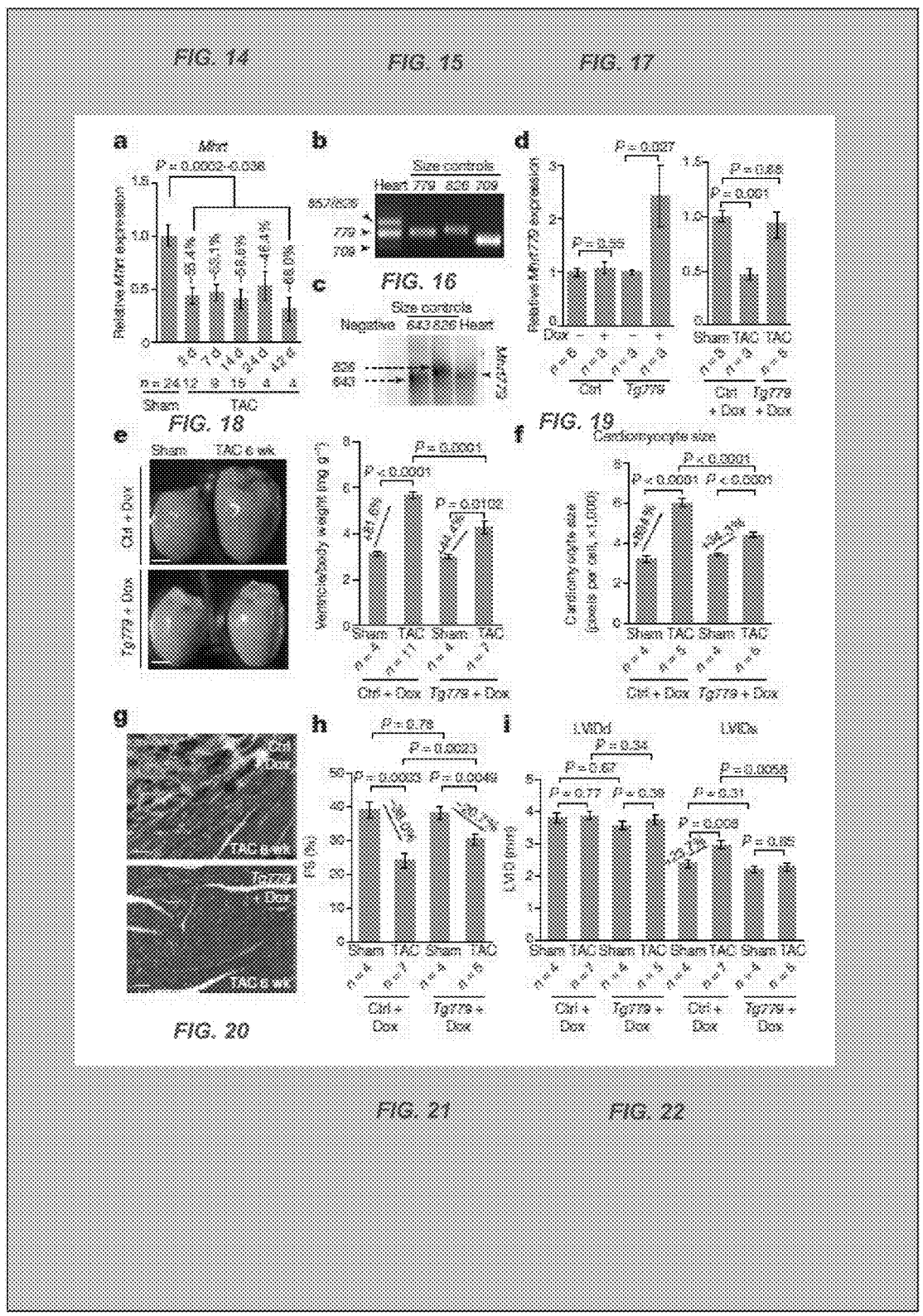

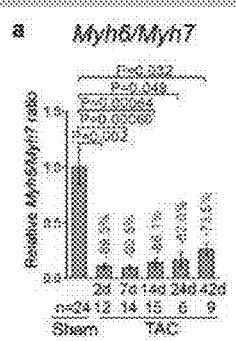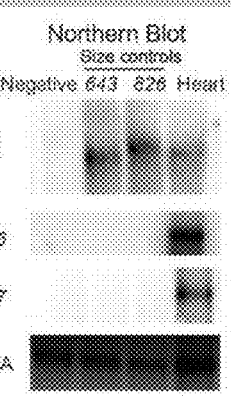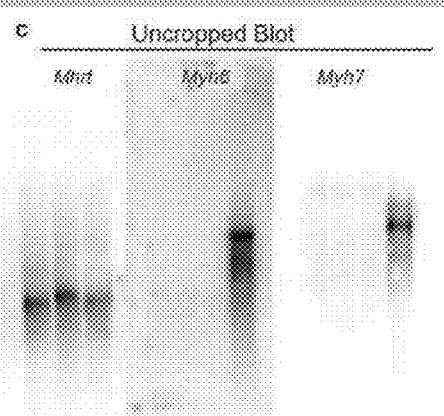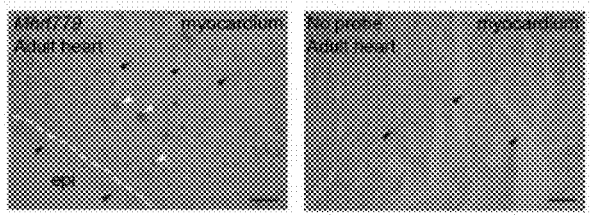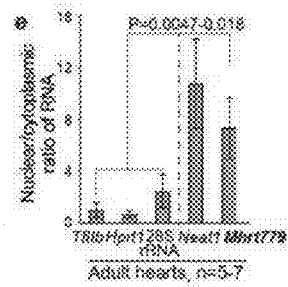
FIG. 23   FIG. 24   FIG. 25
FIG. 26   FIG. 27

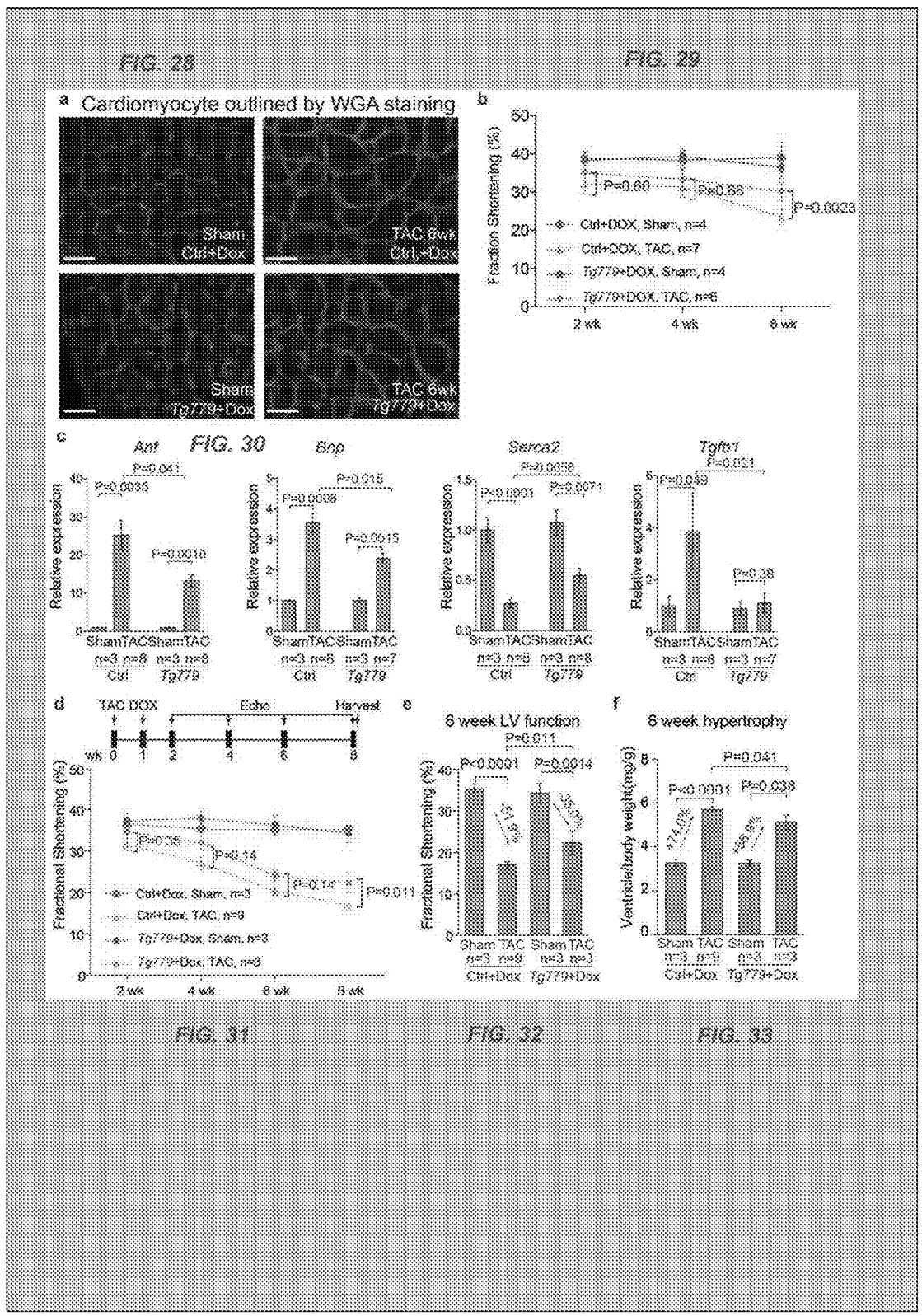

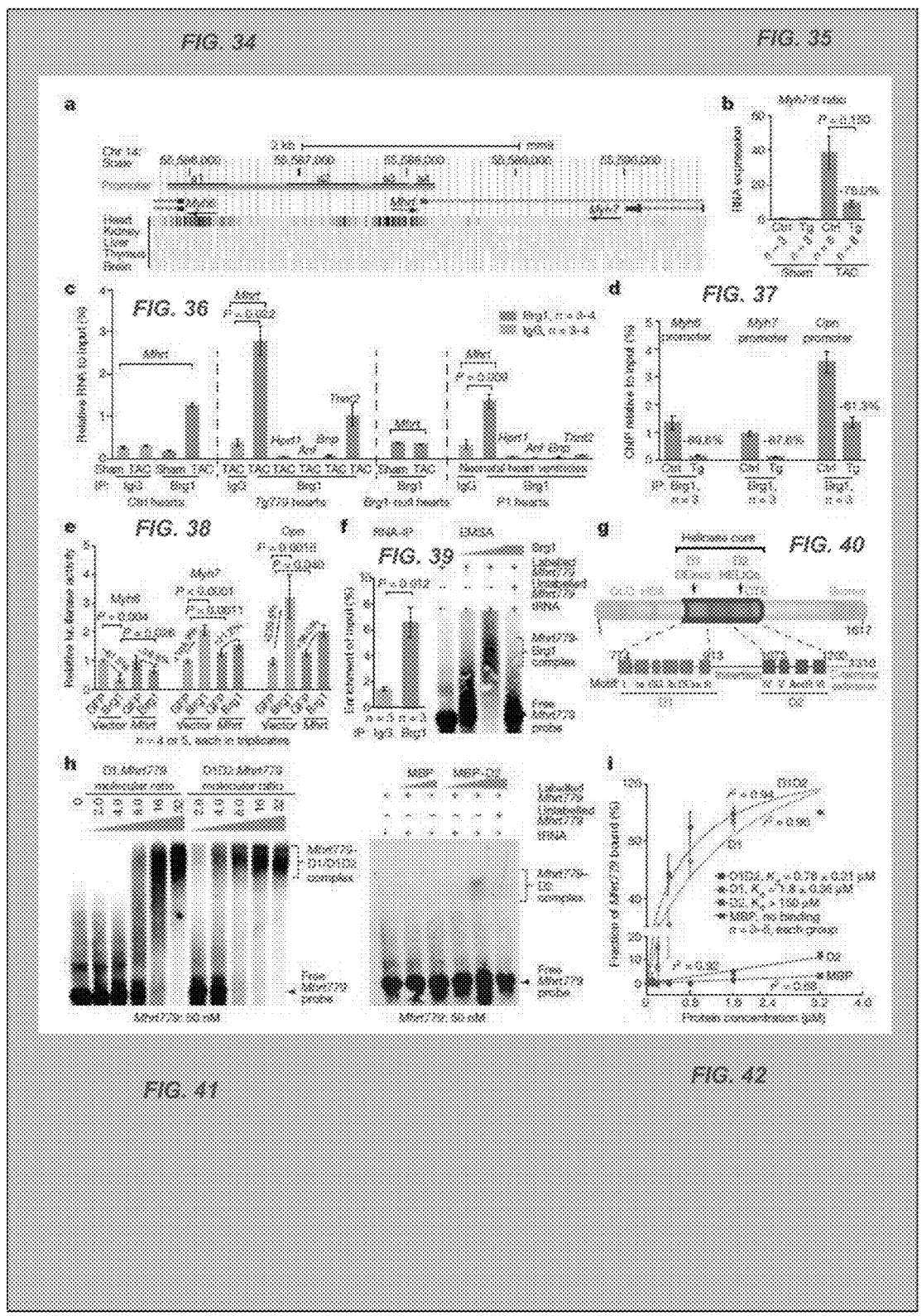

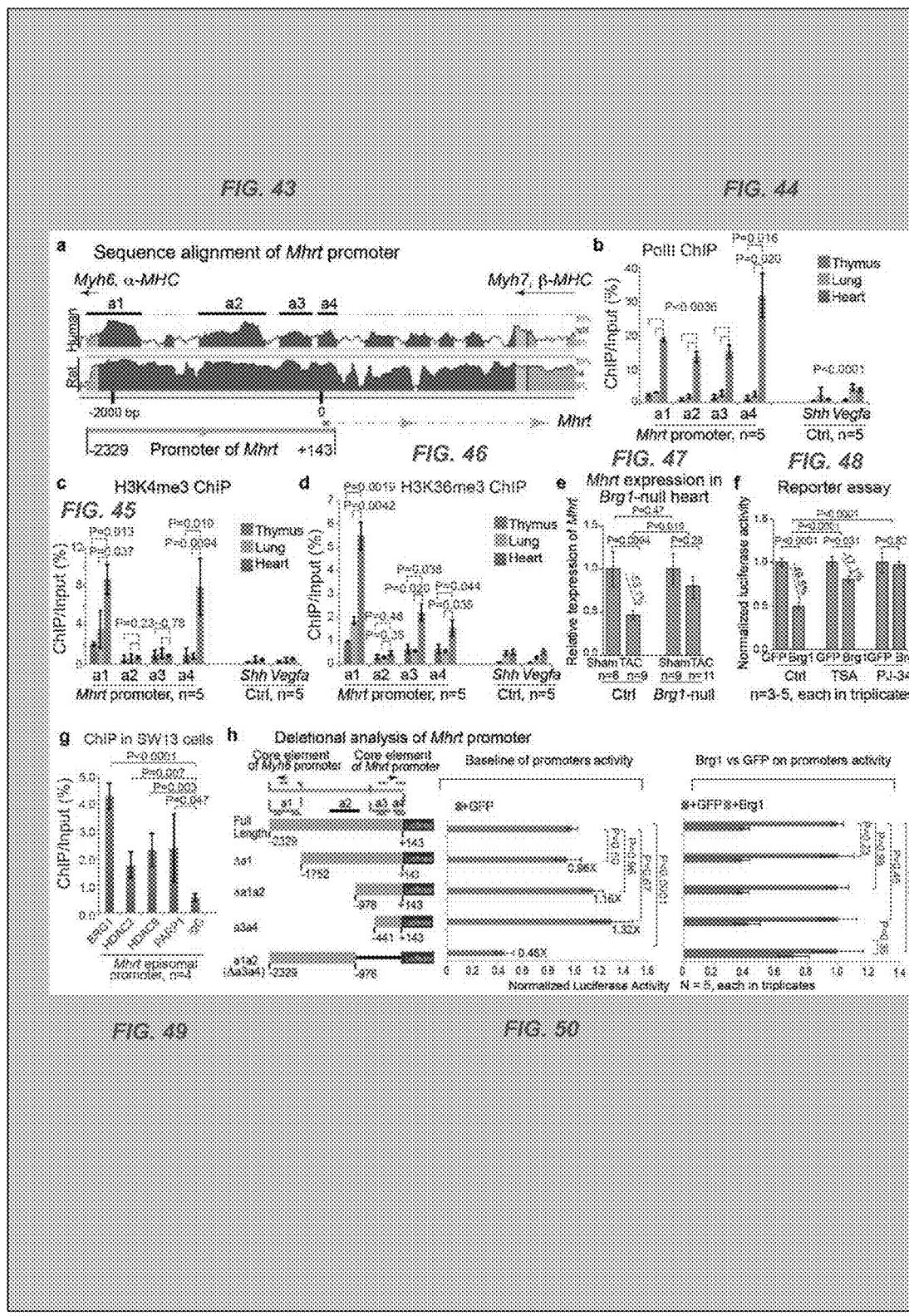

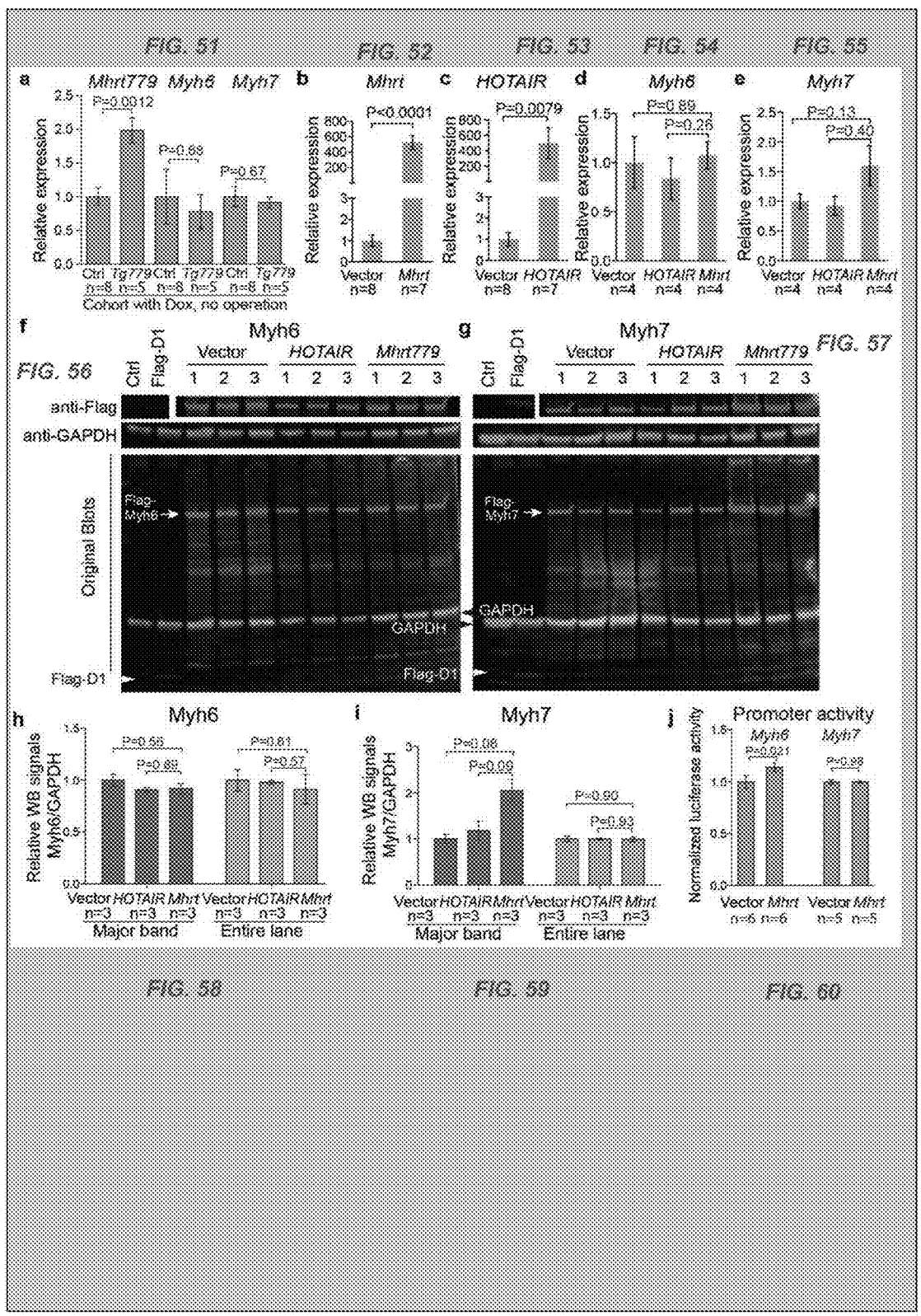

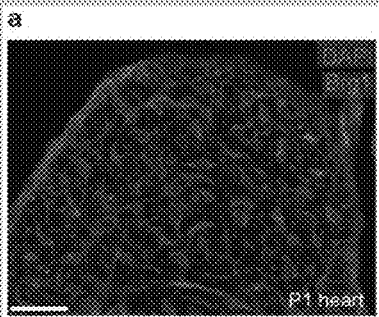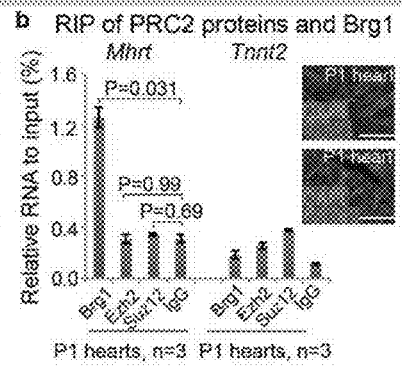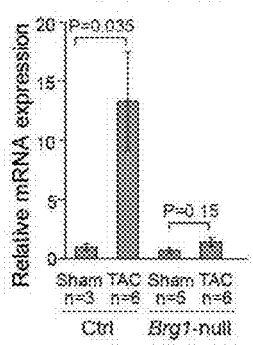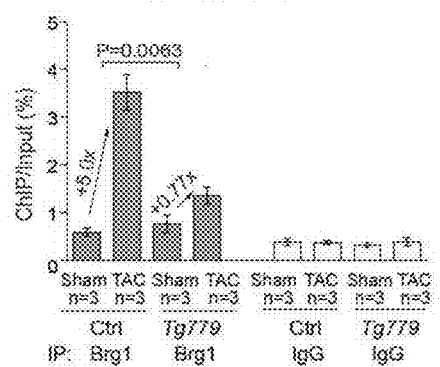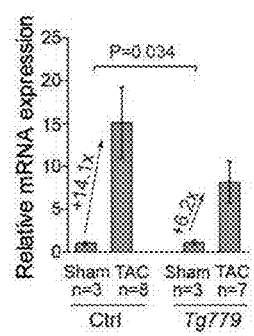

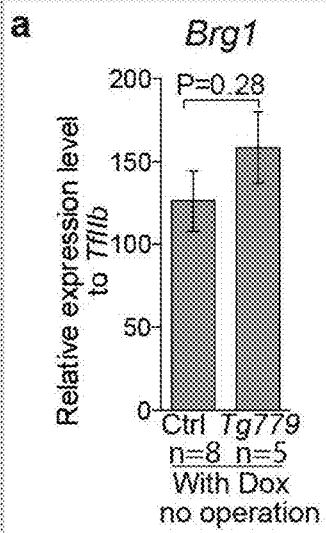
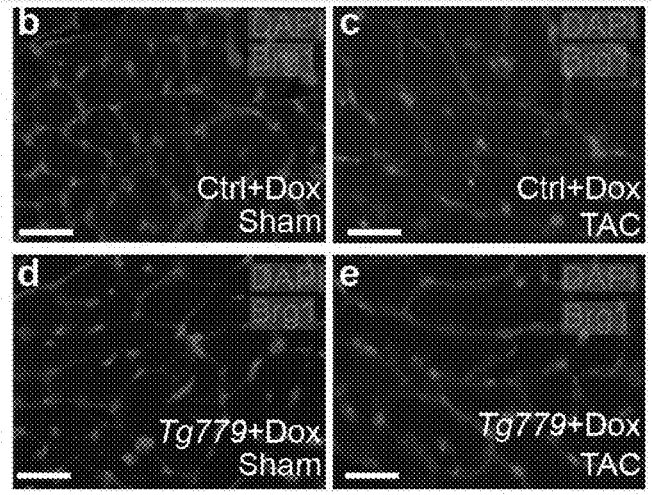
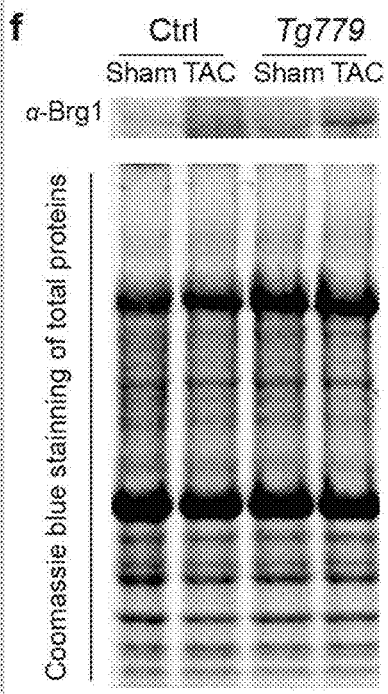
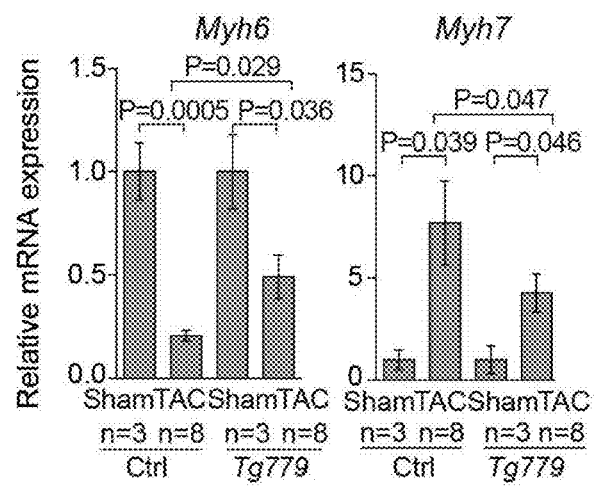

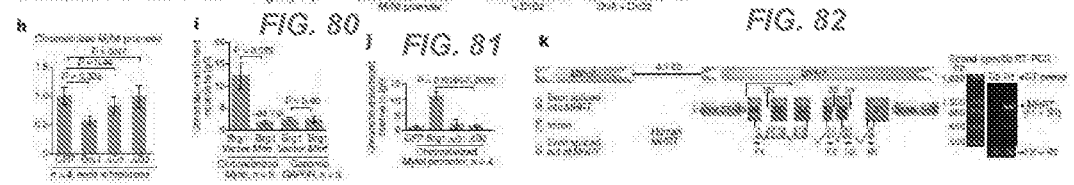
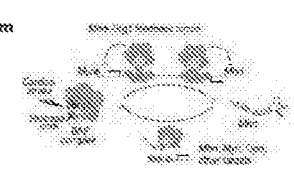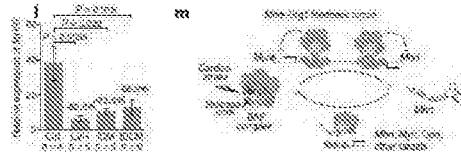
FIG. 73  FIG. 74  FIG. 75  FIG. 76  FIG. 77  FIG. 78
FIG. 79  FIG. 80  FIG. 81  FIG. 82
FIG. 83  FIG. 84  FIG. 85  FIG. 86

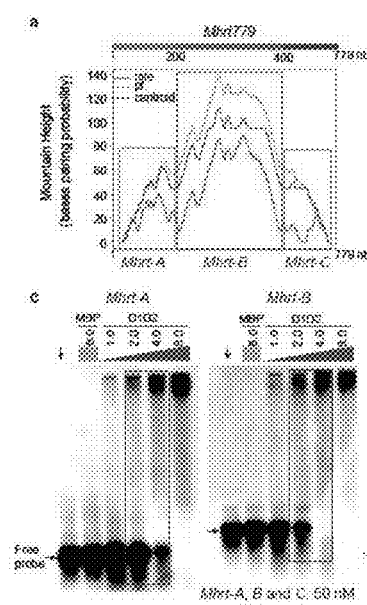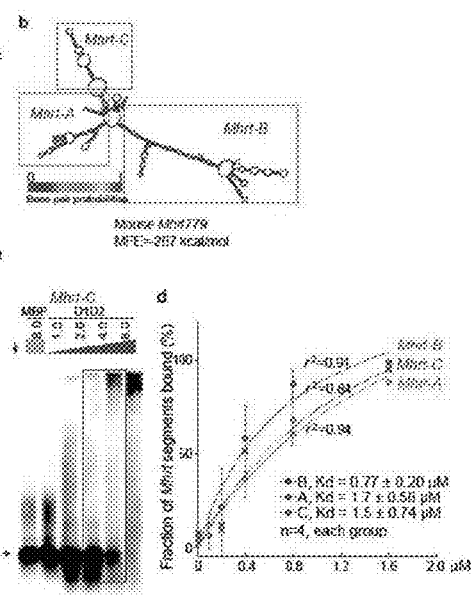
FIG. 87  FIG. 88  FIG. 89  FIG. 90

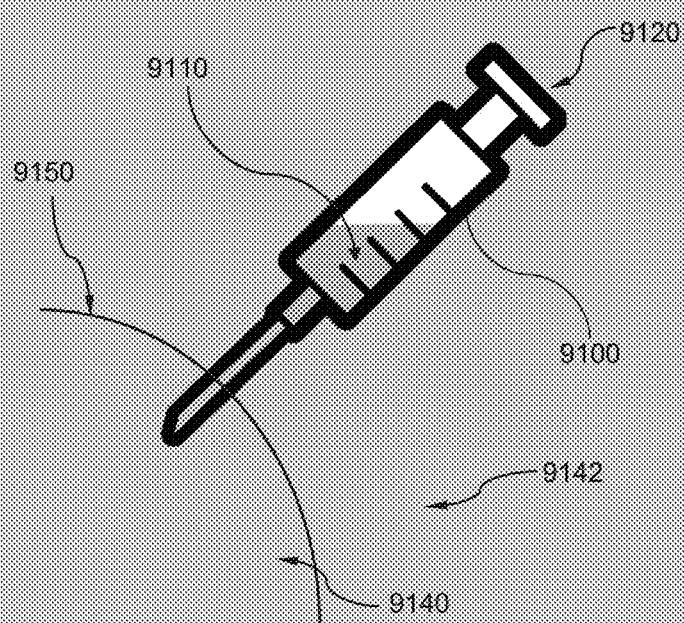

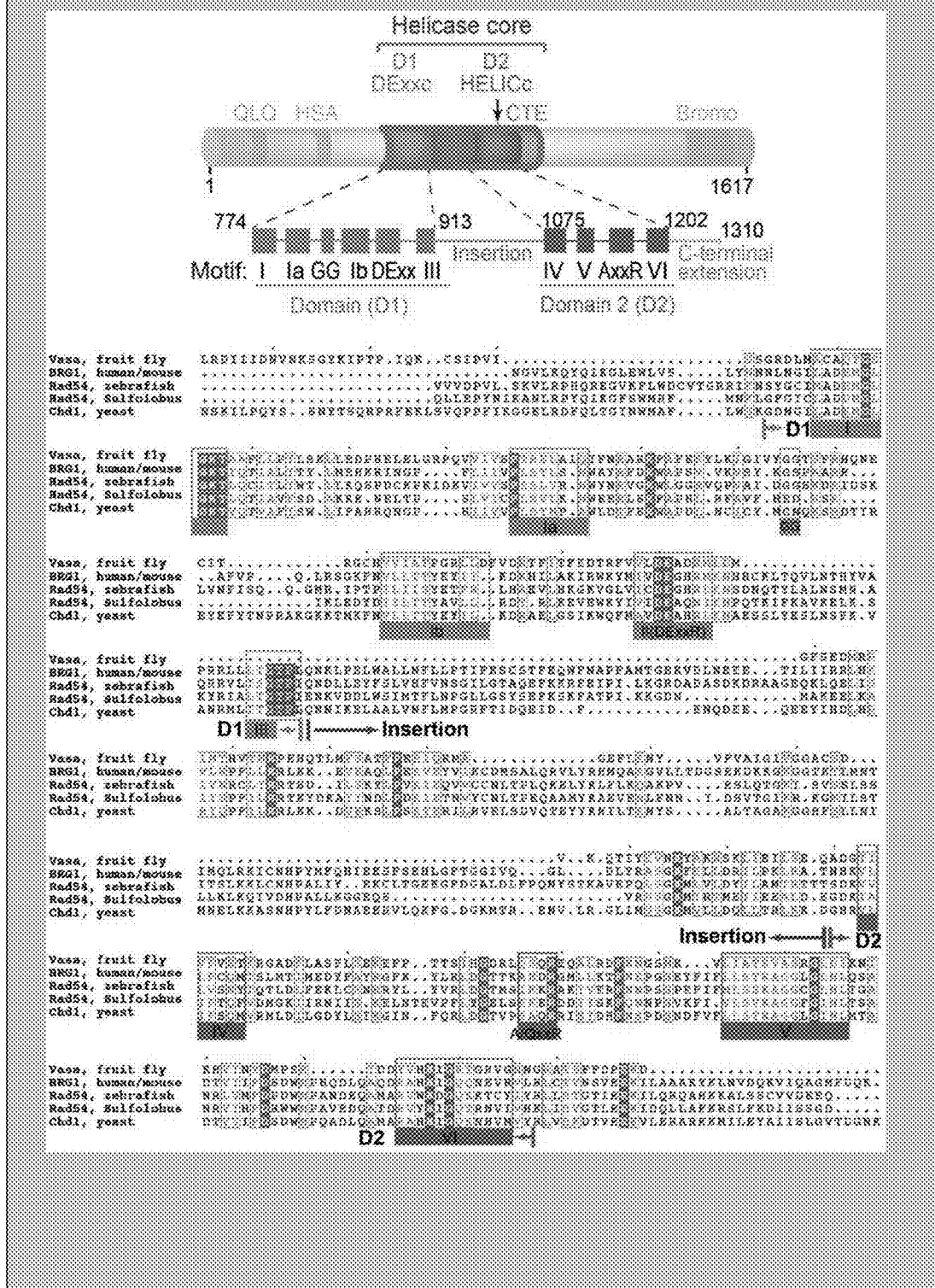

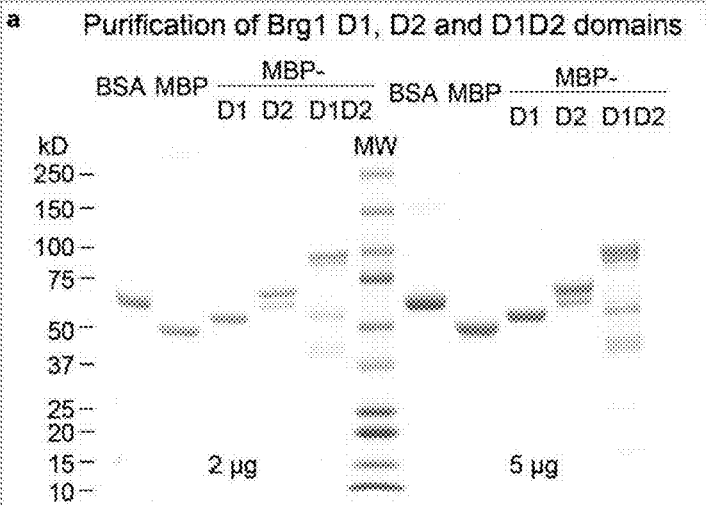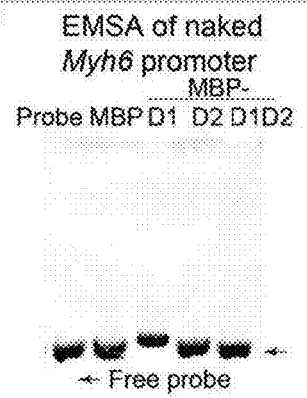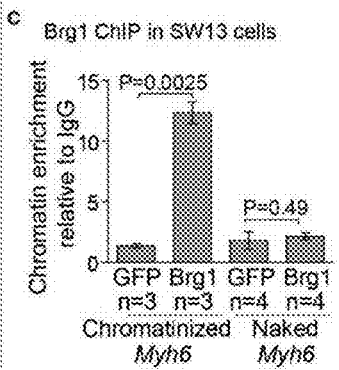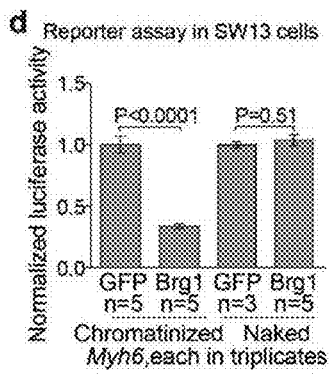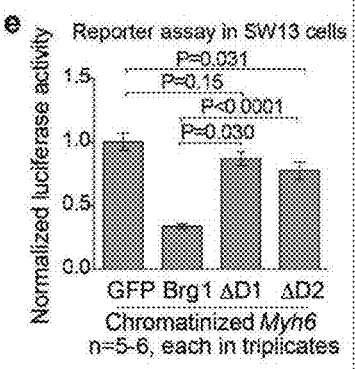

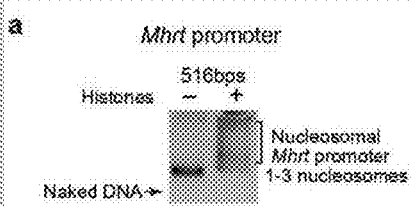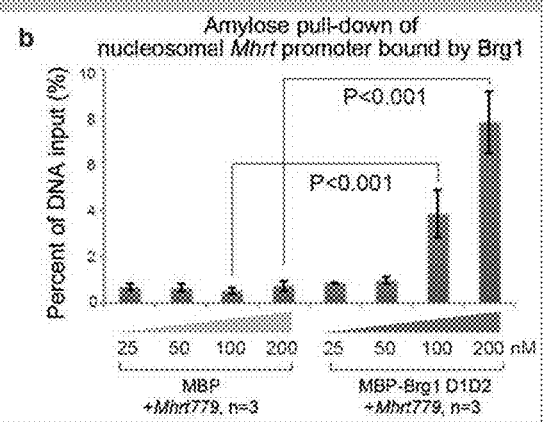

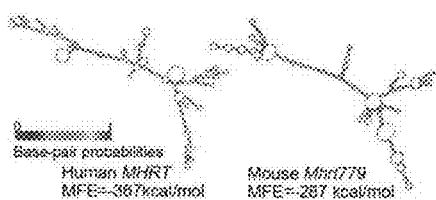

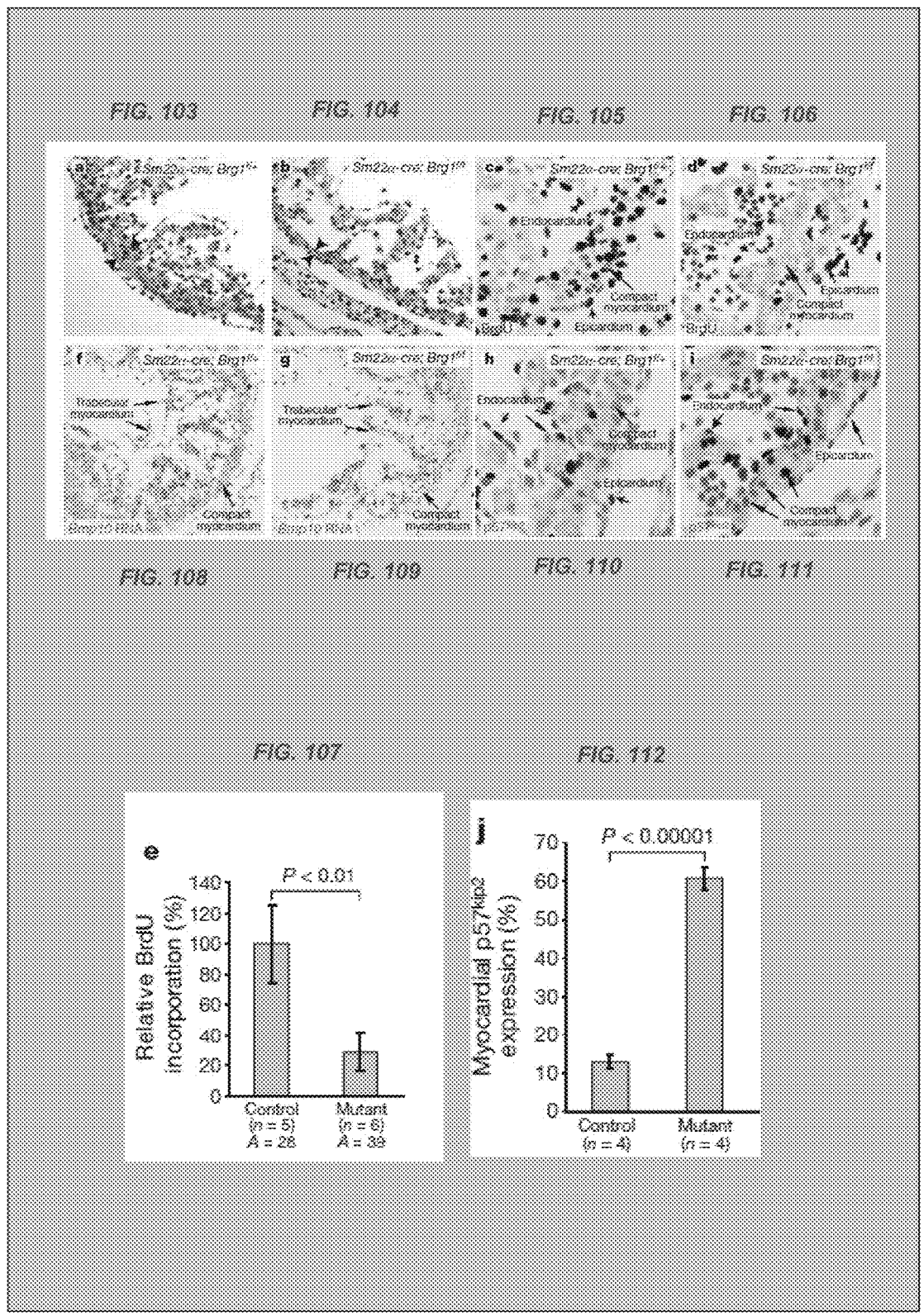

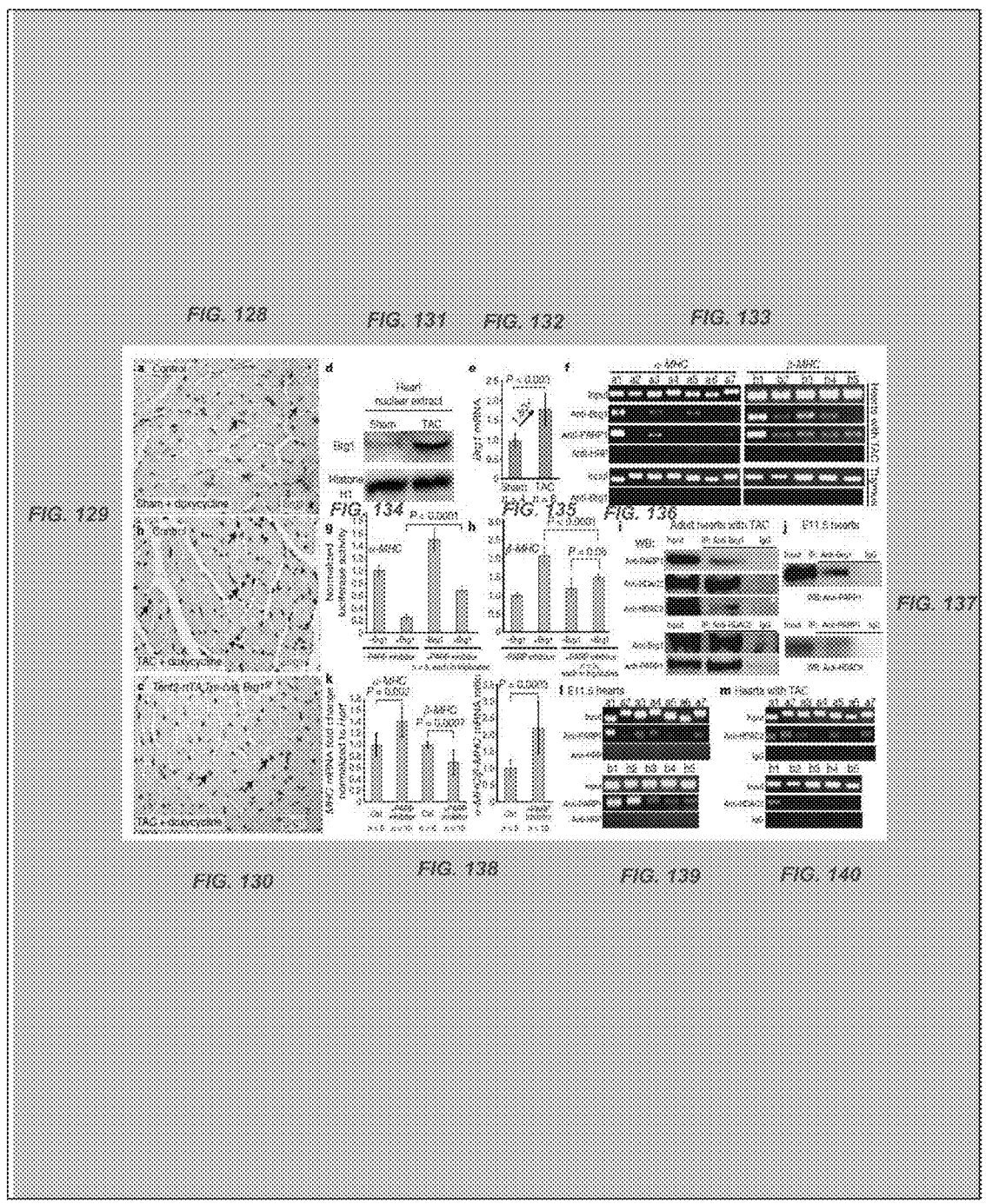

SEQUENCE LISTING

<160> NUMBER OF SEQ ID NOS: 75

<210> SEQ ID NO 1
<211> LENGTH: 779
<212> TYPE: RNA
<213> ORGANISM: Mus musculus

<400> SEQUENCE: 1

```
aagagcccua cagucugaug aacauucuag aguaugugga cacagaugga cgcucuggcc      60
acagcccgca gcuccuccag cuccgccugc agcagauugu ugcgccguuc cacgauggcg     120
auguucuccu ucaggucauc auuggcacgg acagcaucau ccagcuggau uugagugucc     180
ugaggaucag aaaaaugagu ggccucauug cggcugcgug ucuccgcauc cagggagguc     240
ugcagggagu ccaccauccg caggugguug cgcuuggccu gcuccaucuc cucauccuuc     300
ucugccagcu uccuuucgau cucugccuug aucgguuga acuccagcug ggcgcggagg     360
aucuugcccu ccucgugcuc cagggaggcc uggaaaggau auagauuuug caggcauaua     420
gucagagacc aggguggaag caagggugug ucuaaaaacc auggcacaga gagcauuugg     480
ggaugguaua caugacucag uaggagaugc agaggaagga aaugagaaag agugugcaca     540
agagaaauga aagcaagcug aagagaaggg gaugcagacu cccagggggg cggagggagu     600
cagcuuugaa gacaaagagg aaaaugaaaa guguugccaa ggaaacagag gcaaugaagc     660
agagaguaaa ggaaaaaaaa aaaaaaaacu accacacaca ggcaggcaga gguggaaagu     720
ggaaugagcu gaaauaggag ucuuucuaag guacaguaaa uaaaauguuu gugugaagg     779
```

<210> SEQ ID NO 2
<211> LENGTH: 400
<212> TYPE: RNA
<213> ORGANISM: Artificial Sequence
<220> FEATURE:
<223> OTHER INFORMATION: RNA sequence of a segment of the mouse myosin
      heavy-chain-associated RNA transcript 779 (Mouse Mhrt-B)

<400> SEQUENCE: 2

```
ggccucauug cggcugcgug ucuccgcauc cagggagguc ugcagggagu ccaccauccg      60
caggugguug cgcuuggccu gcuccaucuc cucauccuuc ucugccagcu uccuuucgau     120
cucugccuug aucgguuga acuccagcug ggcgcggagg aucuugcccu ccucgugcuc     180
cagggaggcc uggaaaggau auagauuuug caggcauaua gucagagacc aggguggaag     240
caagggugug ucuaaaaacc auggcacaga gagcauuugg ggaugguaua caugacucag     300
uaggagaugc agaggaagga aaugagaaag agugugcaca agagaaauga aagcaagcug     360
aagagaaggg gaugcagacu cccagggggg cggagggagu                          400
```

<210> SEQ ID NO 3
<211> LENGTH: 876
<212> TYPE: RNA
<213> ORGANISM: Homo sapiens

<400> SEQUENCE: 3

```
cuggagcugg gacaggucag cauccaucuu cuucuucugg uugaugaggc ugcugcucac      60
cugggaaugc agcagcugca cccgcucacu agucucaauc agcuccugcu ccgccagcuu     120
```

```
ccgggaccgc ucugucugcu ccaccacggc acgcaacucc uccagcucag ccugcagcag      180
guuguugcgc cgcuccacga uggcgauguu cuccuucagg ucgucguugg cacggacugc      240
aucguccagc ugaaucuggg uuaccuucaa caagcucugg aggcucuuga cuugcuucug      300
ggccucggcg gccaugcggu uggcguggcu gagcuggauc uccaucucau ugaggucucc      360
uuccaucuuc uucuucaccc ucagggccuc guugcggcug cgucucucug cguccaggga      420
ggucugcagc gaguccacca cccgcaggug guugcgcuug gccuguucca ucuccucguc      480
cuucucugcc agcuuccgcu cgaucucugc cuugaucugg uugaacucca gcugggcccg      540
gaggaucuug cccuccuccu gcuuucggac cuuuccagc ucauggauag ucuuuccgcu       600
ggaacccaac ugcucaguca agucggagau cuccucugug uggggaacac ggcguucuug     660
aguuugaaga gcucugugcu gagggagcga gccuccuucu gcgaggacuc cagcuccgac      720
ugcgacuccu cauacuucug cuuccacucg gccaggaucu gcccggggac aaggcucacu     780
cuucagcccc ccagccucag ccccaugucc aggggcugca gcagcagcau uggagcgcuc     840
uacguccacc aucaagucccu cgaucucauu cguag                              876

<210> SEQ ID NO 4
<211> LENGTH: 293
<212> TYPE: RNA
<213> ORGANISM: Artificial Sequence
<220> FEATURE:
<223> OTHER INFORMATION: RNA sequence of a segment of human myosin
      heavy-chain-associated RNA transcript (human MHRT-B)

<400> SEQUENCE: 4
gcuucugggc ucggcggcc augcggcuugg cguggcugag cuggaucucc aucucauuga       60
ggucuccuuc caucuucuuc uucacccuca gggccucguu gcggcucgcu gucucugcgu     120
ccagggaggu cugcagcgag uccaccaccc gcaggugguu gcgcuuggcc uguuccaucu      180
ccucguccuu cucugccagc uuccgcucga ucucugccuu gaucugguug aacccagcu       240 gggcccggag gaucuugccc uccuccgcu uucggaccuu cuccagcuca ugg             293

<210> SEQ ID NO 5
<211> LENGTH: 20
<212> TYPE: DNA
<213> ORGANISM: Artificial Sequence
<220> FEATURE:
<223> OTHER INFORMATION: Synthetic DNA sequence of a primer

<400> SEQUENCE: 5
cgcctggaga cgccatccac                                                   20

<210> SEQ ID NO 6
<211> LENGTH: 21
<212> TYPE: DNA
<213> ORGANISM: Artificial Sequence
<220> FEATURE:
<223> OTHER INFORMATION: Synthetic DNA sequence of a primer

<400> SEQUENCE: 6
tgtcttcaaa gctgactccc t                                                 21

<210> SEQ ID NO 7
<211> LENGTH: 20
<212> TYPE: DNA
<213> ORGANISM: Artificial Sequence
<220> FEATURE:
<223> OTHER INFORMATION: Synthetic DNA sequence of a primer
```

<400> SEQUENCE: 7
tcattggcac ggacagcatc					20

<210> SEQ ID NO 8
<211> LENGTH: 21
<212> TYPE: DNA
<213> ORGANISM: Artificial Sequence
<220> FEATURE:
<223> OTHER INFORMATION: Synthetic DNA sequence of a primer

<400> SEQUENCE: 8
gagcatttgg ggatggtata c					21

<210> SEQ ID NO 9
<211> LENGTH: 23
<212> TYPE: DNA
<213> ORGANISM: Artificial Sequence
<220> FEATURE:
<223> OTHER INFORMATION: Synthetic DNA sequence of a primer

<400> SEQUENCE: 9
caacactttt cattttcctc ttt				23

<210> SEQ ID NO 10
<211> LENGTH: 21
<212> TYPE: DNA
<213> ORGANISM: Artificial Sequence
<220> FEATURE:
<223> OTHER INFORMATION: Synthetic DNA sequence of a primer

<400> SEQUENCE: 10
tctgcttcat tgcctctgtt t					21

<210> SEQ ID NO 11
<211> LENGTH: 24
<212> TYPE: DNA
<213> ORGANISM: Artificial Sequence
<220> FEATURE:
<223> OTHER INFORMATION: Synthetic DNA sequence of a primer

<400> SEQUENCE: 11
aagagcccta cagtctgatg aaca				24

<210> SEQ ID NO 12
<211> LENGTH: 22
<212> TYPE: DNA
<213> ORGANISM: Artificial Sequence
<220> FEATURE:
<223> OTHER INFORMATION: Synthetic DNA sequence of a primer

<400> SEQUENCE: 12
ccttcacaca aacattttat tt				22

<210> SEQ ID NO 13
<211> LENGTH: 22
<212> TYPE: DNA
<213> ORGANISM: Artificial Sequence
<220> FEATURE:
<223> OTHER INFORMATION: Synthetic DNA sequence of a primer

<400> SEQUENCE: 13
ctacagaatg agatcgagga ct				22

<210> SEQ ID NO 14
<211> LENGTH: 20

```
<212> TYPE: DNA
<213> ORGANISM: Artificial Sequence
<220> FEATURE:
<223> OTHER INFORMATION: Synthetic DNA sequence of a primer

<400> SEQUENCE: 14
ggggctgaag agtgagcctt                                              20

<210> SEQ ID NO 15
<211> LENGTH: 22
<212> TYPE: DNA
<213> ORGANISM: Artificial Sequence
<220> FEATURE:
<223> OTHER INFORMATION: Synthetic DNA sequence of a primer

<400> SEQUENCE: 15
ctggagctgg gacaggtcag ca                                           22

<210> SEQ ID NO 16
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 16
tggggaacac ggcgttcttg a                                            21

<210> SEQ ID NO 17
<211> LENGTH: 23
<212> TYPE: DNA
<213> ORGANISM: Artificial Sequence
<220> FEATURE:
<223> OTHER INFORMATION: Synthetic DNA sequence of a primer

<400> SEQUENCE: 17
ctctgtggcg gcagcagcta ttt                                          23

<210> SEQ ID NO 18
<211> LENGTH: 23
<212> TYPE: DNA
<213> ORGANISM: Artificial Sequence
<220> FEATURE:
<223> OTHER INFORMATION: Synthetic DNA sequence of a primer

<400> SEQUENCE: 18
cgagggtaga tcagtctgta gga                                          23

<210> SEQ ID NO 19
<211> LENGTH: 19
<212> TYPE: DNA
<213> ORGANISM: Artificial Sequence
<220> FEATURE:
<223> OTHER INFORMATION: Synthetic DNA sequence of a primer

<400> SEQUENCE: 19
gctggtgaaa aggacctct                                               19

<210> SEQ ID NO 20
<211> LENGTH: 20
<212> TYPE: DNA
<213> ORGANISM: Artificial Sequence
<220> FEATURE:
<223> OTHER INFORMATION: Synthetic DNA sequence of a primer

<400> SEQUENCE: 20
```
cacaggacta gaacacctgc                                         20

<210> SEQ ID NO 21
<211> LENGTH: 22
<212> TYPE: DNA
<213> ORGANISM: Artificial Sequence
<220> FEATURE:
<223> OTHER INFORMATION: Synthetic DNA sequence of a primer

<400> SEQUENCE: 21
gactaggctg caacagcttc cg                                      22

<210> SEQ ID NO 22
<211> LENGTH: 22
<212> TYPE: DNA
<213> ORGANISM: Artificial Sequence
<220> FEATURE:
<223> OTHER INFORMATION: Synthetic DNA sequence of a primer

<400> SEQUENCE: 22
gccacagtgg caatgtgacc aa                                      22

<210> SEQ ID NO 23
<211> LENGTH: 21
<212> TYPE: DNA
<213> ORGANISM: Artificial Sequence
<220> FEATURE:
<223> OTHER INFORMATION: Synthetic DNA sequence of a primer

<400> SEQUENCE: 23
catttgcatt gcagtctgga t                                       21

<210> SEQ ID NO 24
<211> LENGTH: 21
<212> TYPE: DNA
<213> ORGANISM: Artificial Sequence
<220> FEATURE:
<223> OTHER INFORMATION: Synthetic DNA sequence of a primer

<400> SEQUENCE: 24
ctttgccatc ctacgagttc c                                       21

<210> SEQ ID NO 25
<211> LENGTH: 26
<212> TYPE: DNA
<213> ORGANISM: Artificial Sequence
<220> FEATURE:
<223> OTHER INFORMATION: Synthetic DNA sequence of a primer

<400> SEQUENCE: 25
tacagactct gatcgaggct cacttc                                  26

<210> SEQ ID NO 26
<211> LENGTH: 23
<212> TYPE: DNA
<213> ORGANISM: Artificial Sequence
<220> FEATURE:
<223> OTHER INFORMATION: Synthetic DNA sequence of a primer

<400> SEQUENCE: 26
tcattgcgaa tacgctgctg ctc                                     23

<210> SEQ ID NO 27
<211> LENGTH: 21
<212> TYPE: DNA
<213> ORGANISM: Artificial Sequence

```
<220> FEATURE:
<223> OTHER INFORMATION: Synthetic DNA sequence of a primer

<400> SEQUENCE: 27
gagcatttgg ggatggtata c                                             21

<210> SEQ ID NO 28
<211> LENGTH: 21
<212> TYPE: DNA
<213> ORGANISM: Artificial Sequence
<220> FEATURE:
<223> OTHER INFORMATION: Synthetic DNA sequence of a primer

<400> SEQUENCE: 28
tctgcttcat tgcctctgtt t                                             21

<210> SEQ ID NO 29
<211> LENGTH: 22
<212> TYPE: DNA
<213> ORGANISM: Artificial Sequence
<220> FEATURE:
<223> OTHER INFORMATION: Synthetic DNA sequence of a primer

<400> SEQUENCE: 29
tctggccaca gcccgcagct tc                                            22

<210> SEQ ID NO 30
<211> LENGTH: 21
<212> TYPE: DNA
<213> ORGANISM: Artificial Sequence
<220> FEATURE:
<223> OTHER INFORMATION: Synthetic DNA sequence of a primer

<400> SEQUENCE: 30
agtcatgtat accatcccca a                                             21

<210> SEQ ID NO 31
<211> LENGTH: 20
<212> TYPE: DNA
<213> ORGANISM: Artificial Sequence
<220> FEATURE:
<223> OTHER INFORMATION: Synthetic DNA sequence of a primer

<400> SEQUENCE: 31
tctcctggag ccacatctct                                               20

<210> SEQ ID NO 32
<211> LENGTH: 20
<212> TYPE: DNA
<213> ORGANISM: Artificial Sequence
<220> FEATURE:
<223> OTHER INFORMATION: Synthetic DNA sequence of a primer

<400> SEQUENCE: 32
gcttttcctt aggcccaaac                                               20

<210> SEQ ID NO 33
<211> LENGTH: 21
<212> TYPE: DNA
<213> ORGANISM: Artificial Sequence
<220> FEATURE:
<223> OTHER INFORMATION: Synthetic DNA sequence of a primer

<400> SEQUENCE: 33
ggtagccaaa tgcctcgtca t                                             21
```

<210> SEQ ID NO 34
<211> LENGTH: 18
<212> TYPE: DNA
<213> ORGANISM: Artificial Sequence
<220> FEATURE:
<223> OTHER INFORMATION: Synthetic DNA sequence of a primer

<400> SEQUENCE: 34
cccttggctg tggtttcg                                                       18

<210> SEQ ID NO 35
<211> LENGTH: 23
<212> TYPE: DNA
<213> ORGANISM: Artificial Sequence
<220> FEATURE:
<223> OTHER INFORMATION: Synthetic DNA sequence of a primer

<400> SEQUENCE: 35
accaccccaa tggatgcaga cag                                                 23

<210> SEQ ID NO 36
<211> LENGTH: 20
<212> TYPE: DNA
<213> ORGANISM: Artificial Sequence
<220> FEATURE:
<223> OTHER INFORMATION: Synthetic DNA sequence of a primer

<400> SEQUENCE: 36
acgggctaag cgtctggcac                                                     20

<210> SEQ ID NO 37
<211> LENGTH: 21
<212> TYPE: DNA
<213> ORGANISM: Artificial Sequence
<220> FEATURE:
<223> OTHER INFORMATION: Synthetic DNA sequence of a primer

<400> SEQUENCE: 37
tggggaacac ggcgttcttg a                                                   21

<210> SEQ ID NO 38
<211> LENGTH: 20
<212> TYPE: DNA
<213> ORGANISM: Artificial Sequence
<220> FEATURE:
<223> OTHER INFORMATION: Synthetic DNA sequence of a primer

<400> SEQUENCE: 38
ggggctgaag agtgagcctt                                                     20

<210> SEQ ID NO 39
<211> LENGTH: 23
<212> TYPE: DNA
<213> ORGANISM: Artificial Sequence
<220> FEATURE:
<223> OTHER INFORMATION: Synthetic DNA sequence of a primer

<400> SEQUENCE: 39
ggtagaaaaa gcaaccacga agc                                                 23

<210> SEQ ID NO 40
<211> LENGTH: 25
<212> TYPE: DNA
<213> ORGANISM: Artificial Sequence
<220> FEATURE:
<223> OTHER INFORMATION: Synthetic DNA sequence of a primer

<400> SEQUENCE: 40
acataaacct ctgtctgtga gtgcc                                    25

<210> SEQ ID NO 41
<211> LENGTH: 22
<212> TYPE: DNA
<213> ORGANISM: Artificial Sequence
<220> FEATURE:
<223> OTHER INFORMATION: Synthetic DNA sequence of a primer

<400> SEQUENCE: 41
ccgggaaact gtggcgtgat gg                                       22

<210> SEQ ID NO 42
<211> LENGTH: 25
<212> TYPE: DNA
<213> ORGANISM: Artificial Sequence
<220> FEATURE:
<223> OTHER INFORMATION: Synthetic DNA sequence of a primer

<400> SEQUENCE: 42
aggtggagga gtgggtgtcg ctgtt                                    25

<210> SEQ ID NO 43
<211> LENGTH: 20
<212> TYPE: DNA
<213> ORGANISM: Artificial Sequence
<220> FEATURE:
<223> OTHER INFORMATION: Synthetic DNA sequence of a primer

<400> SEQUENCE: 43
gcagatagcc agggttgaaa                                          20

<210> SEQ ID NO 44
<211> LENGTH: 40
<212> TYPE: DNA
<213> ORGANISM: Artificial Sequence
<220> FEATURE:
<223> OTHER INFORMATION: Synthetic DNA sequence of a primer

<400> SEQUENCE: 44
tgggtaaggg tcaccttctc gcagatagcc agggttgaaa                    40

<210> SEQ ID NO 45
<211> LENGTH: 22
<212> TYPE: DNA
<213> ORGANISM: Artificial Sequence
<220> FEATURE:
<223> OTHER INFORMATION: Synthetic DNA sequence of a primer

<400> SEQUENCE: 45
gtgacaacag ccctttctaa at                                       22

<210> SEQ ID NO 46
<211> LENGTH: 20
<212> TYPE: DNA
<213> ORGANISM: Artificial Sequence
<220> FEATURE:
<223> OTHER INFORMATION: Synthetic DNA sequence of a primer

<400> SEQUENCE: 46
ctccagctcc cactcctacc                                          20

<210> SEQ ID NO 47

```
<211> LENGTH: 21
<212> TYPE: DNA
<213> ORGANISM: Artificial Sequence
<220> FEATURE:
<223> OTHER INFORMATION: Synthetic DNA sequence of a primer

<400> SEQUENCE: 47
gagaacatta cagggtagga a                                          21

<210> SEQ ID NO 48
<211> LENGTH: 19
<212> TYPE: DNA
<213> ORGANISM: Artificial Sequence
<220> FEATURE:
<223> OTHER INFORMATION: Synthetic DNA sequence of a primer

<400> SEQUENCE: 48
gaagcagtga ggttggtgg                                             19

<210> SEQ ID NO 49
<211> LENGTH: 21
<212> TYPE: DNA
<213> ORGANISM: Artificial Sequence
<220> FEATURE:
<223> OTHER INFORMATION: Synthetic DNA sequence of a primer

<400> SEQUENCE: 49
caaatcccag agcacagact c                                          21

<210> SEQ ID NO 50
<211> LENGTH: 21
<212> TYPE: DNA
<213> ORGANISM: Artificial Sequence
<220> FEATURE:
<223> OTHER INFORMATION: Synthetic DNA sequence of a primer

<400> SEQUENCE: 50
agcgcagagg cttggggcag c                                          21

<210> SEQ ID NO 51
<211> LENGTH: 20
<212> TYPE: DNA
<213> ORGANISM: Artificial Sequence
<220> FEATURE:
<223> OTHER INFORMATION: Synthetic DNA sequence of a primer

<400> SEQUENCE: 51
tactagcggt tttacgggcg                                            20

<210> SEQ ID NO 52
<211> LENGTH: 24
<212> TYPE: DNA
<213> ORGANISM: Artificial Sequence
<220> FEATURE:
<223> OTHER INFORMATION: Synthetic DNA sequence of a primer

<400> SEQUENCE: 52
tcgaacagga ggagcagaga gcga                                       24

<210> SEQ ID NO 53
<211> LENGTH: 21
<212> TYPE: DNA
<213> ORGANISM: Artificial Sequence
<220> FEATURE:
<223> OTHER INFORMATION: Synthetic DNA sequence of a primer

<400> SEQUENCE: 53
```
accggcctga accccacttc c                                              21

<210> SEQ ID NO 54
<211> LENGTH: 21
<212> TYPE: DNA
<213> ORGANISM: Artificial Sequence
<220> FEATURE:
<223> OTHER INFORMATION: Synthetic DNA sequence of a primer

<400> SEQUENCE: 54
atgtcgagac agggaacaga a                                              21

<210> SEQ ID NO 55
<211> LENGTH: 20
<212> TYPE: DNA
<213> ORGANISM: Artificial Sequence
<220> FEATURE:
<223> OTHER INFORMATION: Synthetic DNA sequence of a primer

<400> SEQUENCE: 55
cgatgcgctg cgaatcggga                                                20

<210> SEQ ID NO 56
<211> LENGTH: 20
<212> TYPE: DNA
<213> ORGANISM: Artificial Sequence
<220> FEATURE:
<223> OTHER INFORMATION: Synthetic DNA sequence of a primer

<400> SEQUENCE: 56
cactgaagcg ggaagggact                                                20

<210> SEQ ID NO 57
<211> LENGTH: 20
<212> TYPE: DNA
<213> ORGANISM: Artificial Sequence
<220> FEATURE:
<223> OTHER INFORMATION: Synthetic DNA sequence of a primer

<400> SEQUENCE: 57
caagcaagag cctacgacca                                                20

<210> SEQ ID NO 58
<211> LENGTH: 20
<212> TYPE: DNA
<213> ORGANISM: Artificial Sequence
<220> FEATURE:
<223> OTHER INFORMATION: Synthetic DNA sequence of a primer

<400> SEQUENCE: 58
attcgttgga attcctcggg                                                20

<210> SEQ ID NO 59
<211> LENGTH: 20
<212> TYPE: DNA
<213> ORGANISM: Artificial Sequence
<220> FEATURE:
<223> OTHER INFORMATION: Synthetic DNA sequence of a primer

<400> SEQUENCE: 59
taaagcacga ggaagcggtc                                                20

<210> SEQ ID NO 60
<211> LENGTH: 19
<212> TYPE: DNA

<213> ORGANISM: Artificial Sequence
<220> FEATURE:
<223> OTHER INFORMATION: Synthetic DNA sequence of a primer

<400> SEQUENCE: 60
tcgaccccaa gcgaaacat    19

<210> SEQ ID NO 61
<211> LENGTH: 20
<212> TYPE: DNA
<213> ORGANISM: Artificial Sequence
<220> FEATURE:
<223> OTHER INFORMATION: Synthetic DNA sequence of a primer

<400> SEQUENCE: 61
gcagatagcc agggttgaaa    20

<210> SEQ ID NO 62
<211> LENGTH: 20
<212> TYPE: DNA
<213> ORGANISM: Artificial Sequence
<220> FEATURE:
<223> OTHER INFORMATION: Synthetic DNA sequence of a primer

<400> SEQUENCE: 62
tgggtaaggg tcaccttctc    20

<210> SEQ ID NO 63
<211> LENGTH: 20
<212> TYPE: DNA
<213> ORGANISM: Artificial Sequence
<220> FEATURE:
<223> OTHER INFORMATION: Synthetic DNA sequence of a primer

<400> SEQUENCE: 63
atgccaaatg gttgctctttt    20

<210> SEQ ID NO 64
<211> LENGTH: 20
<212> TYPE: DNA
<213> ORGANISM: Artificial Sequence
<220> FEATURE:
<223> OTHER INFORMATION: Synthetic DNA sequence of a primer

<400> SEQUENCE: 64
gagcttgaga accaggcagt    20

<210> SEQ ID NO 65
<211> LENGTH: 35
<212> TYPE: DNA
<213> ORGANISM: Artificial Sequence
<220> FEATURE:
<223> OTHER INFORMATION: Synthetic DNA sequence of a primer

<400> SEQUENCE: 65
cccggggcta gcctgcagaa caagctaccg gagct    35

<210> SEQ ID NO 66
<211> LENGTH: 35
<212> TYPE: DNA
<213> ORGANISM: Artificial Sequence
<220> FEATURE:
<223> OTHER INFORMATION: Synthetic DNA sequence of a primer

<400> SEQUENCE: 66
cccggggcta gccaggttgt tgttgtacag ggaca    35

-continued

```
<210> SEQ ID NO 67
<211> LENGTH: 33
<212> TYPE: DNA
<213> ORGANISM: Artificial Sequence
<220> FEATURE:
<223> OTHER INFORMATION: Synthetic DNA sequence of a primer

<400> SEQUENCE: 67
cccggggcta gcatcaagaa gttcaaattt ccc                                 33

<210> SEQ ID NO 68
<211> LENGTH: 39
<212> TYPE: DNA
<213> ORGANISM: Artificial Sequence
<220> FEATURE:
<223> OTHER INFORMATION: Synthetic DNA sequence of a primer

<400> SEQUENCE: 68
cccggggcta gcctgcaggc catcctggag cacgagcag                           39

<210> SEQ ID NO 69
<211> LENGTH: 347
<212> TYPE: PRT
<213> ORGANISM: drosophila

<400> SEQUENCE: 69

Leu Arg Asp Ile Ile Ile Asp Asn Val Asn Lys Ser Gly Tyr Lys Ile
 1               5                  10                  15

Pro Thr Pro Ile Gln Lys Cys Ser Ile Pro Val Ile Ser Ser Gly Arg
            20                  25                  30

Asp Leu Met Ala Cys Ala Gln Thr Gly Ser Gly Lys Thr Ala Ala Phe
        35                  40                  45

Leu Leu Pro Ile Leu Ser Lys Leu Leu Glu Asp Pro His Glu Leu Glu
    50                  55                  60

Leu Gly Arg Pro Gln Val Val Ile Val Ser Pro Thr Arg Arg Leu Ala
65                  70                  75                  80

Ile Gln Ile Phe Asn Glu Ala Arg Lys Phe Ala Phe Glu Ser Tyr Leu
                85                  90                  95

Lys Ile Gly Ile Val Tyr Gly Gly Thr Ser Phe Arg His Gln Asn Glu
            100                 105                 110

Cys Ile Thr Arg Gly Cys His Val Val Ile Ala Thr Pro Gly Arg Leu
        115                 120                 125

Leu Asp Phe Val Asp Arg Thr Phe Ile Thr Phe Glu Asp Thr Arg Phe
    130                 135                 140

Val Val Leu Asp Glu Ala Asp Arg Met Leu Asp Met Gly Phe Ser Glu
145                 150                 155                 160

Asp Met Arg Arg Ile Met Thr His Val Thr Met Arg Pro Glu His Gln
                165                 170                 175

Thr Leu Met Phe Ser Ala Thr Phe Pro Glu Glu Ile Gln Arg Met Ala
            180                 185                 190

Gly Glu Phe Leu Lys Asn Tyr Val Phe Val Ala Ile Gly Ile Val Gly
        195                 200                 205

Gly Ala Cys Ser Asp Val Lys Gln Thr Ile Tyr Glu Val Asn Lys Tyr
    210                 215                 220

Ala Lys Arg Ser Lys Leu Ile Glu Ile Leu Ser Glu Gln Ala Asp Gly
225                 230                 235                 240

Thr Ile Val Phe Val Glu Thr Lys Arg Gly Ala Asp Phe Leu Ala Ser
```

-continued

```
                245                 250                 255
Phe Leu Ser Glu Lys Glu Phe Pro Thr Thr Ser Ile His Gly Asp Arg
            260                 265                 270

Leu Gln Ser Gln Arg Glu Gln Ala Leu Arg Asp Phe Lys Asn Gly Ser
        275                 280                 285

Met Lys Val Leu Ile Ala Thr Ser Val Ala Ser Arg Gly Leu Asp Ile
    290                 295                 300

Lys Asn Ile Lys His Val Ile Asn Tyr Asp Met Pro Ser Lys Ile Asp
305                 310                 315                 320

Asp Tyr Val His Arg Ile Gly Arg Thr Gly Arg Val Gly Asn Asn Gly
                325                 330                 335

Arg Ala Thr Ser Phe Phe Asp Pro Glu Lys Asp
                340                 345
```

<210> SEQ ID NO 70
<211> LENGTH: 486
<212> TYPE: PRT
<213> ORGANISM: Homo sapiens

<400> SEQUENCE: 70

```
Asn Gly Val Leu Lys Gln Tyr Gln Ile Lys Gly Leu Glu Trp Leu Val
1               5                   10                  15

Ser Leu Tyr Asn Asn Asn Leu Asn Gly Ile Leu Ala Asp Glu Met Gly
            20                  25                  30

Leu Gly Lys Thr Ile Gln Thr Ile Ala Leu Ile Thr Tyr Leu Met Glu
        35                  40                  45

His Lys Arg Ile Asn Gly Pro Phe Leu Ile Ile Val Pro Leu Ser Thr
    50                  55                  60

Leu Ser Asn Trp Ala Tyr Glu Phe Asp Lys Trp Ala Pro Ser Val Val
65                  70                  75                  80

Lys Val Ser Tyr Lys Gly Ser Ala Ala Arg Ala Phe Val Pro Gln
                85                  90                  95

Leu Arg Ser Gly Lys Phe Asn Val Leu Leu Thr Thr Tyr Glu Tyr Ile
            100                 105                 110

Ile Lys Asp Lys His Ile Leu Ala Lys Ile Arg Trp Lys Tyr Met Ile
        115                 120                 125

Val Asp Glu Gly His Arg Met Lys Asn His His Cys Lys Leu Thr Gln
    130                 135                 140

Val Leu Asn Thr His Tyr Val Ala Pro Arg Arg Leu Leu Leu Thr Gly
145                 150                 155                 160

Thr Pro Leu Gln Asn Lys Leu Pro Glu Leu Trp Ala Leu Leu Asn Phe
                165                 170                 175

Leu Leu Pro Thr Ile Phe Lys Ser Cys Ser Thr Phe Glu Gln Trp Phe
            180                 185                 190

Asn Ala Pro Phe Ala Met Thr Gly Glu Lys Val Asp Leu Asn Glu Glu
        195                 200                 205

Glu Thr Ile Leu Ile Ile Arg Arg Leu His Lys Val Leu Arg Pro Phe
    210                 215                 220

Leu Leu Arg Arg Leu Lys Lys Glu Val Glu Ala Gln Leu Pro Glu Lys
225                 230                 235                 240

Val Glu Tyr Val Ile Lys Cys Asp Met Ser Ala Leu Gln Arg Val Leu
                245                 250                 255

Tyr Arg His Met Gln Ala Lys Gly Val Leu Leu Thr Asp Gly Ser Glu
            260                 265                 270
```

```
Lys Asp Lys Lys Gly Lys Gly Gly Thr Lys Thr Leu Met Asn Thr Ile
            275                 280                 285

Met Gln Leu Arg Lys Ile Cys Asn His Pro Tyr Met Phe Gln His Ile
        290                 295                 300

Glu Glu Ser Phe Ser Glu His Leu Gly Phe Thr Gly Gly Ile Val Gln
305                 310                 315                 320

Gly Leu Asp Leu Tyr Arg Ala Ser Gly Lys Phe Glu Leu Leu Asp Arg
                325                 330                 335

Ile Leu Pro Lys Leu Arg Ala Thr Asn His Lys Val Leu Leu Phe Cys
            340                 345                 350

Gln Met Thr Ser Leu Met Thr Ile Met Glu Asp Tyr Phe Ala Tyr Arg
        355                 360                 365

Gly Phe Lys Tyr Leu Arg Leu Asp Gly Thr Thr Lys Ala Glu Asp Arg
    370                 375                 380

Gly Met Leu Leu Lys Thr Phe Asn Glu Pro Gly Ser Glu Tyr Phe Ile
385                 390                 395                 400

Phe Leu Leu Ser Thr Arg Ala Gly Gly Leu Gly Leu Asn Leu Gln Ser
                405                 410                 415

Ala Asp Thr Val Ile Ile Phe Asp Ser Asp Trp Asn Pro His Gln Asp
            420                 425                 430

Leu Gln Ala Gln Asp Arg Ala His Arg Ile Gly Gln Gln Asn Glu Val
        435                 440                 445

Arg Val Leu Arg Leu Cys Thr Val Asn Ser Val Glu Glu Lys Ile Leu
    450                 455                 460

Ala Ala Ala Lys Tyr Lys Leu Asn Val Asp Gln Lys Val Ile Gln Ala
465                 470                 475                 480

Gly Met Phe Asp Gln Lys
                485

<210> SEQ ID NO 71
<211> LENGTH: 507
<212> TYPE: PRT
<213> ORGANISM: Danio rerio

<400> SEQUENCE: 71

Val Val Val Asp Pro Val Leu Ser Lys Val Leu Arg Pro His Gln Arg
1               5                   10                  15

Glu Gly Val Lys Phe Leu Trp Asp Cys Val Thr Gly Arg Arg Ile Glu
                20                  25                  30

Asn Ser Tyr Gly Cys Ile Met Ala Asp Glu Met Gly Leu Gly Lys Thr
            35                  40                  45

Leu Gln Cys Ile Thr Leu Ile Trp Thr Leu Leu Lys Gln Ser Pro Asp
    50                  55                  60

Cys Lys Pro Glu Ile Asp Lys Val Ile Val Ser Pro Ser Ser Leu
65                  70                  75                  80

Val Arg Asn Trp Tyr Asn Glu Val Gly Lys Trp Leu Gly Gly Arg Val
                85                  90                  95

Gln Pro Val Ala Ile Asp Gly Gly Ser Lys Asp Glu Ile Asp Ser Lys
            100                 105                 110

Leu Val Asn Phe Ile Ser Gln Gln Gly Met Arg Ile Pro Thr Pro Ile
    115                 120                 125

Leu Ile Ile Ser Tyr Glu Thr Phe Arg Leu His Ala Glu Val Leu His
130                 135                 140

Lys Gly Lys Val Gly Leu Val Ile Cys Asp Glu Gly His Arg Leu Lys
145                 150                 155                 160
```

```
Asn Ser Asp Asn Gln Thr Tyr Leu Ala Leu Asn Ser Met Asn Ala Gln
                165                 170                 175

Arg Arg Val Leu Ile Ser Gly Thr Pro Ile Gln Asn Asp Leu Leu Glu
            180                 185                 190

Tyr Phe Ser Leu Val His Phe Val Asn Ser Gly Ile Leu Gly Thr Ala
        195                 200                 205

Gln Glu Phe Lys Lys Arg Phe Glu Ile Pro Ile Leu Lys Gly Arg Asp
    210                 215                 220

Ala Asp Ala Ser Asp Lys Asp Arg Ala Ala Gly Glu Gln Lys Leu Gln
225                 230                 235                 240

Glu Leu Ile Ser Ile Val Asn Arg Cys Leu Ile Arg Arg Thr Ser Asp
                245                 250                 255

Ile Leu Ser Lys Tyr Leu Pro Val Lys Ile Glu Gln Val Val Cys Cys
            260                 265                 270

Asn Leu Thr Pro Leu Gln Lys Glu Leu Tyr Lys Leu Phe Leu Lys Gln
        275                 280                 285

Ala Lys Pro Val Glu Ser Leu Gln Thr Gly Lys Ile Ser Val Ser Ser
    290                 295                 300

Leu Ser Ser Ile Thr Ser Leu Lys Lys Leu Cys Asn His Pro Ala Leu
305                 310                 315                 320

Ile Tyr Glu Lys Cys Leu Thr Gly Glu Gly Phe Asp Gly Ala Leu
                325                 330                 335

Asp Leu Phe Pro Gln Asn Tyr Ser Thr Lys Ala Val Glu Pro Gln Leu
            340                 345                 350

Ser Gly Lys Met Leu Val Leu Asp Tyr Ile Leu Ala Met Thr Arg Thr
        355                 360                 365

Thr Thr Ser Asp Lys Val Val Leu Val Ser Asn Tyr Thr Gln Thr Leu
    370                 375                 380

Asp Leu Phe Glu Lys Leu Cys Arg Asn Arg Arg Tyr Leu Tyr Val Arg
385                 390                 395                 400

Leu Asp Gly Thr Met Ser Ile Lys Lys Arg Ala Lys Ile Val Glu Arg
                405                 410                 415

Phe Asn Asn Pro Ser Ser Pro Glu Phe Ile Phe Met Leu Ser Ser Lys
            420                 425                 430

Ala Gly Gly Cys Gly Leu Asn Leu Ile Gly Ala Asn Arg Leu Val Met
        435                 440                 445

Phe Asp Pro Asp Trp Asn Pro Ala Asn Asp Glu Gln Ala Met Ala Arg
    450                 455                 460

Val Trp Arg Asp Gly Gln Lys Lys Thr Cys Tyr Ile Tyr Arg Leu Ser
465                 470                 475                 480

Thr Gly Thr Ile Glu Glu Lys Ile Leu Gln Arg Gln Ala His Lys Lys
                485                 490                 495

Ala Leu Ser Ser Cys Val Val Asp Glu Glu Gln
            500                 505

<210> SEQ ID NO 72
<211> LENGTH: 452
<212> TYPE: PRT
<213> ORGANISM: sulfolobus

<400> SEQUENCE: 72

Gln Leu Leu Glu Asp Tyr Asn Ile Lys Ala Asn Leu Arg Pro Tyr Gln
1               5                   10                  15

Ile Lys Gly Phe Ser Trp Met Arg Phe Met Asn Lys Leu Gly Phe Gly
```

```
                20              25              30
Ile Cys Leu Ala Asp Asp Met Gly Leu Gly Lys Thr Leu Gln Thr Ile
            35                  40                  45
Ala Val Phe Ser Asp Ala Lys Lys Glu Asn Glu Leu Thr Pro Ser Leu
        50                  55                  60
Val Ile Cys Pro Leu Ser Val Leu Lys Asn Trp Glu Glu Glu Leu Ser
65                  70                  75                  80
Lys Phe Ala Pro His Leu Arg Phe Ala Val Phe His Glu Asp Arg Ser
                85                  90                  95
Lys Ile Lys Leu Glu Asp Tyr Asp Ile Ile Leu Thr Thr Tyr Ala Val
            100                 105                 110
Leu Leu Arg Asp Thr Arg Leu Lys Glu Val Glu Trp Lys Tyr Ile Val
        115                 120                 125
Ile Asp Glu Ala Gln Asn Ile Lys Asn Pro Gln Thr Lys Ile Phe Lys
    130                 135                 140
Ala Val Lys Glu Leu Lys Ser Lys Tyr Arg Ile Ala Leu Thr Gly Thr
145                 150                 155                 160
Pro Ile Glu Asn Lys Val Asp Asp Leu Trp Ser Ile Met Thr Phe Leu
                165                 170                 175
Asn Pro Gly Leu Leu Gly Ser Tyr Ser Glu Phe Lys Ser Lys Phe Ala
            180                 185                 190
Thr Pro Ile Lys Lys Gly Asp Asn Met Ala Lys Glu Glu Leu Lys Ala
        195                 200                 205
Ile Ile Ser Pro Phe Ile Leu Arg Arg Thr Lys Tyr Asp Lys Ala Ile
    210                 215                 220
Ile Asn Asp Leu Pro Asp Lys Ile Glu Thr Asn Val Tyr Cys Asn Leu
225                 230                 235                 240
Thr Pro Glu Gln Ala Ala Met Tyr Lys Ala Glu Val Glu Asn Leu Phe
                245                 250                 255
Asn Asn Ile Asp Ser Val Thr Gly Ile Lys Arg Lys Gly Met Ile Leu
            260                 265                 270
Ser Thr Leu Leu Lys Leu Lys Gln Ile Val Asp His Pro Ala Leu Leu
        275                 280                 285
Lys Gly Gly Glu Gln Ser Val Arg Arg Ser Gly Lys Met Ile Arg Thr
    290                 295                 300
Met Glu Ile Ile Glu Glu Ala Leu Asp Glu Gly Asp Lys Ile Ala Ile
305                 310                 315                 320
Phe Thr Gln Phe Val Asp Met Gly Lys Ile Ile Arg Asn Ile Ile Glu
                325                 330                 335
Lys Glu Leu Asn Thr Glu Val Pro Phe Leu Tyr Gly Glu Leu Ser Lys
            340                 345                 350
Lys Glu Arg Asp Asp Ile Ile Ser Lys Phe Gln Asn Asn Pro Ser Val
        355                 360                 365
Lys Phe Ile Val Leu Ser Val Lys Ala Gly Gly Phe Gly Ile Asn Leu
    370                 375                 380
Thr Ser Ala Asn Arg Val Ile His Phe Asp Arg Trp Trp Asn Pro Ala
385                 390                 395                 400
Val Glu Asp Gln Ala Thr Asp Arg Val Tyr Arg Ile Gly Gln Thr Arg
                405                 410                 415
Asn Val Ile Val His Lys Leu Ile Ser Val Gly Thr Leu Glu Glu Lys
            420                 425                 430
Ile Asp Gln Leu Leu Ala Phe Lys Arg Ser Leu Phe Lys Asp Ile Ile
        435                 440                 445
```

Ser Ser Gly Asp
    450

<210> SEQ ID NO 73
<211> LENGTH: 511
<212> TYPE: PRT
<213> ORGANISM: Saccharomyces cerevisiae

<400> SEQUENCE: 73

Asn Ser Lys Ile Leu Pro Gln Tyr Ser Ser Asn Tyr Thr Ser Gln Arg
1               5                   10                  15

Pro Arg Phe Glu Lys Leu Ser Val Gln Pro Pro Phe Ile Lys Gly Gly
            20                  25                  30

Glu Leu Arg Asp Phe Gln Leu Thr Gly Ile Asn Trp Met Ala Phe Leu
        35                  40                  45

Trp Ser Lys Gly Asp Asn Gly Ile Leu Ala Asp Glu Met Gly Leu Gly
    50                  55                  60

Lys Thr Val Gln Thr Val Ala Phe Ile Ser Trp Leu Ile Phe Ala Arg
65                  70                  75                  80

Arg Gln Asn Gly Pro His Ile Ile Val Val Pro Leu Ser Thr Met Pro
                85                  90                  95

Ala Trp Leu Asp Thr Phe Glu Lys Trp Ala Pro Asp Leu Asn Cys Ile
            100                 105                 110

Cys Tyr Met Gly Asn Gln Lys Ser Arg Asp Thr Ile Arg Glu Tyr Glu
        115                 120                 125

Phe Tyr Thr Asn Pro Arg Ala Lys Gly Lys Lys Thr Met Lys Phe Asn
    130                 135                 140

Val Leu Leu Thr Thr Tyr Glu Tyr Ile Leu Lys Asp Arg Ala Glu Leu
145                 150                 155                 160

Gly Ser Ile Lys Trp Gln Phe Met Ala Val Asp Glu Ala His Arg Leu
                165                 170                 175

Lys Asn Ala Glu Ser Ser Leu Tyr Glu Ser Leu Asn Ser Phe Lys Val
            180                 185                 190

Ala Asn Arg Met Leu Ile Thr Gly Thr Pro Leu Gln Asn Asn Ile Lys
        195                 200                 205

Glu Leu Leu Ala Ala Leu Val Asn Phe Leu Met Pro Gly Arg Phe Thr
    210                 215                 220

Ile Asp Gln Glu Ile Asp Phe Glu Asn Gln Asp Glu Glu Gln Glu Glu
225                 230                 235                 240

Tyr Ile His Asp Leu His Arg Arg Ile Gln Pro Phe Ile Leu Arg Arg
                245                 250                 255

Leu Lys Lys Asp Val Glu Lys Ser Leu Pro Ser Lys Thr Glu Arg Ile
            260                 265                 270

Leu Arg Val Glu Leu Ser Asp Val Gln Thr Glu Tyr Tyr Lys Asn Ile
        275                 280                 285

Leu Thr Lys Asn Tyr Ser Ala Leu Thr Ala Gly Ala Lys Gly Gly His
    290                 295                 300

Phe Ser Leu Leu Asn Ile Met Asn Glu Leu Lys Lys Ala Ser Asn His
305                 310                 315                 320

Pro Tyr Leu Phe Asp Asn Ala Glu Glu Arg Val Leu Gln Lys Phe Gly
                325                 330                 335

Asp Gly Lys Met Thr Arg Glu Asn Val Leu Arg Gly Leu Ile Met Ser
            340                 345                 350

Ser Gly Lys Met Val Leu Leu Asp Gln Leu Leu Thr Arg Leu Lys Lys

```
                355                360                365
Asp Gly His Arg Val Leu Ile Phe Ser Gln Met Val Arg Met Leu Asp
        370                375                380

Ile Leu Gly Asp Tyr Leu Ser Ile Lys Gly Ile Asn Phe Gln Arg Leu
385                390                395                400

Asp Gly Thr Val Pro Ser Ala Gln Arg Arg Ile Ser Ile Asp His Phe
                405                410                415

Asn Ser Pro Asp Ser Asn Asp Phe Val Phe Leu Leu Ser Thr Arg Ala
            420                425                430

Gly Gly Leu Gly Ile Asn Leu Met Thr Ala Asp Thr Val Val Ile Phe
        435                440                445

Asp Ser Asp Trp Asn Pro Gln Ala Asp Leu Gln Ala Met Ala Arg Ala
    450                455                460

His Arg Ile Gly Gln Lys Asn His Val Met Val Tyr Arg Leu Val Ser
465                470                475                480

Lys Asp Thr Val Glu Glu Val Leu Glu Arg Ala Lys Lys Met Ile
                485                490                495

Leu Glu Tyr Ala Ile Ile Ser Leu Gly Val Thr Asp Gly Asn Lys
            500                505                510

<210> SEQ ID NO 74
<211> LENGTH: 291
<212> TYPE: DNA
<213> ORGANISM: Homo sapiens

<400> SEQUENCE: 74
gcttctgggc ctcggcggcc atgcggttgg cgtggctgag ctggatctcc atctcattga        60
ggtctccttc catcttcttc ttcaccctca gggcctcgtt gcggctgcgt gctctgcgtc       120
cagggaggtc tgcagcgagt ccaccacccg caggtggttg cgttggcctg ttccatctcc       180
tcgtccttct ctgccagctt ccgctcgatc tctgccttga tctggttgaa ctccagctgg       240
gcccggagga tcttgccctc ctcctgcttt cggaccttct ccagctcatg g                291

<210> SEQ ID NO 75
<211> LENGTH: 272
<212> TYPE: DNA
<213> ORGANISM: Mus musculus

<400> SEQUENCE: 75
ccttcaggtc atcattggca cggacagcat catccagctg gatttgagtg tcctgaggat        60
cagaaaaatg agtggcctca ttgcggctgc gtgtctccgc atccagggag gtctgcaggg       120
agtccaccat ccgcaggtgg ttgcgcttgg cctgctccat ctcctcatcc ttctctgcca       180
gcttcctttc aatctcttgc cttgatctgg ttgaactcta gctgggcgcg gaggatcttg       240
ccctcctcgt gctccaggga ggcctggaaa gg                                     272
```

ROLE OF A CLUSTER OF LONG NONCODING RNA TRANSCRIPTS IN PROTECTING THE HEART FROM PATHOLOGICAL HYPERTROPHY

CROSS-REFERENCE TO RELATED APPLICATIONS

This application claims benefit of priority to U.S. Provisional Patent Application No. 62/068,041 to Chang, entitled "The Role Of A Cluster Of Long Noncoding RNA Transcripts In Protecting The Heart From Pathological Hypertrophy," filed Oct. 24, 2014. The entire contents and disclosure of this patent application are incorporated herein by reference in its entirety.

GOVERNMENT INTEREST STATEMENT

This invention was made with the United States government support under grant Nos. HL118087 and HL121197 awarded by the National Institutes of Health (NIH). The government has certain rights in the invention.

BACKGROUND

Field of the Invention

The present invention relates to generally to a method and products for treating pathological hypertrophy.

Background of the Invention

Cardiac hypertrophy and failure are characterized by transcriptional reprogramming of gene expression. The role of long noncoding RNA (lncRNA) in adult hearts is unknown.

SUMMARY

According to first broad aspect, the present invention provides composition comprising a nucleic acid encoding a modified myosin heavy-chain-associated RNA transcript, wherein the modified myosin heavy-chain-associated RNA transcript inhibits Brg1's genomic targeting and gene regulation function in a subject to whom the composition is administered.

According to a second broad aspect, the present invention provides an organism comprising a transgene comprising a promoter and a nucleic acid encoding a modified myosin heavy-chain-associated RNA transcript, wherein the promoter regulates an expression of the nucleic acid to produce the modified myosin heavy-chain-associated RNA transcript in the organism, and wherein the modified myosin heavy-chain-associated RNA transcript inhibits Brg1's genomic targeting and gene regulation function in the organism.

According to a third broad aspect, the present invention provides a method comprising: administering to a subject in need of a composition comprising a nucleic acid encoding a modified myosin heavy-chain-associated RNA transcript to express the modified myosin heavy-chain-associated RNA transcript in the subject, wherein the modified myosin heavy-chain-associated RNA transcript inhibits Brg1's genomic targeting and gene regulation function in the subject.

According to a fourth broad aspect, the present invention provides a treatment delivery apparatus comprising a device and at least one dosage of a composition contained in the device, wherein the composition comprises a nucleic acid encoding a modified myosin heavy-chain-associated RNA transcript, and wherein the modified myosin heavy-chain-associated RNA transcript inhibits Brg1's genomic targeting and gene regulation function in a subject to whom the composition is administered.

According to a fifth broad aspect, the present invention provides a composition comprising a modified myosin heavy-chain-associated RNA transcript, wherein the modified myosin heavy-chain-associated RNA transcript inhibits Brg1's genomic targeting and gene regulation function in a subject having the modified myosin heavy-chain-associated RNA transcript.

According to a sixth broad aspect, the present invention provides a method comprising: administering to a subject in need thereof a composition comprising a modified myosin heavy-chain-associated RNA transcript, wherein the modified myosin heavy-chain-associated RNA transcript inhibits Brg1's genomic targeting and gene regulation function in the subject.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

FIG. 1 is a diagram showing a model of developmentally activated and stress-induced assembly of BAF/HDAC/PARP complexes on the α-MHC promoter, and BAF/PARP complex on the β-MHC promoter according to an exemplary embodiment of the present invention.

FIG. 2 is a schematic illustration of Mhrt RNAs originating from the intergenic region between Myh6 and Myh7 and transcribed into Myh7. Myh7 exons and introns are indicated. "m" refers to mid region of the RNAs.

FIG. 3 is a graph showing quantitative PCR with reverse transcription (RT-qPCR) of Mhrt RNAs using primers targeting common regions of Mhrt RNAs in tissues from 2-month-old mice.

FIG. 4 is a graph showing RT-qPCR of Mhrt, Myh6 and Myh7 in mouse hearts at different ages. Mhrt and Myh6/Myh7 ratio of embryonic day (E) 11 hearts are set as 1. "P" refers to postnatal day.

FIG. 5 shows RNA in situ analysis of Mhrt (dark spots) in adult hearts.

FIG. 6 is a graph showing RT-qPCR of nuclear/cytoplasmic RNA in adult hearts. TfIIb (also known as Gtf2b), Hprt1 and 28S rRNA are primarily cytoplasmic RNAs; Neat1, nuclear lncRNA. TfIIb ratio is set as 1.

FIG. 7 is a graph showing ribosome profiling: ribosome density on coding RNAs and lncRNAs. P values: Student's t-test. Error bars show standard error of the mean (s.e.m.).

FIG. 8 is an image of RNA in situ analysis of Mhrt (dark spots) in a mouse E12 heart.

FIG. 9 is a graph of codon substitution frequency (CSF) scores of TfIIb and Hprt1 mRNA, as well as full-length Mhrt species.

FIG. 10 is an image of in vitro translation of control Mhrt species (709, 779, 826, 828, 857, 1147) and luciferase (Luc). Arrow points to the protein product of luciferase.

FIG. 11 is an image of Biotin-labelling of Mhrt species (709, 779, 826, 828, 857, 1147) and luciferase in the in vitro translation reactions. Arrow points to the RNA product of luciferase.

FIG. 12 shows ribosome profiling relative to whole transcriptome RNA sequencing. x-axis: genomic position at the human GAPDH and the murine Myh7 loci. y-axis: mapped reads.

FIG. 13 is an image of scatter plot of RNA in fragments per kilobase per million reads (FPKM).

FIG. 14 is a graph showing quantification of cardiac Mhrt RNAs 2-42 days (d) after TAC operation.

FIG. 15 is an image of result of RT-PCR of Mhrt RNAs in adult heart ventricles. Primers (F1 and R1 used in FIG. 2) target Mhrt common regions. Size controls 779, 826 and 709 are PCR products of recombinant Mhrt779, Mhrt826 and Mhrt709, respectively.

FIG. 16 is an image of Northern blot of Mhrt RNAs in adult heart ventricles. The probe targets common regions of Mhrt RNAs. "Negative" refers to control RNA from 293T cells. Size control: 826 is recombinant Mhrt826; 643 (not a distinct Mhrt species) contains the 5' common region of Mhrt.

FIG. 17 is a set of graphs showing quantification of Mhrt779 in control or Tg779 mice with or without doxycycline (Dox) or TAC operation. Mhrt779-specific PCR primers are used. "Ctrl" refers to control mice.

FIG. 18 is a set of images showing ventricle/body-weight ratio of hearts 6 weeks (wk) after TAC. Scale bars=1 mm.

FIG. 19 is a graph of a result of quantification of cardiomyocyte size in control and Tg779 mice 6 weeks after TAC by wheat germ agglutinin staining.

FIG. 20 is a set of images showing trichrome staining in control and Tg779 hearts 6 weeks after TAC. Red indicates cardiomyocytes; blue indicates fibrosis. Scale bars=20 μm.

FIG. 21 is a graph of results of echocardiographic measurement of left ventricular fractional shortening 6 weeks after TAC.

FIG. 22 is a graph of results of echocardiographic measurement of internal dimensions at end-diastole (LVIDd) and end-systole (LVIDs) weeks after TAC. P values: Student's t-test. Error bars show s.e.m.

FIG. 23 shows quantification of cardiac Myh6/Myh7 ratio 2-42 days after sham or TAC operation.

FIG. 24 shows Northern blot analysis of Mhrt, Myh6 and Myh7. Negative: control RNA from 293T cells. Size control: 826 is recombinant Mhrt826; 643 (not a distinct Mhrt species) contains the 5' common region of Mhrt. Heart: adult heart ventricles.

FIG. 25 shows un-cropped northern blots of Mhrt, Myh6 and Myh7.

FIG. 26 shows RNA in situ hybridization of Mhrt779 of adult heart ventricles.

FIG. 27 shows quantification of TfIIb, Hprt1, 28S rRNA, Neat1 and Mhrt779 in the nuclear and cytoplasmic fraction of adult heart ventricle extracts.

FIG. 28 shows wheat germ agglutinin (WGA) immunostaining 6 weeks after the sham or TAC operation.

FIG. 29 shows time course of fractional shortening (FS) in control and Tg779 mice.

FIG. 30 shows quantification of Anf, Bnp, Serca2 and Tgfb1 in control and Tg779 mice 2 weeks after sham or TAC operation.

FIG. 31 shows Experimental design for treatment study and time course of left ventricular fractional shortening changes.

FIG. 32 shows fractional shortening of the left ventricle (LV) 8 weeks after the operation.

FIG. 33 shows ventricular weight/body weight ratio of hearts harvested 8 weeks after sham or TAC operation. P values: Student's t-test. Error bars show s.e.m.

FIGS. 34, 35, 36, 37, 38, 39, 40, 41 and 42 are a set of graphs and schematics showing Mhrt complexes with Brg1 through the helicase domain according to an exemplary embodiment of the present invention.

FIG. 43 shows a sequence alignment of Mhrt promoter loci from mouse, human and rat.

FIG. 44 shows a ChIP-qPCR analysis of Mhrt promoter using antibodies against Pol II in tissues of adult mice.

FIG. 45 shows a ChIP-qPCR analysis of Mhrt promoter using antibodies against H3K4me3 in tissues of adult mice.

FIG. 46 shows a ChIP-qPCR analysis of Mhrt promoter using antibodies against H3K36me3 in tissues of adult mice.

FIG. 47 shows RT-qPCR quantification of Mhrt in control and Brg1-null hearts after 7 days of TAC. Ctrl, control. Brg1-null, Tnnt2-rtTA;Tre-Cre;Brg1$^{fl/fl}$.

FIG. 48 shows luciferase reporter assay of Mhrt promoter in SW13 cells. Ctrl: dimethylsulphoxide (DMSO). PJ-34, PARP inhibitor; TSA, trichostatin (HDAC inhibitor).

FIG. 49 shows ChIP analysis of BRG1, HDAC2, HDAC9 and PARP1 in SW13 cells. The cells were transfected with episomal Mhrt promoter cloned in pREP4.

FIG. 50 show deletional analyses of the Mhrt promoter in luciferase reporter assays in SW13 cells. Luciferase activity of full-length Mhrt promoter was set up as 1. P values: Student's t-test. Error bars show s.e.m.

FIG. 51 shows qPCR analysis of Mhrt779, Myh6 and Myh7 in mice without TAC operation. Expression levels were normalized to TfIIb, and the control is set as 1. Ctrl, control mice.

FIG. 52 shows RNA quantification of Mhrt in SW13 cells transfected with Vector (pAdd2), HOTAIR (pAdd2-HOTAIR) or Mhrt (pAdd2-Mhrt779).

FIG. 53 shows RNA quantification of HOTAIR in SW13 cells transfected with Vector (pAdd2), HOTAIR (pAdd2-HOTAIR) or Mhrt (pAdd2-Mhrt779).

FIG. 54 shows RNA quantification of Myh6 in SW13 cells relative to GAPDH.

FIG. 55 shows RNA quantification of Myh7 in SW13 cells relative to GAPDH.

FIG. 56 shows Western blot analysis of Myh6 in SW13 cells.

FIG. 57 shows Western blot analysis of Myh7 in SW13 cells. Constructs containing Myh6- and Myh7-coding sequences were tagged with Flag and co-transfected with vector, HOTAIR or Mhrt779. GAPDH was used as the loading control. Flag-D1 was used as a positive control for the Flag antibody.

FIG. 58 shows protein quantification of Myh6 in control and transfected SW13 cells relative to GAPDH.

FIG. 59 shows protein quantification of Myh7 in control and transfected SW13 cells relative to GAPDH.

FIG. 60 shows a luciferase reporter assay of Mhy6 and Myh7 promoters in SW13 cells transfected with vector (pAdd2) or Mhrt (pAdd2-Mhrt779).

FIG. 61 shows immunostaining of Brg1 in P1 heart. Red: Brg1. Green: WGA. Blue: DAPI. Ctrl, control. Scale bar=50 μm.

FIG. 62 shows RNA-IP of Mhrt in P1 hearts using antibodies against Ezh2 and Suz12. Right panels show immunostaining of Ezh2 and Suz12 in P1 hearts.

FIG. 63 shows quantification of Opn mRNA in control and Brg1-null (Tnnt2-rtTA;Tre-Cre;Brg1$^{fl/fl}$) mice after sham or TAC operation.

FIG. 64 shows ChIP of Brg1 on Opn proximal promoter in control and transgenic (Tg779) mice after sham or TAC operation.

FIG. 65 shows quantification of Opn in control and transgenic (Tg779) mice after sham or TAC operation.

FIG. 66 shows a qPCR analysis of Brg1 expression in hearts without TAC operation. Ctrl: control mice.

FIGS. 67, 68, 69 and 70 show immunostaining of Brg1 (red) in adult heart ventricles 2 weeks after sham or TAC operation. Green: WGA. Blue: DAPI. Scale bars=50 µm.

FIG. 71 shows a Western blot analysis of Brg1 and Coomassie staining of total proteins in control or Tg779 hearts after 2 weeks of sham or TAC operation.

FIG. 72 shows a quantification of Myh6 and Myh7 in control (Ctrl) and Tg779 hearts after 2 weeks of sham or TAC operation. P values: Student's t-test. Error bars show s.e.m.

FIGS. 73, 74, 75, 76, 77, 78, 79, 80, 81, 82, 83, 84, 85 and 86 are a set of images and graphs showing that Mhrt inhibits chromatin targeting and gene regulation by Brg1 according to an exemplary embodiment of the present invention.

FIG. 87 is Mountain plot of Mhrt779 predicted by RNA fold.

FIG. 88 is a diagram showing MFE secondary structure of segments Mhrt-A, -B and -C.

FIG. 89 shows EMSA of Mhrt-A, -B and -C and Brg1 helicase D1D2. MBP: maltose binding protein.

FIG. 90 is a graph showing binding affinity of Mhrt-A, -B and -C to Brg1 D1D2 determined by EMSA.

FIG. 91 is a schematic illustration of a treatment delivery apparatus according to one embodiment of the present invention.

FIG. 92 is a diagram illustrating sequence alignment and motif analysis according to an exemplary embodiment of the present invention.

FIG. 93 is a Coomassie blue staining of purified MBP-tagged Brg1 helicase domains. Bovine serum albumin (BSA) was loaded as a control.

FIG. 94 is an EMSA assay of naked Myh6 promoter (2426 to 1170) with helicase domains of Brg1.

FIG. 95 is a ChIP analysis of Brg1 on chromatinized (episomal) and naked Myh6 promoter in SW13 cells.

FIG. 96 is a luciferase reporter analysis of Brg1 on chromatinized (episomal) and naked Myh6 promoter in SW13 cells.

FIG. 97 is an analysis of the luciferase reporter of helicase-deficient Brg1 on chromatinized (episomal) Myh6 promoter in SW13 cells.

FIG. 98 shows assembly of nucleosomes on the Mhrt promoter (a3/4).

FIG. 99 shows an amylose pull-down assay: amylose is used to pull down the chromatinized Mhrt promoter that is incubated with various doses of MBP and MBP-Brg1 D1D2.

FIG. 100 shows sequence alignment of human MHRT and mouse Mhrt779.

FIG. 101 shows predicted secondary structure of mouse Mhrt779 and human MHRT, using minimal free energy (MFE) calculation of RNAfold WebServer.

FIG. 102 shows Demography of human subjects whose tissues were used for RT-qPCR analysis.

FIG. 103 is an image of haematoxylin section of E10.5 compact myocardium.

FIG. 104 is an image of haematoxylin section of E10.5 compact myocardium.

FIG. 105 is an image showing BrdU immunostaining of E10.5 compact myocardium.

FIG. 106 is an image showing BrdU immunostaining of E10.5 compact myocardium.

FIG. 107 is a graph showing BrdU incorporation quantification.

FIG. 108 is an image showing Bmp10 in situ hybridization of E10.5 hearts.

FIG. 109 is an image showing Bmp10 in situ hybridization of E10.5 hearts.

FIG. 110 is an image showing $p57^{kip2}$ immunostaining of E10.5 hearts.

FIG. 111 is an image showing $p57^{kip2}$ immunostaining of E10.5 hearts.

FIG. 112 is a graph showing p57kip2 quantification.

FIG. 113 is an electron micrograph (cropped from ×35,000 magnification) of the compact myocardium of E10.5 embryos.

FIG. 114 is an electron micrograph (cropped from ×35,000 magnification) of the compact myocardium of E10.5 embryos.

FIG. 115 shows graphs illustrating quantitative RT-PCR of ventricular α-MHC and β-MHC at E10.5 and E11.5.

FIG. 116 is a graph illustrating sequence alignment of the α-MHC locus from mouse, human and rat.

FIG. 117 is an image showing PCR analyses of Brg1-immunoprecipitated chromatin from E11.5 hearts.

FIG. 118 is an image showing luciferase reporter assay of the proximal α-MHC promoter (−462 to +192) in SW13 cells. "TSA" refers to trichostatin A.

FIG. 119 is a graph showing sequence alignment of the β-MHC locus from mouse, human and rat.

FIG. 120 is an image showing PCR analysis of Brg1-immunoprecipitated chromatin from E11.5 hearts.

FIG. 121 is a graph illustrating Luciferase reporter assays of the β-MHC proximal promoter (−835 to +222) in SW13 cells.

FIG. 122 is a set of images illustrating immunostaining (cropped from ×200 magnification) of HDAC1, HDAC2, HDAC3, HDAC5, HDAC6 and HDAC9 in E11.5 hearts.

FIG. 123 is an image showing co-immunoprecipitation of Brg1 with HDAC1, HDAC2 and HDAC9 in E11.5 hearts.

FIG. 124 is a set of two graphs showing quantitative RT-PCR of α- and β-MHC of cultured embryos treated with dimethylsulphoxide (DMSO) or TSA.

FIG. 125 is a graph showing cardiomyocyte size quantification. "Ctrl" refers to control. "Mut" refers to Tnnt2-rtTA; Tre-cre;Brg1f/f.

FIGS. 128, 129 and 130 are a set of images of Brg1 immunostaining (cropped from ×200 magnification) in ventricular myocardium of doxycycline-treated control and Tnnt2-rtTA;Tre-cre;Brg1$^{f/f}$ mice 1 week after sham/TAC operation.

FIG. 131 is an image of Brg1 immunoblot of cardiac nuclear extracts from wild-type mice 2 weeks after TAC.

FIG. 132 is a graph of quantitative RT-PCR of Brg1 mRNA in wild-type mice 2 weeks after TAC.

FIG. 133 is an image of PCR of Brg1- and PARP1-immunoprecipitated chromatin from thymus and adult hearts 2 weeks after TAC.

FIG. 134 is a graph of luciferase reporter assays of α-MHC promoter in SW13 cells with PARP inhibition.

FIG. 135 is a graph of luciferase reporter assays of β-MHC promoter in SW13 cells with PARP inhibition.

FIG. 136 is an image of co-immunoprecipitation of Brg1, PARP1, HDAC2 and HDAC9 in TAC-treated adult hearts.

FIG. 137 is an image of co-immunoprecipitation of Brg1, PARP1, HDAC2 and HDAC9 in E11.5 hearts.

FIG. 138 is a graph of quantitative RT-PCR of α- and β-MHC of PJ-34-treated cultured embryos.

FIG. 139 is an image of PCR of PARP1-immunoprecipitated chromatin from E11.5 hearts.

FIG. 140 is an image of PCR of HDAC2-immunoprecipitated chromatin from adult hearts 2 weeks after TAC.

FIGS. 141, 142 and 143 are a set of graphs illustrating BRG1 activation in human cardiomyopathy according to an exemplary embodiment of the present invention.

DETAILED DESCRIPTION OF THE INVENTION

Definitions

Figure 126:
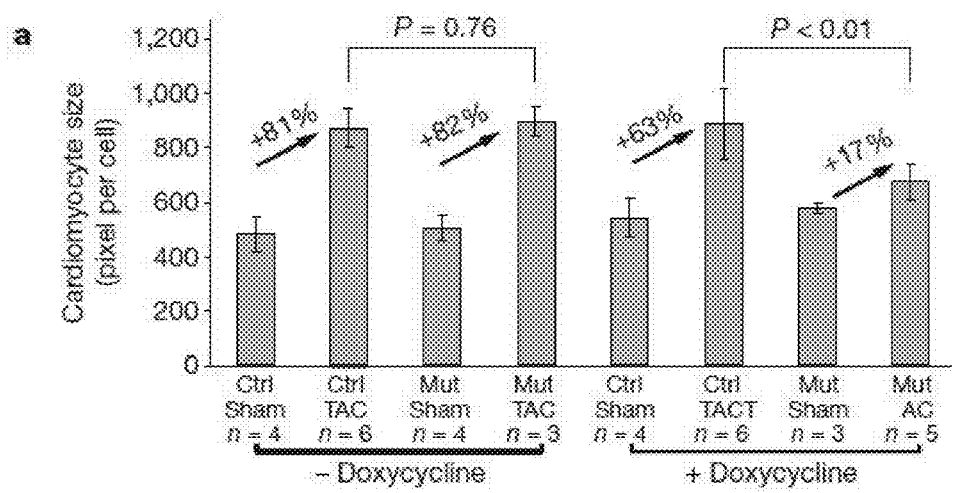
FIGS. 126 and 127 are graphs showing quantitative RT-PCR of α- and β-MHC in cardiac ventricles of doxycycline-treated control and Tnnt2-rtTA;Tre-cre;Brg1$^{f/f}$ mice 4 weeks after sham/TAC operation.

Where the definition of terms departs from the commonly used meaning of the term, applicant intends to utilize the definitions provided below, unless specifically indicated.

Unless defined otherwise, all technical and scientific terms used herein have the same meaning as is commonly understood to which the claimed subject matter belongs. In the event that there is a plurality of definitions for terms herein, those in this section prevail. All patents, patent applications, publications and published nucleotide and amino acid sequences (e.g., sequences available in GenBank or other databases) referred to herein are incorporated by reference. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

For purposes of the present invention, a value or property is "based" on a particular value, property, the satisfaction of a condition, or other factor, if that value is derived by performing a mathematical calculation or logical decision using that value, property or other factor.

For purposes of the present invention, directional terms such as "top," "bottom," "upper," "lower," "above," "below," "left," "right," "horizontal," "vertical," "up," "down," etc., are used merely for convenience in describing the various embodiments of the present invention. The embodiments of the present invention may be oriented in various ways. For example, the diagrams, apparatuses, etc., shown in the drawing figures may be flipped over, rotated by 90° in any direction, reversed, etc.

For purposes of the present invention, it should be noted that to provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

For purposes of the present invention, the term "animal" refers to humans as well as non-human animals. Preferably, the non-human animal is a mammal (e.g., a rodent, a mouse, a rat, a rabbit, a monkey, a dog, a cat, a primate, or a pig). An animal may be a domesticated animal. An animal may be a transgenic animal.

For purposes of the present invention, the term "antisense RNA" refers to a single-stranded RNA that is complementary to a messenger RNA (mRNA).

For purposes of the present invention, the term "carrier" refers to relatively nontoxic chemical compounds or agents that facilitate the incorporation of a compound of interest such as naltrexone, methylphenidate, etc., into organisms.

For purposes of the present invention, the term "complementary" and the term "complementarity" refer to polynucleotides (e.g., a sequence of nucleotides) related by the base-pairing rules. For example, a DNA sequence 5'-A-G-T-3' is complementary to a DNA sequence 3'-T-C-A-5' or a RNA sequence 3'-U-C-A-5'.

For purposes of the present invention, the term "comprising", the term "having", the term "including," and variations of these words are intended to be open-ended and mean that there may be additional elements other than the listed elements.

For purposes of the present invention, the term "comprising", the term "having", the term "including," and variations of these words are intended to be open-ended and mean that there may be additional elements other than the listed elements.

For purposes of the present invention, the term "dosage form," the term "form," and the term "unit dose" refer to a method of preparing pharmaceutical products in which individual doses of medications are prepared and delivered. Dosage forms typically involve a mixture of active drug components and nondrug components (excipients), along with other non-reusable material that may not be considered either ingredient or packaging.

For purposes of the present invention, the term "dosage" refers to the administering of a specific amount, number, and frequency of doses over a specified period of time. Dosage implies duration. A "dosage regimen" is a treatment plan for administering a drug over a period of time.

For purposes of the present invention, the term "dose" refers to a specified amount of medication taken at one time.

For purposes of the present invention, the term "drug" refers to a material that may have a biological effect on a cell, including but not limited to small organic molecules, inorganic compounds, polymers such as nucleic acids, peptides, saccharides, or other biologic materials, nanoparticles, etc.

For purposes of the present invention, the term "effective amount" and the term "effective dose" or grammatical variations thereof refer to an amount of an agent sufficient to produce one or more desired effects. The effective amount may be determined by a person skilled in the art using the guidance provided herein.

For purposes of the present invention, the term "expression cassette" refers to a recombinantly produced nucleic acid molecule that is capable of expressing a genetic sequence in a cell. An expression cassette typically includes a promoter (allowing transcription initiation), and a sequence encoding one or more proteins or RNAs. Optionally, the expression cassette may include transcriptional enhancers, non-coding sequences, splicing signals, transcription termination signals, and polyadenylation signals.

Optionally, the expression cassette may include a piece of a nucleic acid that is not translated into a protein. The nucleic acid can effect a change in the DNA or RNA sequence of the target cell.

For purposes of the present invention, the term "expression" refers to a process by which information from a gene or a fragment of DNA is gene expression.

For purposes of the present invention, the term "fragment" of a molecule such as a protein or a nucleic acid refers to a portion of an amino acid sequence of the protein or a portion of a nucleic acid of the nucleic acid.

For purposes of the present invention, the term "gene" refers to a nucleic acid (e.g., DNA or RNA) sequence that comprises coding sequences necessary for the production of an RNA or a polypeptide or its precursor. The term "portion," when used in reference to a gene, refers to fragments of that gene. The fragments may range in size from a few nucleotides to the entire gene sequence minus one nucleotide. Thus, "a nucleotide comprising at least a portion of a gene" may comprise fragments of the gene or the entire gene.

For purposes of the present invention, the term "gene expression" refers to a process by which information from a gene is used the synthesis of a functional gene product. A gene product is often a protein, but in a non-protein coding gene such as transfer RNA (tRNA) or small nuclear RNA (snRNA) gene, the product is a functional RNA.

For purposes of the present invention, the term "gene therapy" refers to the purposeful delivery of genetic material to cells for the purpose of treating disease or biomedical investigation and research. Gene therapy includes the delivery of a polynucleotide to a cell to express an exogenous nucleotide sequence, to inhibit, eliminate, augment, or alter expression of an endogenous nucleotide sequence, or to produce a specific physiological characteristic not naturally associated with the cell. In some cases, the polynucleotide itself, when delivered to a cell, can alter expression of a gene in the cell.

For purposes of the present invention, the term "incorporate" refers to insert a fragment of a first nucleic acid into a fragment of a second nucleic acid.

For purposes of the present invention, the term "individual" refers to an individual mammal, such as a human being.

For purposes of the present invention, the term "intraperitoneal injection" or the term "IP injection" refer to the injection of a substance into the peritoneum.

For purposes of the present invention, the term "medical therapy" refers to prophylactic, diagnostic and therapeutic regimens carried out in vivo or ex vivo on humans or other mammals.

For purposes of the present invention, the term "modified" and the term "mutant" when made in reference to a gene or to a gene product refer, respectively, to a gene or to a gene product which displays modifications in sequence and/or functional properties (i.e., altered characteristics) when compared to the wild-type gene or gene product.

For purposes of the present invention, the term "non-coding RNA" and the term "non-coding RNA transcript" refer to a functional RNA molecule that is not translated into a protein. The DNA sequence from which a non-coding RNA is transcribed can be called an "RNA gene". "Non-coding RNA" transcripts include highly abundant and functionally important RNAs such as (tRNAs) and ribosomal RNAs (rRNAs), as well as RNAs such as snoRNAs, micro-RNAs, siRNAs, snRNAs, exRNAs, and piRNAs and the long noncoding RNAs ("long ncRNA" or "lncRNA"). A "long non-protein coding transcript" is a noncoding RNA longer than about 200 nucleotides.

For purposes of the present invention, the term "oligonucleotide," the term "polynucleotide," the term "nucleotide," and the term "nucleic acid" refer to a molecule comprised of two or more deoxyribonucleotides or ribonucleotides, and usually more than ten. The exact size of an oligonucleotide will depend on many factors, which in turn depends on the ultimate function or use of the oligonucleotide. The oligonucleotide may be generated in any manner, including chemical synthesis, DNA replication, reverse transcription, or a combination thereof. When present in a DNA form, the oligonucleotide may be single-stranded (i.e., the sense strand) or double-stranded.

For purposes of the present invention, the term "operably linked" refers to place a first piece of a nucleic acidin a functional relationship with a second piece of a nucleic acid. For example, a promoter is operably linked to a coding sequence if the promoter affects the transcription or expression of the coding sequence. DNA operably linked to a promoter is under transcriptional initiation regulation of the promoter or in functional combination therewith.

For purposes of the present invention, the term "parenteral route" refers to the administration of a composition, such as a drug in a manner other than through the digestive tract. Parenteral routes include routes such as intravenous, intra-arterial, transdermal, intranasal, sub-lingual and intraosseous, etc. For example, intravenous is also known as I.V., which is giving directly into a vein with injection. As the drug directly goes into the systemic circulation, it reaches the site of action resulting in the onset the action.

For purposes of the present invention, the term "patient" and the term "subject" refer to an animal, which is the object of treatment, observation or experiment. By way of example only, a subject may be, but is not limited to, a mammal including, but not limited to, a human.

For purposes of the present invention, the term "pharmaceutical composition" refers to a product comprising one or more active ingredients, and one or more other components such as carriers, stabilizers, diluents, dispersing agents, suspending agents, thickening agents, and/or excipients, etc. A pharmaceutical composition includes enough of the active object compound to produce the desired effect upon the progress or condition of diseases and facilitates the administration of the active ingredients to an organism. Multiple techniques of administering the active ingredients exist in the art including, but not limited to: topical, ophthalmic, intraocular, periocular, intravenous, oral, aerosol, parenteral, and administration. By "pharmaceutically acceptable," it is meant the carrier, diluent or excipient must be compatible with the other ingredients of the formulation and not deleterious to the recipient thereof, i.e., the subject.

For purposes of the present invention, the term "pharmaceutical formulation" and the term "drug formulation" refer to a mixtures or a structure in which different chemical substances, including the active drug, are combined to form a final medicinal product, such as a sterile product, a capsule, a tablet, a powder, a granule, a solution, an emulsion, a topical preparation, a non-conventional product such as semi-solid or sustained-release preparations, liquid, etc. Pharmaceutical formulation is prepared according to a specific procedure, a "formula." The drug formed varies by the route of administration. For example, oral drugs are normally taken as tablet or capsules.

For purposes of the present invention, the term "pharmaceutically acceptable" refers to a compound or drug approved or approvable by a regulatory agency of a federal or a state government, listed or listable in the U.S. Pharmacopeia or in other generally recognized pharmacopeia for use in mammals, including humans.

For purposes of the present invention, the term "pharmaceutically acceptable carrier" refers to a carrier that comprises pharmaceutically acceptable materials. Pharmaceutically acceptable carriers include, but are not limited to saline solutions and buffered solutions. Pharmaceutically acceptable carriers are described for example in Gennaro, Alfonso, Ed., Remington's Pharmaceutical Sciences, 18th Edition 1990. Mack Publishing Co., Easton, Pa., a standard reference text in this field. Pharmaceutical carriers may be selected in accordance with the intended route of administration and the standard pharmaceutical practice.

For purposes of the present invention, the term "pharmaceutically acceptable salt" refers to those salts of compounds that are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. They may be prepared in situ when finally isolating and purifying the compounds of the invention, or separately by reacting them with pharmaceutically acceptable non-toxic bases or acids, including inorganic or organic bases and inorganic or organic acids. Pharmaceutically acceptable salts may be obtained using standard procedures well known in the art, for example by mixing a compound of the present invention with a suitable acid, for instance an inorganic acid or an organic acid. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the invention can form pharmaceutically acceptable salts with various amino acids. Suitable base salts include, but are not limited to, aluminum, calcium, lithium, magnesium, potassium, sodium, zinc, and diethanolamine salts.

For purposes of the present invention, the term "prevent" refers to stop from happening or to make something not happen.

For purposes of the present invention, the term "promoter" refers to a regulatory sequence that will determine in which cells and at what time a transgene is active. The promoter is typically derived from sequences of a mammalian gene upstream from the start site of transcription, and has been tested to contain the appropriate transcriptional regulatory elements. The promoter sequence normally contains the transcriptional start site as well as the transcription regulatory sequences. In addition, the promoter sequence also typically contains some extraneous sequence downstream of the transcriptional start. Synthetic promoters have also been designed for inducible gene expression and other specialized applications.

For purposes of the present invention, the term "subject" refers to an animal, for example, a mammal, such as a human, who has been the object of treatment, observation or experiment.

For purposes of the present invention, the term "target" refers to a living organism or a biological molecule to which some other entity, like a ligand or a drug, is directed and/or binds. For example, "target protein" may a biological molecule, such as a protein or protein complex, a receptor, or a portion of a biological molecule, etc., capable of being bound and regulated by a biologically active composition such as a pharmacologically active drug compound.

For purposes of the present invention, the term "therapeutically effective amount" and the term "effective amount" refers to the amount of a compound or composition that, when administered to a subject for treating a disease or disorder, or at least one of the clinical symptoms of a disease or disorder, is sufficient to affect such treatment of the disease, disorder, or symptom. A "therapeutically effective amount" may vary depending, for example, on the compound, the disease, disorder, and/or symptoms of the disease or disorder, severity of the disease, disorder, and/or symptoms of the disease or disorder, the age, weight, and/or health of the subject to be treated, and the judgment of the prescribing physician. An appropriate amount in any given instance may be readily ascertained by those skilled in the art or capable of determination by routine experimentation.

For purposes of the present invention, the term "tetracycline response element (Tre)" refers to a nucleic acid having a sequence that consists of 7 repeats of the 19 bp bacterial tet-o sequence separated by spacer sequences. It is the tet-o that is recognized and bound by the TetR portion of Tet-On or Tet-Off. The Tre is usually placed upstream of a minimal promoter that has very low basal expression in the absence of bound Tet-Off (or Tet-On). For some example, a tetracycline response element responds to tetracycline. A gene expression regulated by a Tre promoter can be induced by tetracycline.

For purposes of the present invention, the term "transfection" refers to a process of delivering a polynucleotide to a cell has been commonly termed transfection or the process of transfecting and also it has been termed transformation. The term transfecting as used herein refers to the introduction of a polynucleotide or other biologically active compound into cells. The polynucleotide may be used for research purposes or to produce a change in a cell that can be therapeutic. The delivery of a polynucleotide for therapeutic purposes is commonly called gene therapy. The delivery of a polynucleotide can lead to modification of the genetic material present in the target cell. The term stable transfection or stably transfected generally refers to the introduction and integration of an exogenous polynucleotide into the genome of the transfected cell. The term stable transfectant refers to a cell which has stably integrated the polynucleotide into the genomic DNA. Stable transfection can also be obtained by using episomal vectors that are replicated during the eukaryotic cell division (e.g., plasmid DNA vectors containing a papilloma virus origin of replication, artificial chromosomes). The term transient transfection or transiently transfected refers to the introduction of a polynucleotide into a cell where the polynucleotide does not integrate into the genome of the transfected cell. If the polynucleotide contains an expressible gene, then the expression cassette is subject to the regulatory controls that govern the expression of endogenous genes in the chromosomes. The term transient transfectant refers to a cell which has taken up a polynucleotide but has not integrated the polynucleotide into its genomic DNA.

For purposes of the present invention, the term "transfection agent," the term "transfection reagent," and the term "delivery vehicle" refers to a compound or compounds that bind(s) to or complex(es) with oligonucleotides and polynucleotides, and enhances their entry into cells. Examples of transfection reagents include, but are not limited to, cationic liposomes and lipids, polyamines, calcium phosphate precipitates, histone proteins, polyethylenimine, polylysine, and polyampholyte complexes. It has been shown that cationic proteins like histones and protamines, or synthetic polymers like polylysine, polyarginine, polyornithine, DEAE dextran, polybrene, and polyethylenimine may be effective intracellular in vitro delivery agents. Typically, the transfection reagent has a component with a net positive charge that binds to the oligonucleotide's or polynucleotide's negative charge. For delivery in vivo, complexes made with sub-neutralizing amounts of cationic transfection agent may be preferred. Non-viral vectors include protein and polymer complexes (polyplexes), lipids and liposomes (lipoplexes), combinations of polymers and lipids (lipopolyplexes), and multilayered and recharged particles. Transfection agents may also condense nucleic acids. Transfection agents may also be used to associate functional groups with a polynucleotide. Functional groups include cell targeting signals, nuclear localization signals, compounds that enhance release of contents from endosomes or other intracellular vesicles (such as membrane active compounds), and other compounds that alter the behavior or interactions of the compound or complex to which they are attached (interaction modifiers).

For purposes of the present invention, the term "transgene" refers to an artificial genetic material that has been transferred by any of a number of genetic engineering techniques from one organism to another. The introduction of a transgene has the potential to change the phenotype of an organism. In detail, a transgene is a segment of DNA containing a gene sequence that has been isolated from one organism and is introduced into a different organism. This non-native segment of DNA may retain the ability to produce RNA or protein in the transgenic organism, or it may alter the normal function of the transgenic organism's genetic code. In general, the DNA is incorporated into the organism's germ line. For example, in higher vertebrates this can be accomplished by injecting the foreign DNA into the nucleus of a fertilized ovum or oocytes. This technique is routinely used to introduce human disease genes or other genes of interest into strains of laboratory mice to study the function or pathology involved with that particular gene. The construction of a transgene requires the assembly of a few main parts. Generally, a transgene contains elements such as a promoter, which is a regulatory sequence that will determine where and when the transgene is active, an exon, a protein coding sequence, usually derived from the cDNA for the protein of interest, or a RNA fragment, and a stop sequence. The way that all these parts are typically combined is in a bacterial plasmid and the coding sequences are typically chosen from previous transgenes with previously known function.

For purposes of the present invention, the term "treating" or the term "treatment" of any disease or disorder refers to arresting or ameliorating a naturally occurring condition (for example, as a result of aging), disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to slowing the progression of a condition, inhibiting the disease or disorder, either physically, (e.g., stabilization of a discernible symptom), physiologically, (e.g., stabilization of a physical parameter), or both, and to inhibiting or slowing the progression of at least one physical parameter which may or may not be discernible to the subject. In some embodiments of the present invention, the terms "treating" and "treatment" refer to delaying the onset of the progression of the disease or disorder or at least one or more symptoms thereof in a subject who may be exposed to or predisposed to a disease or disorder even though that subject does not yet experience or display symptoms of the disease or disorder. The term "treatment" as used herein also refers to any treatment of a subject, such as a human condition or disease, and includes: (1) inhibiting the disease or condition, i.e., arresting the development or progression of the disease or condition, (2) relieving the disease or condition, i.e., causing the condition to regress, (3) stopping the symptoms of the disease, and/or (4) enhancing the conditions desired.

For purposes of the present invention, the term "vector" and the term "suitable vector" refer to a nucleic acid molecule capable of transporting another nucleic acid to which it has been linked or incorporated. A vector (for example, a plasmid or virus) may incorporate a piece of a nucleic acid having a sequence encoding an antigenic polypeptide and any desired control sequences. The choice of the vector will typically depend on the compatibility of the vector with a host cell into which the vector is to be introduced. A vector may be an expression vector that brings about the expression of a piece of a nucleic acid. An expression vector is usually a plasmid or virus designed for gene expression in cells. For example, a lentiviral vector is a vector derived from (i.e., sharing nucleotides sequences unique to) to lentivirus. A vector can be used to introduce a specific gene into a target cell, and can commandeer the cell's mechanism for protein synthesis to produce the protein encoded by the gene. A specific gene introduced into a target cell can also commandeer the cells' mechanism for producing RNA having a sequence that is complementary to the sequence of the specific gene. A plasmid may be engineered to contain regulatory sequences that act as enhancer and promoter regions and lead to efficient transcription of the gene carried on the expression vector.

For purposes of the present invention, the term "wild-type," when made in reference to a gene, refers to a gene that has the characteristics of a gene isolated from a naturally occurring source. The term "wild-type" when made in reference to a gene product refers to a gene product that has the characteristics of a gene product isolated from a naturally occurring source. The term "naturally-occurring" as applied to an object refers to the fact that an object can be found in nature. A wild-type gene is frequently that gene which is most frequently observed in a population and is thus arbitrarily designated the "normal" or "wild-type" form of the gene.

Description

While the invention is susceptible to various modifications and alternative forms, specific embodiment thereof has been shown by way of example in the drawings and will be described in detail below. It should be understood, however that it is not intended to limit the invention to the particular forms disclosed, but on the contrary, the invention is to cover all modifications, equivalents, and alternatives falling within the spirit and the scope of the invention.

Embodiments of the present invention provide a pharmaceutical composition comprising an effective amount of isolated RNA fragments of a cluster of long non-coding RNA transcripts (myosin heavy-chain-associated RNA transcripts) and the methods of using this pharmaceutical composition for treating pathological hypertrophy.

Cardiac hypertrophy and failure are characterized by transcriptional reprogramming of gene expression. Adult cardiomyocytes in mice primarily express α-myosin heavy chain (α-MHC, also known as Myh6), whereas embryonic cardiomyocytes express β-MHC (also known as Myh7). Cardiac stress triggers adult hearts to undergo hypertrophy and a shift from α-MHC to fetal β-MHC expression. Brg1, a chromatin-remodeling protein, has a critical role in regulating cardiac growth, differentiation and gene expression.[41] In embryos, Brg1 promotes myocyte proliferation by maintaining Bmp10 and suppressing $p57^{kip2}$ expression. It preserves fetal cardiac differentiation by interacting with histone deacetylase (HDAC) and poly (ADP ribose) polymerase (PARP) to repress α-MHC and activate β-MHC. In adults, Brg1 (also known as Smarca4) is turned off in cardiomyocytes. It is reactivated by cardiac stresses and forms a complex with its embryonic partners, HDAC and PARP, to induce a pathological α-MHC to β-MHC shift. Preventing Brg1 re-expression decreases hypertrophy and reverses this MHC switch. BRG1 is activated in certain patients with hypertrophic cardiomyopathy, its level correlating with disease severity and MHC changes. Brg1 maintains cardiomyocytes in an embryonic state, and demonstrate an epigenetic mechanism by which three classes of chromatin-modifying factors—Brg1, HDAC and PARP—cooperate to control developmental and pathological gene expression.

Myosin heavy chain is the molecular motor in muscle cells, and two isoforms, α-MHC and β-MHC, are expressed specifically in mammalian hearts. α-MHC has higher ATPase activity than β-MHC, and the relative degree of α-MHC and β-MHC varies under different pathophysiological conditions.[1] The α- to 13-MHC ratio correlates directly with overall cardiac performance in animals[2,3,4] as well as in patients with cardiomyopathy and heart failure.[5,6,7,8] During embryonic development, embryonic cardiomyocytes are highly proliferative and express primarily β-MHC. Cardiomyocytes grow primarily by proliferation to increase cell number. During neonatal development, the β-MHC expression switches to α-MHC expression. Cardiomyocytes physiologically switch from proliferative to hypertrophic growth to increase cell size. In adult under physiological condition, cardiomyocytes are post-mitotic and mainly express α-MHC. Physiological hypertrophy may result from normal exercise. However, in adult under pathological condition or stress condition, adult cardiomyocytes undergo hypertrophy and a shift from adult α-MHC expression to embryonic β-MHC expression. Cardiomyocytes are postmitotic. Pathological hypertrophy and fibrosis result from cardiac insults.

MHC protein mutations also cause cardiac dysfunction in mice and humans.[9,10] Pathological hypertrophy of adult hearts is associated with α-MHC downregulation and β-MHC induction,[11] which represents a return to a fetal state of MHC expression. However, hearts expressing α-MHC have a better outcome under stress conditions than those expressing mainly-MHC.[2,3,4] Thus, strategies to control MHC expression represent an attractive approach for heart failure therapy.[1,2]

Chromatin remodeling offers one such control to modulate gene expression. The Brg1/Brm-associated-factor (BAF) complex, consisting of 12 protein subunits, is a major type of ATP-dependent chromatin-remodeling complex in vertebrates.[13] Brg1 is the essential ATPase subunit of the BAF complex,[14] and interacts with two other classes of chromatin-modifying enzymes, HDAC[15] and PARP,[16] to regulate gene expression during cardiac growth, differentiation and hypertrophy in mice. Both HDACs and PARP1 are therapeutic targets for cardiac hypertrophy, as pharmacological inhibition of their activities or genetic mutations of class I HDACs and PARP1 in mice reduce hypertrophy.[17,18,19,20,21,22] The interaction of Brg1 with HDACs and PARP1, and its activation in certain patients with hypertrophic cardiomyopathy, indicate that Brg1/BAF may be a target for treating cardiac hypertrophy and failure.

FIG. 1 shows a model of developmentally activated and stress-induced assembly of BAF/HDAC/PARP complexes on the α-MHC promoter, and BAF/PARP complex on the β-MHC promoter. Brg1/BAF may have regenerative and therapeutic implications give its newly identified roles in both embryonic and adult cardiomyocytes. Similar mechanisms are directed by Brg1 to control cardiac growth, differentiation and gene expression under developmental and pathological conditions. The stress-dependent assembly of a developmental complex to modify chromatins in adult hearts provides a molecular explanation for fetal gene activation in the diseased adult myocardium. HDAC, PARP and now Brg1/BAF are the only classes of chromatin-modifying factors known to regulate cardiac hypertrophy. As shown in FIG. 1, cardiac stresses activate Brg1, which then assembles a BAF/HDAC/PARP chromatin complex on MHC promoters, where they may interact with transcription factors such as TR, TEF1, MEF2, SRF, GATA4 and NFAT[36,37] to control MHC expression. The induction of Brg1 by hypertrophic stimuli suggests that chromatin may ultimately be where all the stress-response signals converge for the regulation of MHC genes, a critical step in the myopathic process.

Brg1/BAF, aside from thyroid hormone receptors,[36] provides the only known direct mechanism to antithetically regulate α-MHC and β-MHC. This opposite MHC regulation may underlie the on-off, rather than graded, switching of MHC in individual cardiomyocytes of hypertrophic hearts.[28] Exactly how HDACs and PARPs contribute to this BAF-mediated process awaits further investigations. HDACs and PARPs may covalently modify histones and thereby help anchor BAF to certain sites of MHC promoters. BAF proteins may also be modified through acetylation/deacetylation or poly-ADP-ribosylation by HDACs and PARPs. Such modifications may decide the composition of the BAF complex and how BAF interacts with chromatin as well as with other MHC regulators such as miR-208.[1] Elucidating these issues will help to determine how the chromatin and target specificities of BAF may be established by its possible combinatorial assembly with the large families of 17 PARP[16] and 18 HDAC[15] proteins.

The role of long noncoding RNA (lncRNA) in adult hearts is unknown; also unclear is how lncRNA modulates nucleosome remodeling. An estimated 70% of mouse genes undergo antisense transcription,[39] including myosin heavy chain 7 (Myh7), which encodes molecular motor proteins for heart contraction.[40]

Embodiments of the present invention identify a cluster of lncRNA transcripts from Myh7 loci and demonstrate a new lncRNA-chromatin mechanism for heart failure. In mice, these transcripts, which are named myosin heavy-chain-associated RNA transcripts (Myheart, or Mhrt), are cardiac-specific and abundant in adult hearts. Embodiments of the present invention provide modified Mhrt that binds to a cromatin remodeler Brg1 to inhibit Brg1's genomic targeting and gene regulation function. Pathological stress activates the Brg1-Hdac-Parp chromatin repressor complex[41] to inhibit Mhrt transcription in the heart. Such stress-induced Mhrt repression is essential for cardiomyopathy to develop: restoring Mhrt to the pre-stress level protects the heart from hypertrophy and failure.

Mhrt antagonizes the function of Brg1, a chromatin-remodeling factor that is activated by stress to trigger aberrant gene expression and cardiac myopathy.[41] Mhrt prevents Brg1 from recognizing its genomic DNA targets, thus inhibiting the helicase domain chromatin targeting and gene regulation by Brg1. It does so by binding to the helicase domain of Brg1, a domain that is crucial for tethering Brg1 to chromatinized DNA targets. Brg1 helicase has dual nucleic-acid-binding specificities: it is capable of binding lncRNA (Mhrt) and chromatinized—but not naked—DNA. This dual-binding feature of helicase enables a competitive inhibition mechanism by which Mhrt sequesters Brg1 from its genomic DNA targets to prevent chromatin remodeling. A Mhrt-Brg1 feedback circuit is thus crucial for heart function. Human MHRT also originates from MYH7 loci and is repressed in various types of myopathic hearts, suggesting a conserved lncRNA mechanism in human cardiomyopathy. Thus, embodiments identify a cardioprotective lncRNA, define a new targeting mechanism for ATP-dependent chromatin-remodeling factors, and establish a new paradigm for lncRNA-chromatin interaction.

Mhrt RNAs have No Coding Potential

FIGS. 2, 3, 4, 5, 6 and 7 are a set of images and graphs illustrating the profile of the noncoding RNA Mhrt. FIG. 2 is a schematic illustration of Mhrt RNAs originating from the intergenic region between Myh6 and Myh7 and transcribed into Myh7. Myh7 exons and introns are indicated. "m" refers to mid region of the RNAs. "F1" and "R1," targeting the 5' and 3' Mhrt common sequences, are the primers used for subsequent polymerase chain reaction (PCR). FIG. 3 is a graph showing quantitative PCR with reverse transcription (RT-qPCR) of Mhrt RNAs using primers targeting common regions of Mhrt RNAs in tissues from 2-month-old mice. FIG. 4 is a graph showing RT-qPCR of Mhrt, Myh6 and Myh7 in mouse hearts at different ages. Mhrt and Myh6/Myh7 ratio of embryonic day (E) 11 hearts are set as 1. "P" refers to postnatal day. FIG. 5 is a set of images showing RNA in situ analysis of Mhrt (dark spots) in adult hearts. The RNA probe targets all Mhrt species. Light spots represent nuclear fast red staining. White arrowheads indicate myocardial nuclei. Black arrowheads indicate nuclei of endothelial, endocardial or epicardial cells. Dashed lines demarcate the myocardium from endocardium Endo.) or from epicardium (Epi.). Scale bars=50 µm. FIG. 6 is a graph showing RT-qPCR of nuclear/cytoplasmic RNA in adult hearts. TfIIb (also known as Gtf2b), Hprt1 and 28S rRNA are primarily cytoplasmic RNAs; Neat1, nuclear lncRNA. TfIIb ratio is set as 1. FIG. 7 is a graph showing ribosome profiling: ribosome density on coding RNAs and lncRNAs. P values: Student's t-test. Error bars show standard error of the mean (s.e.m.).

FIGS. 8, 9, 10, 11, 12 and 13 are a set of image and graphs showing that Mhrt RNAs have no coding potential. FIG. 8 is an image of RNA in situ analysis of Mhrt in a mouse E12 heart. The RNA probe targets all Mhrt species. Red: nuclear fast red. Arrowheads indicate nuclei of endothelial, endocardial or epicardial cells. Inset shows magnified region from the boxed area. Abbreviate "endo" refers to endocardium; abbreviate "epi" refers to epicardium; "IVS" refers to interventricular septum; "LV" refers to left ventricle; "RA" and "RV" refer to right atrium and ventricle, respectively. Scale bars=100 µm. FIG. 9 is a graph of codon substitution frequency (CSF) scores of TfIIb and Hprt1 mRNA, as well as full-length Mhrt species. FIG. 10 is an image of in vitro translation of control Mhrt species (709, 779, 826, 828, 857, 1147) and luciferase (Luc). Arrow points to the protein product of luciferase. FIG. 11 is an image of Biotin-labelling of Mhrt species (709, 779, 826, 828, 857, 1147) and luciferase in the in vitro translation reactions. Arrow points to the RNA product of luciferase. FIG. 12 shows ribosome profiling relative to whole transcriptome RNA sequencing. x-axis: genomic position at the human GAPDH and the murine Myh7 loci. y-axis: mapped reads. FIG. 13 is an image of scatter plot of RNA in fragments per kilobase per million reads (FPKM). Noncoding RNAs (purple) cluster towards the x-axis; coding RNAs (orange) towards the y-axis. Mhrt779 is found below both the identity line (dashed, slope=1, intercept=0) and the smooth-fit regression line (solid line 740). RNA examples are endogenous except that HOTAIR is co-transfected with Mhrt779.

According to embodiments, by 5' and 3' rapid amplification of complementary DNA ends, an alternative splicing of Myh7 antisense transcription into a cluster of RNAs of 709 to 1,147 nucleotides (Mhrt RNAs) is discovered. This alternative splicing of Myh7 antisense transcription contains partial sequences of Myh7 introns and exons (FIG. 2). Mhrt RNAs are cardiac-specific (FIG. 3), present at low levels in fetal hearts, with increasing abundance as the hearts matured and Myh6/Myh7 ratio increased (FIG. 4). RNA in situ analysis shows that Mhrt RNAs resided in the myocardium but not endocardium or epicardium (FIGS. 5 and 8). Quantification of nuclear/cytoplasmic RNA in heart extracts reveals that Mhrt transcripts are primarily nuclear RNAs (FIG. 6). Coding substitution frequencies[42,43] of Mhrt RNAs predicts a negative/low protein-coding potential, in vitro translation of Mhrt RNAs yields no proteins, and ribosome profiling[44] reveals no/minimal ribosomes on Mhrt (FIGS. 7, 9, 10, 11, 12 and 13). Consequently, Mhrt RNAs are non-coding RNAs in cardiomyocyte nuclei.

Mhrt RNAs Inhibit Cardiac Hypertrophy and Failure

FIGS. 14, 15, 16, 17, 18, 19, 20, 21 and 22 are a set of images and graphs illustrating that Mhrt inhibits cardiac hypertrophy and failure according to some embodiments of the present invention. FIG. 14 is a graph showing quantification of cardiac Mhrt RNAs 2-42 days (d) after TAC operation. FIG. 15 is an image of result of RT-PCR of Mhrt RNAs in adult heart ventricles. Primers (F1 and R1 used in FIG. 2) target Mhrt common regions. Size controls 779, 826 and 709 are PCR products of recombinant Mhrt779, Mhrt826 and Mhrt709, respectively. FIG. 16 is an image of Northern blot of Mhrt RNAs in adult heart ventricles. The probe targets common regions of Mhrt RNAs. "Negative" refers to control RNA from 293T cells. Size control: 826 is recombinant Mhrt826; 643 (not a distinct Mhrt species) contains the 5' common region of Mhrt. FIG. 17 is a set of graphs showing quantification of Mhrt779 in control or Tg779 mice with or without doxycycline (Dox) or TAC operation. Mhrt779-specific PCR primers are used. "Ctrl" refers to control mice. FIG. 18 is a set of images showing ventricle/body-weight ratio of hearts 6 weeks (wk) after TAC. Scale bars=1 mm FIG. 19 is a graph of a result of quantification of cardiomyocyte size in control and Tg779 mice 6 weeks after TAC by wheat germ agglutinin staining. FIG. 20 is a set of images showing trichrome staining in control and Tg779 hearts 6 weeks after TAC. Red indicates cardiomyocytes; blue indicates fibrosis. Scale bars=20 µm. FIGS. 21 and 22 are graphs of results of echocardiographic measurement of left ventricular fractional shortening (FIG.

21) and internal dimensions at end-diastole (LVIDd) and end-systole (LVIDs) (FIG. 22) 6 weeks after TAC. P values: Student's t-test. Error bars show s.e.m.

FIGS. 23, 24, 25, 26 and 27 are a set of images and graphs showing an image showing quantification of Myh6/Myh7, northern blot, and Mhrt779 characterization. FIG. 23 shows quantification of cardiac Myh6/Myh7 ratio 2-42 days after sham or TAC operation. FIG. 24 shows Northern blot analysis of Mhrt, Myh6 and Myh7. Negative: control RNA from 293T cells. Size control: 826 is recombinant Mhrt826; 643 (not a distinct Mhrt species) contains the 5' common region of Mhrt. Heart: adult heart ventricles. FIG. 25 shows un-cropped northern blots of Mhrt, Myh6 and Myh7. FIG. 26 shows RNA in situ hybridization of Mhrt779 of adult heart ventricles. White arrowheads indicate nuclei of myocardial cells. Black arrowheads indicate nuclei of endothelial, endocardial or epicardial cells. Dark spots: Mhrt779; light spots: nuclear fast red. Epi, epicardium. The dashed line separates the epicardium from myocardium. Scale bars=50 µm. FIG. 27 shows quantification of TfIIb, Hprt1, 28S rRNA, Neat1 and Mhrt779 in the nuclear and cytoplasmic fraction of adult heart ventricle extracts. The nuclear/cytoplasmic ratio of TfIIb is set as 1. P values: Student's t-test. Error bars show s.e.m.

FIGS. 28, 29, 30, 31, 32 and 33 are is a set of images and graphs showing wheat germ agglutinin staining, time course and molecular marker studies of the stressed Tg779 mice. FIG. 28 shows wheat germ agglutinin (WGA) immunostaining 6 weeks after the sham or TAC operation. Green: WGA stain, outlining cell borders of cardiomyocytes. Blue: 4',6-diamidino-2-phenylindole (DAPI). Ctrl, control mice. Scale bars=50 µm. FIG. 29 shows time course of fractional shortening (FS) in control and Tg779 mice. FIG. 30 shows quantification of Anf, Bnp, Serca2 and Tgfb1 in control and Tg779 mice 2 weeks after sham or TAC operation. FIG. 31 shows experimental design for treatment study and time course of left ventricular fractional shortening changes. FIG. 32 shows fractional shortening of the left ventricle (LV) 8 weeks after the operation. FIG. 33 shows ventricular weight/body weight ratio of hearts harvested 8 weeks after sham or TAC operation. P values: Student's t-test. Error bars show s.e.m.

FIGS. 34, 35, 36, 37, 38, 39, 40, 41 and 42 are a set of graphs and schematics showing Mhrt complexes with Brg1 through the helicase domain. FIG. 34 shows DNaseI digital footprinting of Myh6/Mhrt promoter loci from ENCODE. Myh6 and Mhrt are transcribed in opposite directions as indicated by arrows. Bars represent DNA fragments protected from DNaseI digestion. Black boxes (a1-a4) refer to promoter regions with high sequence homology (FIG. 43, described below). FIG. 35 shows quantification of Myh7/Myh6 ratio in control (Ctrl) and Tg779 (Tg) hearts 2 weeks after TAC. FIG. 36 shows RNA-immunoprecipitation (IP) of Mhrt-Brg1 in ventricles from control hearts (Ctrl) with sham/TAC operation; Tg779 hearts after TAC; Brg1-null (Tnnt2-rtTA;Tre-Cre;Brg1$^{fl/fl}$) hearts after TAC; and P1 hearts. FIG. 37 shows ChIP analysis of Brg1 in control (Ctrl) and Tg779 hearts 2 weeks after TAC. FIG. 38 shows luciferase reporter assay of Myh6 and Myh7 promoters in neonatal rat cardiomyocytes. Mhrt represents pAdd2-Mhrt779; Vector represents pAdd2 empty vector. FIG. 39 shows RNA-IP and EMSA of recombinant Brg1 proteins and in vitro transcribed Mhrt779. Biotin-labelled Mhrt779: 50 nM; unlabeled Mhrt779: 500 nM. FIG. 40 shows schematics of mouse Brg1 protein. The helicase core includes the DExx-c and HELIC-c domain. FIG. 41 shows EMSA of Mhrt779 and Brg1 helicase. FIG. 42 shows binding affinity of Mhrt779 for MBP-tagged D1D2 determined by EMSA.

Data are from multiple independent measurements. Nonlinear regression curves are generated by GraphPad Prism. P values: Student's t-test. Error bars show s.e.m.

As shown in FIG. 14 Mhrt RNAs are downregulated by 46-68% in hearts pressure-overloaded by transaortic constriction (TAC)[41], beginning by 2 days and lasting for 42 days after TAC. Such Mhrt reduction coincides with the TAC-induced Myh6 to Myh7 isoform switch characteristic of cardiomyopathy[1,5,45] (FIG. 23). To define Mhrt function, Mhrt779 (SEQ ID NO: 1), the most abundant Mhrt species, with 779 nucleotides (FIGS. 15, 16, 24, 25, 26 and 27) is focused on. A transgenic mouse line is generated to restore Mhrt779 level in stressed hearts. This transgenic line, driven by tetracycline response element (Tre-Mhrt779), is crossed to a cardiac-specific driver line (Tnnt2-rtTA)[41] that employs troponin promoter (Tnnt2) to direct expression of reverse tetracycline-dependent transactivator (rtTA). The resulting Tnnt2-rtTA;Tre-Mhrt779 line (abbreviated as Tg779) enabled the use of doxycycline to induce Mhrt779 expression in cardiomyocytes. Within 7-14 days of doxycycline treatment, Mhrt779 increased by ~1.5-fold in left ventricles of Tg779 mice; this offset Mhrt779 suppression in TAC-stressed hearts to maintain Mhrt779 at the pre-stress level (FIG. 17). Six weeks after TAC, doxycycline-treated control mice (Tre-Mhrt779, Tnnt2-rtTA or wild type) developed severe cardiac hypertrophy and fibrosis with left ventricular dilatation and reduced fractional shortening. Conversely, doxycycline-treated Tg779 hearts—with Mhrt779 maintained at the pre-stress level—developed much less pathology, with a 45.7% reduction in the ventricle/body-weight ratio (FIG. 18) and a 61.3% reduction in cardiomyocyte size (FIGS. 19 and 28), minimal/absent cardiac fibrosis (FIG. 20), a 45.5% improvement of fractional shortening (FIGS. 21 and 29), normalized left ventricular size (FIG. 22), and reduced pathological changes of Anf (also known as Nppa), Bnp (also known as Nppb), Serca2 (also known as Atp2a2), Tgfb1 and Opn (also known as Spp1) expression.[46,47,48,49] (FIG. 30 and FIG. 65, described below). To further test the cardioprotective effects of Mhrt, Mhrt779 is induced after 1-2 weeks of TAC when hypertrophy had begun. This approach reduced hypertrophy by 23% and improved fractional shortening by 33% in 8 weeks after TAC (FIGS. 31, 32 and 33). The efficacy of late Mhrt779 introduction suggests that a sustained repression of Mhrt in stressed hearts is essential for continued decline of cardiac function.

Regulation of the Mhrt Promoter

FIGS. 43, 44, 45, 46, 47, 48, 49 and 50 are a set of graphs showing the regulation of the Mhrt promoter. FIG. 43 shows a sequence alignment of Mhrt promoter loci from mouse, human and rat. Peak heights indicate degree of sequence homology. Black boxes (a1-a4) are sequences of high homology, which are used for further ChIP analysis. The region (-2329 and +143) between Myh6 and Mhrt is the putative Mhrt promoter. Red regions are promoter elements. Pink regions are introns. Yellow regions are untranslated regions. FIG. 44 shows a ChIP-qPCR analysis of Mhrt promoter using antibodies against Pol II in tissues of adult mice. FIG. 45 shows a ChIP-qPCR analysis of Mhrt promoter using antibodies against H3K4me3 in tissues of adult mice. FIG. 46 shows a ChIP-qPCR analysis of Mhrt promoter using antibodies against H3K36me3 in tissues of adult mice. FIG. 47 shows RT-qPCR quantification of Mhrt in control and Brg1-null hearts after 7 days of TAC. "Ctrl" refers to control. "Brg1-null" refers to Tnnt2-rtTA;Tre-Cre;Brg1$^{fl/fl}$. FIG. 48 shows luciferase reporter assay of Mhrt promoter in SW13 cells. "Ctrl" refers to dimethylsulphoxide (DMSO). "PJ-34" refers to PARP inhibitor; "TSA" refers to trichostatin (HDAC inhibitor). FIG. 49 shows ChIP analysis of BRG1, HDAC2, HDAC9 and PARP1 in SW13 cells. The cells are transfected with episomal Mhrt promoter cloned in pREP4. FIG. 50 shows deletional analyses of the Mhrt promoter in luciferase reporter assays in SW13 cells. Luciferase activity of full-length Mhrt promoter was set up as 1. P values: Student's t-test. Error bars show s.e.m.

To study Mhrt regulation, in some embodiments the 5' upstream region of the Mhrt genomic site (−2329 to +143) (FIG. 43) is examined for signatures of a lncRNA promoter: RNA polymerase II (Pol II), histone H3 trimethylated lysine 4 (H3K4me3) and histone H3 trimethylated lysine 36 (H3K36me3).[42,50,51] By chromatin immunoprecipitation (ChIP) of left ventricles, it is found that this putative promoter contains four evolutionarily conserved elements (FIG. 43, black boxes a1 to a4)[41] that are enriched with Pol II (promoters a1 to a4), H3K4me3 (promoter a1 and a4) and H3K36me3[50,52,53,54] (promoters a1 and a3/a4) (FIGS. 43, 44, 45, and 46). Conversely, no Pol II, H3K4me3 or H3K36me3 enrichment is found in control Shh and Vegfa promoters or in thymus and lungs that did not express Mhrt RNAs (FIGS. 44, 45, and 46). These results reveal an active, cardiac-specific lncRNA promoter controlling Mhrt expression.

How Mhrt is repressed in stressed hearts is examined in some embodiments. It is postulated that cardiac stress activates Brg1, leading it to occupy the a1-a4 promoter and to repress Myh6[41] and Mhrt in opposite transcription directions (FIG. 43). Indeed, Mhrt repression requires Brg1: TAC suppressed Mhrt RNAs in control but not Brg1-null hearts (Tnnt2-rtTA;Tre-Cre;Brg1$^{fl/fl}$)[41] (FIG. 47). To test Brg1 activity on the Mhrt promoter, the a1-a4 promoter in the Mhrt transcription direction (−2329 to +143) is cloned into an episomal luciferase reporter, pREP4, that allows promoter chromatinization.[55] Brg1 is then transfected into Brg1-deficient SW13 cells[56] to reconstitute the Brg1/BAF complex for reporter assays. Brg1 transfection caused a ~50% reduction of Mhrt promoter activity (P<0.0001), and such Mhrt repression is virtually abolished by Hdac inhibition with trichostatin-A or Parp inhibition with PJ-34 (FIG. 48),[57] indicating a cooperative repressor function between Brg1, Hdac and Parp. ChIP verified that the Mhrt promoter (a1-a4) is occupied by Brg1, Hdac2/9 and Parp1 in stressed hearts[41] and in the pREP4 reporter episome (FIG. 49). These findings indicate that Mhrt is repressed by the stress-induced Brg1-Hdac-Parp complex[41] through the a1-a4 promoter.

Mhrt Complexes with Brg1 Through the Helicase Domain

FIGS. 51, 52, 53, 54, 55, 56, 57, 58, 59 and 60 are a set of graphs and images showing that Mhrt does not affect Myh expression by direct RNA sequence interference. FIG. 51 shows qPCR analysis of Mhrt779, Myh6 and Myh7 in mice without TAC operation. Expression levels were normalized to TfIIb, and the control is set as 1. Ctrl, control mice. FIG. 52 shows RNA quantification of Mhrt in SW13 cells transfected with Vector (pAdd2), HOTAIR (pAdd2-HOTAIR) or Mhrt (pAdd2-Mhrt779). FIG. 53 shows RNA quantification of HOTAIR in SW13 cells transfected with Vector (pAdd2), HOTAIR (pAdd2-HOTAIR) or Mhrt (pAdd2-Mhrt779). Expression in vector-transfected cells is set as 1. Constructs containing Myh6 or Myh7 were co-transfected into SW13 cells used for FIGS. 15, 16, 17, 18, 19, 20, 21 and 22. FIG. 54 shows RNA quantification of Myh6 in SW13 cells relative to GAPDH. FIG. 55 shows RNA quantification of Myh7 in SW13 cells relative to GAPDH. FIG. 56 shows Western blot analysis of Myh6 in SW13 cells. FIG. 57 shows Western blot analysis of Myh7 in SW13 cells. Constructs containing Myh6- and Myh7-coding sequences were tagged with Flag and co-transfected with vector, HOTAIR or Mhrt779. GAPDH was used as the loading control. Flag-D1 was used as a positive control for the Flag antibody. FIG. 58 shows protein quantification of Myh6 in control and transfected SW13 cells relative to GAPDH. FIG. 59 shows protein quantification of Myh7 in control and transfected SW13 cells relative to GAPDH. Signals of Myh6 and Myh7 from major bands or the entire lanes were quantified. WB, western blot. FIG. 60 shows a luciferase reporter assay of Mhy6 and Myh7 promoters in SW13 cells transfected with vector (pAdd2) or Mhrt (pAdd2-Mhrt779). P values: Student's t-test. Error bars show s.e.m.

Because Myh6 and Mhrt are both regulated by the a1-a4 promoter, it is hypothesized that a1-a4 contained two elements to regulate Myh6 and Mhrt—with the a1 element controlling Myh6 and the a3/4 element controlling Mhrt (FIG. 43). On a1 and a3/4 (but not a2), cardiac-specific enrichment of Brg1,[41] H3K4me3 and H3K36me3 (FIGS. 45 and 46), and DNaseI genomic footprints (FIG. 34) are found.[58] To test a3/4 for Mhrt regulation, deletional analysis of the a1-a4 promoter in the Mhrt transcription direction is conducted. In reporter assays, a3/4 is necessary and sufficient for Mhrt promoter activity and for Brg1-dependent Mhrt repression, whereas a1 is not essential for either (FIG. 50). Conversely, a1 is necessary and sufficient for Brg1 to repress the Myh6 promoter[41], but a3/4 is not required.[41] Therefore, a1 and a3/4 are two functionally distinct elements for Brg1 to separately control Myh6 and Mhrt.

In stressed hearts, Brg1 represses Myh6 and activates Myh7[41], causing a pathological switch of Myh6/7 expression, contributing to cardiomyopathy.[59] This stress/Brg1-dependent Myh switch is largely eliminated by Mhrt779 (FIG. 35), and the inhibition of the Myh switch by Mhrt did not involve RNA-RNA sequence interference between Mhrt and Myh (FIGS. 51, 52, 53, 54, 55, 56, 57, 58, 59 and 60). Instead, it required a physical interaction between Mhrt RNA and Brg1. RNA immunoprecipitation of TAC-stressed adult hearts or Brg1-expressing neonatal hearts showed that Brg1 co-immunoprecipitated with Mhrt779 but not control RNAs, and that Mhrt779 complexed with Brg1 but not with the polycomb proteins Ezh2 or Suz12 (FIG. 36 and FIGS. 61 and 62, described below). The Brg1-Mhrt complex is minimal in unstressed adult hearts with low Brg1[41] or in stressed Brg1-null hearts (Tnnt-rtTA; Tre-Cre;Brg1$^{fl/fl}$)[41] (FIG. 36). These results suggest that Mhrt binds to Brg1 to influence its gene regulation.

FIGS. 61, 62, 63, 64 and 65 is a set of images and graphs of RNA-IP controls showing that Opn is another target gene of Brg1 in stressed hearts. FIG. 61 shows immunostaining of Brg1 in P1 heart. Red: Brg1. Green: WGA. Blue: DAPI. Ctrl, control. Scale bar=50 μm. FIG. 62 shows RNA-IP of Mhrt in P1 hearts using antibodies against Ezh2 and Suz12. Right panels show immunostaining of Ezh2 and Suz12 in P1 hearts. PRC2, polycomb repressor complex 2. Red: Ezh2 or Suz12. Green: WGA. Blue: DAPI. Scale bars=50 μm. FIG. 63 shows quantification of Opn mRNA in control and Brg1-null (Tnnt2-rtTA;Tre-Cre;Brg1$^{fl/fl}$) mice after sham or TAC operation. FIG. 64 shows ChIP of Brg1 on Opn proximal promoter in control and transgenic (Tg779) mice after sham or TAC operation. FIG. 65 shows quantification of Opn in control and transgenic (Tg779) mice after sham or TAC operation. P values: Student's t-test. Error bars show s.e.m.

FIGS. 66, 67, 68, 69, 70, 71 and 72 are a set of images and graphs showing that the induction of Mhrt779 is insufficient to change Brg1 mRNA or protein level. FIG. 66 shows a qPCR analysis of Brg1 expression in hearts without TAC operation. Ctrl: control mice. FIGS. 67, 68, 69 and 70 show immunostaining of Brg1 (red) in adult heart ventricles 2 weeks after sham or TAC operation. Green: WGA. Blue: DAPI. Scale bars=50 μm. FIG. 71 shows a Western blot analysis of Brg1 and Coomassie staining of total proteins in control or Tg779 hearts after 2 weeks of sham or TAC operation. FIG. 73 shows a quantification of Myh6 and Myh7 in control (Ctrl) and Tg779 hearts after 2 weeks of sham or TAC operation. P values: Student's t-test. Error bars show s.e.m.

How Mhrt regulated Brg1 activity on its in vivo target genes, including Myh6[41], Myh7[41] and Opn (osteopontin, critical for cardiac fibrosis[48]) (FIGS. 63, 64 and 65) is tested. In doxycycline-treated, TAC-stressed Tg799 hearts, Mhrt779—without affecting the Brg1 messenger RNA/protein level (FIGS. 66, 67, 68, 69, 70 and 71)—reduced Brg1 occupancy on Myh6, Myh7 and Opn promoters by 60-90% (FIG. 37), causing a 56-76% loss of Brg1-controlled Myh switch and Opn activation (FIGS. 35, 65 and 72). Primary rat ventricular cardiomyocytes are used to conduct reporter assays. In these cells, as observed in vivo, Brg1 repressed Myh6 and activated Myh7 and Opn promoters; Mhrt779 reduced Brg1 activity on these promoters by 54-80% (FIG. 38). Accordingly, Mhrt prevents Brg1 from binding to its genomic targets to control gene expression.

How Brg1 or ATP-dependent chromatin remodellers recognize their target promoters is an important but not fully understood issue in chromatin biology. Biochemically, recombinant Brg1 proteins and in vitro transcribed Mhrt779 could directly co-immunoprecipitate without involving other factors (FIG. 39). An electrical mobility shift assay (EMSA) showed that Brg1 shifted biotin-labelled Mhrt779 to form a low mobility protein—RNA complex that is competitively disrupted by unlabeled Mhrt779 (FIG. 39). Brg1, which belongs to the SWI/SNF family of chromatin-remodeling factors, contains a helicase/ATPase core that is split by an insertion into two RecA-like domains: DEAD-like helicase superfamily C-terminal domain, D1 (DExx-c) and helicase superfamily C-terminal domain, D2 (HELIC-c)[60,61] with signature motifs of DEAD-box, superfamily 2 RNA helicase.[61,62] (FIG. 40 and FIG. 92, described below). FIG. 92 illustrates the alignment of amino acid sequences for the following proteins: the RNA binding protein Vasa from fruit fly (SEQ. ID NO: 69), Brg1 protein from human and mouse (SEQ ID NO: 70), Rad54 protein from zebrafish (SEQ ID NO: 71), Rad54 protein from sulfolobus (SEQ ID NO: 72), and chromodomain-helicase-DNA-binding protein 1 (Chd1) from yeast (SEQ ID NO: 73). SWI/SNF proteins although conserved with RNA helicases, are observed to bind DNA[63] and mediate DNA structural changes and repair.[55] The binding properties of Brg1 remained undefined. To test whether Mhrt can bind to Brg1 helicase, maltose-binding protein (MBP)-tagged recombinant proteins that contain the Brg1 DExx-c domain (MBP-D1, amino acids 774-913), the HELIC-c domain with C-terminus extension (MBP-D2, 1086-1310), or the entire helicase (MBP—D1D2, 774-1310) (FIG. 93) are generated. D1D2 shows the highest Mhrt binding affinity (dissociation constant ($K_d$)= 0.76 mM); D1 shows moderate affinity ($K_d$=1.8 mM); D2 modest affinity ($K_d$>150 mM); and MBP does not bind at all (FIGS. 41 and 42). Therefore, Brg1 helicase binds Mhrt with high affinity.

FIGS. 73, 74, 75, 76, 77, 78, 79, 80, 81, 82, 83, 84, 85 and 86 are a set of images and graphs showing that Mhrt inhibits chromatin targeting and gene regulation by Brg1 according to an exemplary embodiment of the present invention. Contrary to its potent RNA binding, Brg1 helicase showed no detectable binding to the naked DNA of the Myh6 promoter (596 bp, −426 to +170, critical for the control of Myh6 by Brg1[41] (FIG. 94). To test whether Brg1 helicase could bind chromatinized DNA, nucleosomal DNA is generated in vitro by assembling histone octamers (histones H2A, H2B, H3 and H4)[64] on Myh6 promoter DNA, as well as on control neomycin phosphotransferase gene (Neo) and 5S ribosomal (r)DNA (5S rDNA). 50-65% efficiency of nucleosome assembly is achieved, comparable between Myh6, Neo and 5S rDNA (FIG. 73). Because the large nucleosome size precludes a clear EMSA resolution, amylose is used to pull down MBP-tagged D1D2 proteins. D1D2 pulls down nucleosomal Myh6 promoter DNA but not the naked one (FIG. 74). The pull-down efficiency of nucleosomal Myh6 is ~3-6-fold that of Neo or 5S rDNA (FIG. 75), and Mhrt779 is capable of disrupting D1D2-Myh6 pull-down (FIG. 76). Although D1D2 bound to histone H3 (FIG. 77), histone binding is insufficient to anchor D1D2 to nucleosomal DNA, as D1D2 bound poorly to nucleosomal Neo and 5S rDNA that also contained histones (FIG. 75). Therefore, chromatinized DNA targets are biochemically recognized by Brg1 helicase, and this process is inhibited by Mhrt.

To test the ability of Brg1 to distinguish chromatinized from naked DNA promoters in cells, Myh6 promoter is cloned into the luciferase reporter plasmid pREP4 (allowing promoter chromatinization[55]) and pGL3 (containing naked, non-chromatinized promoter). In rat ventricular cardiomyocytes and SW13 cells, ChIP and luciferase analyses showed that Brg1 bound and repressed chromatinized but not naked Myh6 promoter (FIGS. 78 and 79 and FIGS. 95 and 96, described below). However, without D1/D2 domain or in the presence of Mhrt, Brg1 is unable to bind or repress chromatinized Myh6 promoter (FIGS. 80,81 and 82 and FIG. 97, described below), indicating the necessity of D1D2 for the interaction between Brg1, chromatin and Mhrt. Consistently, all our genetic, biochemical and cellular studies show that Brg1 requires the helicase domain to bind to chromatinized DNA targets, and Mhrt seizes the helicase to disrupt Brg1-chromatin binding.

Brg1 Outruns Mhrt to Bind to its Target Mhrt Promoter

How Brg1 surpassed its basal suppression by Mhrt to control Myh, Mhrt, Opn, or other genes to trigger cardiomyopathy (Supplementary Note) is examined. Amylose pull-down experiments showed that Brg1 dose-dependently escaped from Mhrt inhibition to occupy Mhrt promoter (FIGS. 98 and 99, described below). Brg1 protein, which increases under stress conditions,[41] could therefore outrun Mhrt and gain control over the Mhrt promoter to repress Mhrt expression and tip the balance towards Brg1. Contrary to the endogenous Mhrt that is repressible by Brg1, the Mhrt transgene (Tg779)—driven by Tnnt2/Tre promoters—is not subject to repression by Brg1 and is thus able to keep Mhrt at pre-stress levels to inhibit Brg1 and reduce hypertrophy. This further demonstrates the necessity of Mhrt repression for myopathy to develop.

Human MYH7 loci encoded RNA that resembled Mhrt in primary sequence and secondary structure, as predicted by minimal free energy.[65] (FIG. 83 and FIGS. 100 and 101, described below). Human MHRT is also repressed in stressed hearts, with 82.8%, 72.8% and 65.9% reduction of MHRT in hypertrophic, ischaemic or idiopathic cardiomyopathy tissues, respectively (FIG. 84 and FIG. 102, described below). This suggests a conserved MHRT mechanism of human cardiomyopathy.

Mhrt is the first example, to our knowledge, of a lncRNA that inhibits myopathy and chromatin remodellers. Reciprocal Mhrt-Brg1 inhibition constitutes a feedback circuit critical for maintaining cardiac function (FIG. 85). The helicase core of Brg1, combined with the histone-binding domains of the Brg1/BAF complex, adds a new layer of specificity control to Brg1/BAF targeting and chromatin remodeling (FIG. 86). The Mhrt-helicase interaction also exemplifies a new mechanism by which lncRNA controls chromatin structure. To further elucidate chromatin regulation, it will be essential to define helicase domain function in all ATP-dependent chromatin-remodeling factors and to identify new members of lncRNA that act through this domain to control chromatin. The cardioprotective Mhrt may have translational value, given that RNA can be chemically modified and delivered as a therapeutic drug. This aspect of lncRNA-chromatin regulation may also inspire new therapies for human disease.

The Binding Affinity of Mhrt-B is Essentially Identical to that of Full-Length Mhrt779

In pathologically stressed hearts, Brg1 are activated in cardiomyocytes, whereas Mhrt is repressed in cardiomyocytes. Brg1 activation is essential for cardiac hypertrophy and failure to develop. Restoring Mhrt level can protect the heart from stress-induced hypertrophy and failure. Mhrt functions by binding to the helicase domain of Brg1 to inhibit Brg1's chromatin targeting and gene regulation. It is an inhibitor of the pro-hypertrophic Brg1.

FIGS. 87, 88, 89 and 90 the region of Mhrt required for binding Brg1. FIG. 87 is Mountain plot of Mhrt779 predicted by RNA fold. Segments Mhrt-A, -B and -C are divided according to bases pairing probability calculated by three different methods: minimum free energy (mfe, red); partition function (pf, thermodynamic ensemble, green); centroid (blue). The plots are probability or height (axis) versus position on Mhrt779 (x axis, 1-779 nt), where the height is represented by the number of base pairs enclosing at that position. FIG. 88 shows MFE secondary structure of segments Mhrt-A, -B and -C. FIG. 89 shows EMSA of Mhrt-A, -B and -C and Brg1 helicase D1D2. MBP: maltose binding protein. D1D2: MBP fused to Brg1 D1D2 (aa 774-1310). The numbers represent molecular ratios between D1D2 and Mhrt segments. The black boxes highlight the bands with most dramatic differences. FIG. 90 shows binding affinity of Mhrt-A, -B and -C to Brg1 D1D2 determined by EMSA. Error bars represent the standard error from multiple independent measurements. Nonlinear regression curves were generated by GraphPad Prism.

To determine the region of Mhrt required for binding Brg1, Mhrt779 (SEQ ID NO: 1) is divided into three segments (A, B and C), based on base-pairing probability for RNA secondary structure by three different methods (green, blue, red curves of FIG. 87). Mhrt-B (SEQ ID NO: 2) has the highest probability of forming stable secondary structure, and this segment is conserved among all 7 identified Mhrt species. The predicted structure of Mhrt-A, B, C segments by minimal energy calculation (mfe) is shown in Response FIG. 88. By RNA-EMSA assay, Mhrt-B is found to have the highest binding affinity with Brg1 helicase (Kd=0.77 µM), ~2-2.5-folds of that of Mhrt-A (Kd=1.7 µM) or -C (Kd=1.5 µM)(FIGS. 89 and 90). The binding affinity of Mhrt-B (Kd=0.77 µM) is essentially identical to that of full-length Mhrt779 (Kd=0.76 µM), suggesting that segment Mhrt-B is the primary region of Mhrt779 required for binding to Brg1.

Accordingly, a 400 base pair fragment or segment (Mhrt-B) (SEQ ID NO: 2) is separated from the natural 779 base pair (bp) sequence of mouse Mhrt (SEQ ID NO: 1). Mhrt-B binds to Brg1 as well as Mhrt (SEQ ID NO: 1) and has the same cardioprotective effects as the 779 bp sequence of mouse Mhrt. Human MHRT (SEQ ID NO: 3) resembles mouse Mhrt779. A short fragment of human MHRT-B (SEQ ID NO: 4) that resembles the mouse Mhrt-B is also identified.

Embodiments of the present invention provide a composition comprising a long noncoding RNA that encompasses a modified myosin heavy-chain-associated RNA transcript (Mhrt). In one embodiment, the long noncoding RNA is a mouse Mhrt-B RNA comprising SEQ ID NO: 2. In an alternative embodiment, the long noncoding RNA comprises a human MHRT-B RNA comprising SEQ ID NO: 4.

Embodiments of the present invention provide a product comprising a nucleic acid encoding a modified Mhrt or additionally/alternatively modified Mhrt to be used to treat patients with heart failure. The modified Mhrt does not exist in human hearts or body. The modified Mhrt binds to a chromatin remodeler Brg1 to inhibit Brg1's genomic targeting and gene regulation function. Brg1 is activated by pathological stress to trigger cardiac myopathy and failure. The Mhrt protects the heart from myopathy and failure via inhibiting Brg1's gene regulation function.

Although the 400 base pair fragments having SEQ ID NO: 2 and SEQ ID NO: 4 are examples for treating pathological hypertrophy, it will be appreciated that other members of the cluster of the myosin heavy-chain-associated RNA transcripts can be modified and used for the treatment of pathological hypertrophy. The subject receiving such treatment is not limited to mice. Pathological hypertrophy is not limited to be induced by transaortic constriction (TCA). It could be any reason, including those unknown.

According to some embodiments, a composition disclosed herein may be delivered to a subject via injection. A composition of one or more modified species of the cluster of lncRNA transcripts Mhrt RNAs may be prepared in a dosage form of an injection fluid and be loaded into an injectable device (e.g., a syringe), to inject into a subject's body. FIG. 91 is an illustration of a treatment delivery apparatus (9100) comprising an injectable drug delivery device (9120) and a composition disclosed herein in the dosage form of an injection fluid (9110). The composition disclosed herein may be delivered through an injection through a wall (9150) of a body part or an organ (9140) of a subject and go into body part or organ (9140) of the subject. In select embodiments, the injectable drug delivery device may stay outside (9142) of body party or organ (9140) of the subject's body.

FIG. 91 represents merely one illustrative embodiment for delivering the disclosed pharmaceutical composition into a subject's body. The delivery instrument may not be limited to a syringe-type device. One of ordinary skill in the art would readily appreciate that any injectable device suitable for delivering the disclose product(s) or agent of a patient's body may be utilized according to aspects of the present invention.

Embodiments of the present invention provide a composition comprising a long noncoding RNA that encompasses a modified myosin heavy-chain-associated RNA transcript (Mhrt). The modified myosin heavy-chain-associated RNA transcript inhibits Brg1's genomic targeting and gene regulation function in a subject having the modified myosin heavy-chain-associated RNA transcript. In one embodiment, the long noncoding RNA comprises a modified mouse Mhrt-B RNA comprising SEQ ID NO: 2. In an alternative embodiment, the long noncoding RNA comprises a modified human MHRT-B RNA comprising SEQ ID NO: 4. In one embodiment, the composition comprises nanoparticles and the modified myosin heavy-chain-associated RNA is packaged with the nanoparticles.

Embodiments of the present invention also provide a product encompassing at least one dosage of a pharmaceutical composition that comprises one or more long noncoding RNAs to treat pathological hypertrophy. The one or more long noncoding RNAs comprise one or more modified myosin heavy-chain-associated RNA transcripts. Each of the one or more modified myosin heavy-chain-associated RNA transcripts binds to Brg1 to inhibit Brg1's genomic targeting and gene regulation function. In one embodiment, the one or more modified myosin heavy-chain-associated RNA transcripts comprise a mouse Mhrt-B RNA comprising SEQ ID NO: 2. In an alternative embodiment, the one or more modified myosin heavy-chain-associated RNA transcripts comprise a modified human MHRT-B RNA comprising SEQ ID NO: 4. In one embodiment, the pharmaceutical composition comprises nanoparticles and the one or more modified myosin heavy-chain-associated RNAs are packaged with the nanoparticles.

In some embodiments, a product is a pharmaceutical composition. This pharmaceutical composition encompasses one or more vectors in which RNA expression cassettes are incorporated for expressing long noncoding RNAs. A RNA expression cassette encompasses an inducible promoter and a DNA fragment that has a sequence that is complementary to a sequence of a long noncoding RNA. The long noncoding RNA may be any modified myosin heavy-chain-associated RNA transcript, for example, a mouse Mhrt-B RNA comprising SEQ ID NO: 2, a human MHRT-B RNA comprising SEQ ID NO: 4, etc. The inducible promoter controls the expression of the long noncoding RNA. For example, the vector may be transferred into a suitable host cells. Under induction of the promoter, the cells' mechanism is commandeered to produce the modified myosin heavy-chain-associated RNA that has a sequence being complementary to the DNA fragment regulated by the inducible promoter. In one embodiment, the inducible promoter is a tetracycline response element. In one embodiment, the modified myosin heavy-chain-associated RNA transcript in cardiomyocytes of a subject administered with the pharmaceutical composition is expressed under an induction of doxycycline treatment.

Accordingly, some embodiments disclosed herein provide modified Mhrt transcripts that bind to a chromatin remodeler Brg1 and inhibit Brg1's genomic targeting function. In some embodiments, the modified Mhrt RNAs comprise a 400 base pair fragment (Mhrt-B) that is divided from the natural 779 base pair sequence of Mhrt and has a sequence of SEQ ID NO: 2. In some embodiments, a modified Mhrt RNAs transcript comprise a short fragment RNA MHRT-B that has a sequence of SEQ ID NO: 4. Either Mhrt-B of SEQ ID NO: 2 or MHRT-B of SEQ ID NO: 4 has the same cardioprotective effects as Mhrt 779.

Embodiments also provide a composition comprising a vector encompassing a inducible promoter and a DNA fragment that comprise a sequence complementing to the sequence of Mhrt-B of SEQ ID NO: 2, wherein a transcription of Mhrt-B RNA fragment is controlled by the promoter. Upon induction, a Mhrt-B RNA of SEQ ID NO: 2 will be synthesized by transcription. The vector disclosed herein may be used for delivering a long noncoding RNA such as Mhrt-B of SEQ ID NO: 2 into a subject for treating pathological hypertrophy. The vector disclosed herein may also be used for generating a long noncoding RNA such as Mhrt-B of SEQ ID NO: 2 in vitro. Mhrt-B of SEQ ID NO: 2 generated in vitro may be further isolated and purified.

Embodiments also provide a composition comprising a vector encompassing an inducible promoter and a DNA fragment that comprises a sequence complementing to the sequence of MHRT-B of SEQ ID NO: 4, wherein a transcription of MHRT-B RNA fragment is controlled by the inducible promoter. Upon induction, an RNA fragment having a sequence of SEQ ID NO: 4 will be synthesized by the transcription. The vector disclosed herein may be used for delivering a long noncoding RNA such as MHRT-B of SEQ ID NO: 4 into a subject for treating pathological hypertrophy. The vector disclosed herein may also be used for generating a long noncoding RNA such as MHRT-B having a sequence of SEQ ID NO: 4 in vitro. MHRT-B of SEQ ID NO: 4 generated in vitro may be further isolated and purified.

According to some embodiment disclosed herein, a therapeutically effective amount of a pharmaceutical composition may be administered to a subject for treating pathological hypertrophy, wherein the pharmaceutical composition comprises one or more isolated RNAs selected from a cluster of long noncoding RNA transcripts Mhrt RNAs. In one embodiment, the one or more isolated RNAs in the pharmaceutical composition comprise MHRT-B of SEQ ID NO: 4. In one embodiment, the one or more isolated RNAs in the pharmaceutical composition comprise Mhrt-B of SEQ ID NO: 2. In one embodiment, the one or more isolated RNAs are packaged with nanoparticles.

FIG. 92 illustrates sequence alignment and motif analysis. Alignment and motif analysis are used to generate schematics of an architecture of mouse Brg1 and the sequence alignment of Brg1, Vasa (fruit fly), Rad54 (zebrafish, sulfolobus, solfataricus) and Chd1 (yeast). The motifs are outlined by blue boxes (D1 domain) and purple boxes (D2 domain).

FIGS. 93, 94, 95, 96, 97, 98, 99, 100, 101 and 102 are a set of graphs and images of Coomassie blue staining illustrate purification of Brg1 helicase core domains and EMSA of naked Myh6 promoter, ChIP and reporter studies in SW13 cells. FIG. 93 is a Coomassie blue staining of purified MBP-tagged Brg1 helicase domains. Bovine serum albumin (BSA) was loaded as a control. FIG. 94 is an EMSA assay of naked Myh6 promoter (2426 to 1170) with helicase domains of Brg1. Probe: biotin-labelled Myh6 promoter. 50 mM of MBP, MBP-D1, MBP-D2, and MBP-D1D2 proteins are used for EMSA. FIG. 95 is a ChIP analysis of Brg1 on chromatinized (episomal) and naked Myh6 promoter in SW13 cells. FIG. 96 is a luciferase reporter analysis of Brg1 on chromatinized (episomal) and naked Myh6 promoter in SW13 cells. In FIGS. 95 and 96, GFP=green fluorescent protein control. FIG. 97 is an analysis of the luciferase reporter of helicase-deficient Brg1 on chromatinized (episomal) Myh6 promoter in SW13 cells. DD1: Brg1 lacking amino acids 774-913. DD2: Brg1 lacking amino acids 1086-1246. ChIP: H-10 antibody recognizing N terminus, non-disrupted region of Brg1. P values: Student's t-test. Error bars show s.e.m.

FIGS. 98 and 99 are a set of an image and a graph illustrating that Brg1 outruns Mhrt to bind to its target Mhrt promoter. FIG. 98 shows assembly of nucleosomes on the Mhrt promoter (a3/4). FIG. 99 shows an amylose pull-down assay: amylose is used to pull down the chromatinized Mhrt promoter that is incubated with various doses of MBP and MBP-Brg1 D1D2. DNA precipitated by amylose is further quantified by qPCR. P values: Student's t-test. Error bars show s.e.m.

FIGS. 100, 101 and 102 illustrate sequence alignment and secondary structure prediction of human and mouse MHRT, and demography of heart transplantation donors. FIG. 100 shows sequence alignment of human MHRT (SEQ ID NO: 74) and mouse Mhrt779 (SEQ ID NO: 75). FIG. 101 shows predicted secondary structure of mouse Mhrt779 and human MHRT, using minimal free energy (MFB) calculation of RNAfold WebServer. FIG. 102 shows Demography of human subjects whose tissues were used for RT-qPCR analysis (FIG. 84). ICM, ischaemic cardiomyopathy; IDCM, idiopathic cardiomyopathy; LVH, left ventricular hypertrophy.

In one embodiment, the present invention provides a composition comprising a nucleic acid encoding a modified myosin heavy-chain-associated RNA transcript. The modified myosin heavy-chain-associated RNA transcript inhibits Brg1's genomic targeting and gene regulation function in a subject to whom the composition is administered. In one embodiment, the modified myosin heavy-chain-associated RNA transcript may comprise SEQ ID NO: 2. In one embodiment, the modified myosin heavy-chain-associated RNA transcript may comprise SEQ ID NO: 4.

In one embodiment, the present invention, the nucleic acid may be incorporated into a vector. In one embodiment, the vector may comprise an expression cassette comprising a promoter operably linked to the nucleic acid encoding the modified myosin heavy-chain-associated RNA transcript. The promoter may direct an expression of the nucleic acid to produce modified myosin heavy-chain-associated RNA transcript. In one embodiment, the promoter may comprise an inducible promoter. In one embodiment, the promoter may comprise a tetracycline response element.

In one embodiment, the present invention provides an organism comprising a transgene comprising a promoter and a nucleic acid encoding a modified myosin heavy-chain-associated RNA transcript. The promoter regulates an expression of the nucleic acid to produce the modified myosin heavy-chain-associated RNA transcript in the organism. The modified myosin heavy-chain-associated RNA transcript inhibits Brg1's genomic targeting and gene regulation function in the organism. In one embodiment of the present invention, the transgene may be incorporated into a genome DNA of the organism. In one embodiment of the present invention, the modified myosin heavy-chain-associated RNA transcript may comprise SEQ ID NO: 2. In one embodiment, the promoter may comprise a Tre promoter. In one embodiment of the present invention, the modified myosin heavy-chain-associated RNA transcript may comprise SEQ ID NO: 4. In one embodiment of the present invention, the promoter may comprise an inducible promoter. In one embodiment of the present invention, the promoter may comprise a tetracycline response element.

In one embodiment of the present invention, the organism may comprise a non-human animal. In one embodiment of the present invention, the organism may comprise a transgene mouse. In one embodiment of the present invention, the promoter may comprises a tetracycline response element, and the nucleic acid may express the modified myosin heavy-chain-associated RNA transcript in cardiomyocytes of the transgene mouse under an induction of doxycycline treatment. In one embodiment, the transgene mouse is Tnnt2-rtTA; Tre-Mhrt mouse line that contains two transgenes, Tnnt2-rtTA and Tre-Mhrt. The Tnnt2-rtTA transgene allows cardiac specific expression reverse tetracycline-controlled transactivator protein. The Tre-Mhrt transgenic construct expresses the modified myosin heavy-chain-associated RNA transcript under the control of tetracycline-responsive element (TRE). In the presence of tetracycline or a tetracycline analog (such as doxycycline), expression of modified myosin heavy-chain-associated RNA transcript is observed in the nuclei of cardiacmyocytes.

In one embodiment, the present invention provides a method comprising administering to a subject in need of a composition comprising a nucleic acid encoding a modified myosin heavy-chain-associated RNA transcript to express the modified myosin heavy-chain-associated RNA transcript in the subject. The modified myosin heavy-chain-associated RNA transcript inhibits Brg1's genomic targeting and gene regulation function in the subject. In one embodiment of the present invention, the composition may comprise a vector and the nucleic acid encoding the modified myosin heavy-chain-associated RNA transcript may be incorporated in the vector. In one embodiment of the present invention, the vector may comprise an expression cassette comprising a promoter operably linked to the nucleic acid encoding the modified myosin heavy-chain-associated RNA transcript, and the promoter may direct an expression of the nucleic acid to produce the modified myosin heavy-chain-associated RNA transcript. In one embodiment, the modified myosin heavy-chain-associated RNA transcript may comprise SEQ ID NO: 2. In one embodiment, the modified myosin heavy-chain-associated RNA transcript may comprise SEQ ID NO: 4. In one embodiment of the present invention, the nucleic acid may be incorporated into a genome DNA of the subject. In one embodiment of the present invention, the promoter may comprise an inducible promoter. In one embodiment of the present invention, the promoter may comprise a tetracycline response element. In one embodiment of the present invention, the nucleic acid may express the modified myosin heavy-chain-associated RNA transcript in cardiomyocytes of the subject under an induction of doxycycline treatment. In one embodiment of the present invention, the composition may be administered to the subject with a pharmaceutical carrier. In one embodiment, the composition comprises nanoparticles. The nucleic acid encoding a modified myosin heavy-chain-associated RNA transcript is packaged in the nanoparticles for delivery into a subject. In one embodiment of the present invention, the composition may be administered to the subject via injection. The compositon can be delivered through intracardiac or intravenously injection. For example, intracardiac injections may be used in an emergency if the intravenous injection approach is ineffective.

In one embodiment, the present invention provides a treatment delivery apparatus comprising a device and at least one dosage of a composition contained in the device. The composition comprises a nucleic acid encoding a modified myosin heavy-chain-associated RNA transcript. The modified myosin heavy-chain-associated RNA transcript inhibits Brg1's genomic targeting and gene regulation function in a subject to whom the composition is administered. In one embodiment of the present invention, the composition in the device may comprise a vector, and the nucleic acid encoding the modified myosin heavy-chain-associated RNA transcript may be incorporated in the vector. In one embodiment of the present invention, the vector may comprise an expression cassette comprising a promoter operably linked to the nucleic acid encoding the modified myosin heavy-chain-associated RNA transcript, and the promoter may direct an expression of the nucleic acid to produce the modified myosin heavy-chain-associated RNA transcript. In one embodiment of the present invention, the modified myosin heavy-chain-associated RNA transcript may comprise SEQ ID NO: 2. In one embodiment of the present invention, the modified myosin heavy-chain-associated RNA transcript may comprise SEQ ID NO: 4. In one embodiment, the modified myosin heavy-chain-associated RNA transcript is packaged with nanoparticles.

Having described the many embodiments of the present invention in detail, it will be apparent that modifications and variations are possible without departing from the scope of the invention defined in the appended claims. Furthermore, it should be appreciated that all examples in the present disclosure, while illustrating many embodiments of the invention, are provided as non-limiting examples and are, therefore, not to be taken as limiting the various aspects so illustrated.

EXAMPLES

Example 1

Methods Summary

Sm22α-cre, Brg1$^{f/f}$, Mef2c-cre, R26R and Tnnt2-rtTA; Tre-cre mice are described in references.[23,24,27,31,38] Immunostaining, RNA in situ hybridization, quantitative RT-PCR and whole embryo culture are performed as described in references.[23,26] TAC is modified from previous descriptions.[20] The pressure load caused by TAC is verified by the pressure gradient across the aortic constriction measured by echocardiography. Curve modelling is performed with the Levenburg-Marquardt nonlinear regression method and XLfit software.

Rapid amplification of cDNA ends (RACE), RNA in situ hybridization, RT-qPCR, codon substitution frequencies (CSF), echocardiography, northern blot, EMSA, ChIP, RNA immunoprecipitation, reporter assay, nucleosome assembly, and the amylose pull-down assay are performed as described in references.[41,42,64]

Mice, Animal Sample Size, and Randomization

For the generation of Tg779 mice, Mhrt779 is cloned into the pTRE2 backbone (CLONETECH). A DNA fragment containing the Tre promoter and Mhrt779 is injected into the pronucleus of fertilized oocytes (B6C3H/F1). Embryos are implanted into a pseudopregnant CD-1 mouse. The Tre-Mhrt779 transgene is identified by PCR genotyping using primers CGCCTGGAGACGCCATCCAC (SEQ ID NO: 5) and TGTCTTCAAAGCTGACTCCCT (SEQ ID NO: 6). Tre-Mhrt779 mice with ~3 copies of the transgene are backcrossed with Tnnt2-rtTA mice as described previously[41,66] to generate Tnnt2-rtTA;Tre-Mhrt779 (Tg779) mice. The number of animals used (n) is denoted in each test in the figures, including technical replicates when applicable. Mouse littermates are routinely used to control and perform the experiments. Each subgroup of experiments has n=3 to 14 biological replicates, many of which have technical replicates of three. Assignment to each experimental subgroup is based on genotypes. Littermate mice with the same genotypes regardless of gender are randomly selected from the cage and assigned to different control and experimental subgroups. Major procedures are blinded. The use of mice for studies is in compliance with the regulations of Indiana University, Stanford University and the National Institutes of Health.

RACE and Cloning of Full Length of Mhrt Transcripts

The 3' and 5' RACE are performed using the FIRSTCHOICE® RLM-RACE Kit (AMBION®) following the manufacturer's instruction. RNA is extracted from adult heart ventricles. Primers used for 3' and 5' RACE are designed based on the known sequence information: TCAT-TGGCACGGACAGCATC (SEQ ID NO: 7) (first-round Mhrt 3'-prime specific) and GAGCATTTGGGGATGG-TATAC (SEQ ID NO: 8) (second-round Mhrt 3'-prime specific); CAAACATTTTCATTTTCCTCTTT (SEQ ID NO: 9) (first-round Mhrt 5'-prime specific) and TCTGCT-TCATTGCCTCTGTTT (SEQ ID NO: 10) (second-round Mhrt 5'-prime specific). Once the 5' and 3' cDNA ends are reached, primers F1 (FIG. 43; AAGAGCCCTACAGTCT-GATGAACA) (SEQ ID NO: 11) and R1 (FIG. 43; CCT-TCACACAAACATTTTATTT) (SEQ ID NO: 12) are used to amplify the full-length Mhrt transcripts and cloned them into pDRIVE TA cloning vector (QIAGEN®) for sequencing. Mhrt RNAs are also further cloned into shuttle vector pAdd2[67,68] for expression in cells.

Northern Blot and In Situ Hybridization.

5 μg of total RNA using QUICK-RNA Mini Kit (ZYMO RESEARCH) is obtained. RNA blot is performed using NORTHERN-MAX Kit (AMBION®) following the manufacturer's protocol. Single-stranded RNA probe is generated by in vitro transcription with MAXISCRIPT SP6/T7 kit (AMBION®) with ATP [α-$^{32}$P] (PERKINELMER) using full-length Mhrt779, Myh6 and Myh7 as the template and followed by digestion with DNase I (AMBION®). Hybridization is performed at 65° C. The blot is washed and imaged by Phosphor storage scanning by TYPHOON 8600 Imager (GE HEALTHCARE). In situ hybridization experiments are performed as previously described.[41,69]

RNA Fractionation

To isolate cytosolic and nuclear RNAs from adult heart tissues, a PARIS kit (AMBION®) is used and followed the manufacturer's instruction. Ten milligrams of tissue are homogenized in cell fractionation buffer thoroughly before centrifuging for 5 min at 500 g. Supernatant is collected as the cytosolic fraction, while the nuclear pellet is washed and lysed by cell disruption buffer. Such samples are further mixed with 2× lysis/binding solution before extracting RNA using the manufacturer's protocol.

Codon Substitution Frequency Predication

To measure the coding potential of Mhrt, the previously described codon substitution frequencies (CSF) method[42,43] is used to evaluate the evolutionary characteristics in their alignments with orthologous regions in six other sequenced mammalian genomes (rat, human, hamster, rhesus monkey, cat and dog). CSF generates a likelihood score for a given sequence considering all codon substitutions observed within its alignment across multiple species, which is based on the relative frequency of similar substitutions occurring in known coding and noncoding regions. CSF compares two empirical codon models; one generated from alignments of known coding regions and the other according to noncoding regions, producing a likelihood ratio. The ratio reflects whether the protein-coding model better explains the alignment.

Ribosome Profiling and RNA Deep Sequencing

For ribosome profiling,[44] over-expression of the predominant species of Mhrt (Mhrt779) along with HOTAIR are achieved through co-transfecting pAdd2-779 and pAdd2-HOTAIR into SW13 cells. The cells are then lysed to extract ribosome-associated RNA fragments using ARTSEQ Ribosome Profiling Kit (Epicentre, Illumina) The RNA fragments are further converted into a DNA library through end repair, adaptor ligation, reverse transcription circularization, and PCR amplification. A conventional RNA-seq library is also prepared, with total RNA extracted from those cells with an miRNeasy Mini Kit (QIAGEN® #217004). The libraries are further processed according to a MISEQ Sample Prep sheet, and a MISEQ 50 cycle kit is used for sequencing. PCR products (1.25 pmol) are used for sequencing. Approximately 600,000-700,000 reads are properly paired and used for further analysis. The resulting reads are aligned to the human hg19 or mouse mm10 genome using BOWTIE2 v.2.0.0.6.[70] Mapped reads are visualized on the UCSC browser as bigwig files generated using SAMTOOLS v.0.1.18,[71] BEDTOOLS v.2.16.1,[72] BEDCLIP and BEDGRAPHTOBIGWIG. For quantification of fragments per kilobase of exon per million fragments mapped (FPKM) values, cuffdiff as part of the tophat suite v.2.0.8b[73] is run on a merged bam file containing the human and the Mhrt reads using a custom gtf file comprising the human hg19 iGenome and the Mhrt transcripts. To generate scatter plots of the genes, cuffdiff files are used for visualization with cummerbund v.2.3.1.[73]

In Vitro Translation and Biotin Labelling

TNT QUICK COUPLED Transcription/Translation System (PROMEGA) is used for in vitro translation. Briefly, 1 µg plasmids of control (luciferase) and various Mhrt species inserted into a pDrive vector are added to 40 µl rabbit reticulocyte lysates containing $^{35}$S-methionine. After 1 h of incubation, the reactions are analyzed on 10-20% Tris-Tricine gel. The gel is dried and visualized by the TYPHOON 8600 Imager (GE HEALTHCARE). Biotin-NTP is added to the in vitro translation reaction. Total RNAs are extracted and the biotin-labelled RNAs are detected subsequently by IRDYE 680 Streptavidin (Li—COR, 926-68079) using an ODYSSEY Infrared Imaging System.

TAC

The TAC surgery is performed as described[41] on adult mice of 8-10 weeks of age and between 20 and 25 g in weight. Mice are fed with doxycycline food pellets (6 mg doxycycline per kg of food; Bioserv) 7-14 days before the TAC operation. Mice are anaesthetized with isoflurane (2-3%, inhalation) in an induction chamber and then intubated with a 20-gauge intravenous catheter and ventilated with a mouse ventilator (Minivent, Harvard Apparatus). Anesthesia is maintained with inhaled isoflurane (1-2%). A longitudinal 5 mm incision of the skin is made with scissors at the midline of sternum. The chest cavity is opened by a small incision at the level of the second intercostal space 2-3 mm from the left sternal border. While opening the chest wall, the chest retractor is gently inserted to spread the wound 4-5 mm in width. The transverse portion of the aorta is bluntly dissected with a curved forceps. Then, 6-0 silk is brought underneath the transverse aorta between the left common carotid artery and the brachiocephalic trunk. One 27-gauge needle is placed directly above and parallel to the aorta. The loop is then tied around the aorta and needle, and secured with a second knot. The needle is immediately removed to create a lumen with a fixed stenotic diameter. The chest cavity is closed by 6-0 silk suture. Sham-operated mice underwent similar surgical procedures, including isolation of the aorta and looping of the aorta, but without tying of the suture. The pressure load caused by TAC is verified by the pressure gradient across the aortic constriction measured by echocardiography. Only mice with a pressure gradient>30 mm Hg are analyzed for cardiac hypertrophy, echocardiography and other purposes.

Echocardiography

The echocardiographer is blinded to the genotypes and surgical procedure. Transthoracic ultrasonography is performed with a GE VIVID 7 ultrasound platform (GE Health Care) and a 13 MHz transducer is used to measure aortic pressure gradient and left ventricular function. Echocardiography is performed on control and Tnnt2-rtTA;Tre-Mhrt779 (Tg779) mice at designated time points after the TAC procedure. To minimize the confounding influence of different heart rates on the aortic pressure gradient and left ventricular function, the flow of isoflurane (inhalational) is adjusted to anaesthetize the mice while maintaining their heart rates at 450-550 beats per minute. The peak aortic pressure gradient is measured by continuous-wave Doppler across the aortic constriction. Left ventricular function is assessed by M-mode scanning of the left ventricular chamber, standardized by two-dimensional, short-axis views of the left ventricle at the mid papillary muscle level. Left ventricular chamber size and wall thickness are measured in at least three beats from each projection and averaged. Left ventricular internal dimensions at diastole and systole (LVIDd and LVIDs, respectively) are measured. The fractional shortening (FS) of the left ventricle is defined as 100%×(1−LVIDs/LVIDd), representing the relative change of left ventricular diameters during the cardiac cycle. The mean FS of the left ventricle is determined by the average of FS measurements of the left ventricular contraction over five beats. P values are calculated by Student's t-test. Error bars indicate s.e.m.

Histology, Trichrome Staining and Morphometric Analysis of Cardiomyocytes

Histology and trichrome staining are performed as described.[23,26] Trichrome stain (Masson) kit (Sigma) is used and the manufacturer's protocol is followed. For morphometric analysis of cardiomyocytes, paraffin sections of the heart are immunostained with a fluoresecin isothiocyanate-conjugated wheat germ agglutinin (WGA) antibody (F49, Biomeda) that highlighted the cell membrane of cardiomyocytes. Cellular areas outlined by WGA are determined by the number of pixels enclosed using ImageJ software (NCBI). Approximately 250 cardiomyocytes of the papillary muscle at the mid-left ventricular cavity are measured to determine the size distribution. P values are calculated by Student's t-test. Error bars indicate s.e.m.

RT-qPCR and Strand-Specific Reverse Transcription PCR Analysis

RT-qPCR analyses are performed as described.[41,23] The following primer sequences (listed later) are used. RT-qPCR reactions are performed using SYBR green master mix (BioRad) with an EPPENDORF realplex, and the primer sets are tested to be quantitative. Threshold cycles and melting curve measurements are performed with software. P values are calculated by Student's t-test. Error bars indicate s.e.m. To conduct strand-specific RT-PCR analysis, human total RNA and Superscript III First-Strand Synthesis System (Invitrogen) is used. Primers R1 (FIG. 83); CTACAGAAT-GAGATCGAGGACT (SEQ ID NO: 13) and R2 (FIG. 83; GGGGCTGAAGAGTGAGCCTT (SEQ ID NO: 14)) are designed based on known sequence and are used for individual RTs, respectively. To detect MHRT, primers F1 (FIG. 83; CTGGAGCTGGGACAGGTCAGCA (SEQ ID NO: 15)) and R1 are used. These primers could also amplify endogenous MYH7 and thus serve as controls. Primers F2 (FIG. 83; TGGGGAACACGGCGTTCTTGA (SEQ ID NO: 16)) and R2 are used to specifically amplify MHRT and used in RT-qPCR analysis.

PCR primers for RT-qPCR of mRNA are as follows. Mouse TfIIb-F, CTCTGTGGCGGCAGCAGCTATTT (SEQ ID NO: 17), mouse TfIIb-R,CGAGGGTAGATCAGTCTG-TAGGA (SEQ ID NO: 18); mouse Hprt1-F, GCTGGT-GAAAAGGACCTCT (SEQ ID NO: 19), mouse Hprt1-R, CACAG GACTAGAACA CCTGC (SEQ ID NO: 20); mouse Anf-F, GACTAGGCTGCAACAGCTTCCG (SEQ ID NO: 21), mouse Anf-R, GCCACAGTGGC AATGT-GACCAA (SEQ ID NO: 22); mouse Serca2a-F, CATTTG-CATTGCAGTCTGGAT (SEQ ID NO: 23), mouse Serca2a-

R, CTTTGCCATCCTACGAGTTCC (SEQ ID NO: 24); mouse Tnnt2-F, TACAGACTCTGATCGAGGCTCACTTC (SEQ ID NO: 25), mouse Tnnt2-R, TC ATTGC-GAATACGCTGCTGCTC (SEQ ID NO: 26); mouse Mhrt-F (common), GAGC ATTTGGGGATGGTATAC (SEQ ID NO: 27), mouse Mhrt-R (common), TCTGCTTCATTGC-CTCTGTTT (SEQ ID NO: 28); mouse Mhrt779-F, TCTG-GCCACAGCCCGCAGCTTC (SEQ ID NO: 29), mouse Mhrt779-R, AGTCATGTAT ACCATCCCAA (SEQ ID NO: 30); Mouse Neat1-F, TCTCCTGGAGCCACATC TCT (SEQ ID NO: 31), mouse Neat1-R, GCTTTTCCTTAGGC-CCAAAC (SEQ ID NO: 32); mouse 28S-rRNA-F, GGTAGCCAAATGCCTCGTCAT (SEQ ID NO: 33), mouse 28S-rRNA-R, CCCTTGGCTGTGGTTTCG (SEQ ID NO: 34); human TFIIB-F, ACCACCCCAATGG ATGCAGACAG (SEQ ID NO: 35), human TFIIB-F, ACGGGCTAAGCGTCTGGCAC (SEQ ID NO: 36); human MHRT-F (F2), TGGGGAACACGGCGTTCTTGA (SEQ ID NO: 37), human MHRT-R (R2), GGGGCT-GAAGAGTGAGCCTT (SEQ ID NO: 38); human HOTAIR-F, GGTAGAAAAAGCAACCACGAAGC (SEQ ID NO: 39), human HOTAIR-R, ACAT AAACCTCTGTCT-GTGAGTGCC (SEQ ID NO: 40); human GAPDH-F, CCGGGAAACTGTGGCGTGATGG (SEQ ID NO: 41 human GAPDH-R, AGGTGGAGGAGTGGGTGTCGCT-GTT (SEQ ID NO: 42).

ChIP-qPCR

ChIP assay is performed as described[3] with modifications. Briefly, chromatin from hearts or SW13 cells is sonicated to generate average fragment sizes of 200-600 bp, and immunoprecipitated using anti-BRG1 J1 antibody,[3,40] anti-Brg1 H-10 antibody (Santa Cruz Biotechnology, against 115-149 amino acids of N terminus Brg1), anti-RNA polymerase II (Pol II) antibody (ab24759, Abcam), anti-H3K4me3 antibody (07-473, Millipore), anti-H3K36me3 antibody (17-10032, Millipore) or normal control IgG. Isolation and purification of immunoprecipitated and input DNA are done according to the manufacturer's protocol (Magna ChIP Protein G Magnetic Beads, Millipore), and qPCR analysis of immunoprecipitated DNA are performed. ChIP-qPCR signal of individual ChIP reactions is standardized to its own input qPCR signal or IgG ChIP signal. PCR primers (listed later) are designed to amplify the promoter regions of mouse Myh6 (−426, −320), mouse Myh7 (−102, +58), mouse Shh (−7142, −6911), mouse Vegfa (+1, +150) human GAPDH (−45, +121). The DNA positions are denoted relative to the transcriptional start site (+1).

PCR primers for ChIP-qPCR are as follows. Mouse ChIP-Myh6 promoter-F, GCAGATAGCCAGGGTTGAAA (SEQ ID NO: 43), mouse ChIP-Myh6 promoter-R, TGGG-TAA GGGTCACCTTCTC GCAGATAGCCAGGGTT-GAAA (SEQ ID NO: 44); mouse ChIP-Myh7 promoter-F, GTGACAACAGCCCT TTCTAAAT (SEQ ID NO: 45), mouse ChIP-Myh7 promoter-R, CTCCAGCTCCCACTC-CTACC (SEQ ID NO: 46); mouse ChIP-Shh promoter-F, GAGAACATTACAGGGTAGGAA (SEQ ID NO: 47), mouse ChIP-Shh promoter-R, GAAGCAGTGAGGTTG-GTGG (SEQ ID NO: 48); mouse ChIP-Vegfa promoter-F, CAAATCCCAGAGCACAGACTC (SEQ ID NO: 49), mouse ChIP-Vegfa promoter-R, AGCGCAG AGGCT-TGGGGCAGC (SEQ ID NO: 50); human ChIP-GAPDH promoter-F, TACTAGCGGTTTTACGGGCG (SEQ ID NO: 51), human ChIP-GAPDH promoter-R, TCGAACAGGAG-GAGCAGAGAGCGA (SEQ ID NO: 52).

RNA Immunoprecipitation

RNA immunoprecipitation (RNA-IP, RIP) is conducted as described[42] with some modifications. Briefly, P1 hearts, sham hearts or those from mice that had undergone TAC, or SW13 cells are crosslinked and lysed with lysis buffer (10 mM HEPES pH 7.5, 85 mM KCl, 0.5% NP-40, 1 mM dithiothreitol (DTT), 1× protease inhibitor) for tissues or lysis buffer (10 mM Tris-HCl pH 8.1, 10 mM NaCl, 1.5 mM MgCl2, 0.5% NP-40, 1 mM DTT, 1× protease inhibitor) for cells. Nuclei are isolated and sonicated using BIORUPTOR (DIAGENODE) (30 s on, 30 s off, power setting H, 5 mM, performed twice) in nuclear lysis buffer (50 mM Tris-HCl pH 8.1, 150 mM NaCl, 0.1% NP-40, 1 mM DTT, protease inhibitor, ribonuclease inhibitor). The nuclear extract is collected and incubated with primary antibodies at 4° C. overnight together with Manga ChIP Protein G Magnetic Beads (MILLIPORE). The beads are washed by wash buffer I (20 mM Tris-Hcl pH 8.1, 150 mM NaCl, 1% Triton X-100 and 0.1% SDS) three times, and wash buffer II (20 mM Tris-Hcl pH 8.1, 500 mM NaCl, 1% Triton X-100 and 0.1% SDS) three times. Beads are then resuspended in 150 ml 150 mM RIPA (50 mM Tris pH 7.5, 150 mM NaCl, 1 mM EDTA, 0.1% SDS, 1% NP-40, 0.5% sodium deoxycholate) with 5 µl Proteinase K and incubated for 1 h at 65° C. 1 ml of TRIZOL® is added to the sample, and RNA is extracted using the QUICK-RNA Mini Kit with the on-column DNase I digest (ZYMORESEARCH). RT and qPCR are then conducted with the purified RNA. The antibodies used for the immunoprecipitation are anti-BRG1 J1 antibody,[41,74] EZH2 (ACTIVE MOTIF),[75] SUZ12 (BETHYL LABORATORIES)[75,76] and normal IgG control.

Reporter Assay and Truncation of the Mhrt Promoter

For the Mhrt promoter reporter assay, plasmid is constructed by inserting ~2.5 kb mouse Mhrt promoter into the episomal pREP4-Luc plasmid[41,55,23,77] through cloning the PCR-amplified region of the promoter by using primers ACCGGCCTGAACCCCACTTCC (SEQ ID NO: 53) and ATGTCGAGACAGGGAACAGAA (SEQ ID NO: 54). Mouse Myh6 (−426 to +170, based on new genome annotation) and Myh7 (−3561 to +222) reporter constructs are described previously.[41] These vectors are transfected into rat neonatal cardiomyocytes or SW13 cells using LIPO-FECTAMINE® 2000 (INVITROGEN) along with plasmids expressing mouse Brg1 (actin-mBrg1-IRES-eGFP) or a matching empty vector plasmid (gifts from G. Crabtree) as well as an episomal Renilla luciferase plasmid (pREP7-RL) to normalize transfection efficiency. The transfected cells are cultured for 48 h and harvested for luciferase assay using the dual luciferase assay kit (PROMEGA). For naked DNA reporter, mouse Myh6 promoter (−426 to +170) is inserted in pGL3 vector (PROMEGA), and Renilla luciferase plasmid phRL-SV40 (gifts from J. Chen) is used as a normalizer. Dual luciferase assay is performed according to the manufacturer's instruction 48 h after transfection. For deletional analysis of the Mhrt promoter, various regions of the promoter are deleted from the full-length pREP4-Mhrt. The constructs are further analyzed by transfecting into SW13 cells.

RNA-EMSA and Kd Calculation

Biotin-labelled RNA probe is generated by in vitro transcription with MAXISCRIPT SP6/T7 kit (AMBION®) with biotin labelling NTP mixture (ROCHE) using linearized pDRIVE-Mhrt779 construct as the template and followed by digestion with DNase I (AMBION®). EMSA is performed by using the LIGHTSHIFT CHEMILUMINESCENT RNA EMSA KIT (THERMO SCIENTIFIC). The labelled probe is incubated with appropriate amounts of recombinant proteins in 10 µl in the 1× binding buffer (10 mM HEPES-KOH, pH 7.3, 10 mM NaCl, 1 mM MgCl2, 1 mM DTT) with 5 µg tRNA carrier at room temperature for 30 min. The reactions are then loaded onto 1% 0.5×TBE agarose gel and transferred to BrightStar-Plus positive charged membrane. The biotin-labelled probes are detected and quantified subsequently by IRDye 680 Streptavidin (Li—COR, 926-32231) using Odyssey Infrared Imaging System. The shifted signals are quantified and plotted against amount of the MBP, MBP-D1, MBP-D2 and MBP-D1D2 proteins using a previously described method[26] with GRAPHPAD PRISM (GRAPHPAD). The software facilitates the fitting of non-linear regression model and calculation of Kd values based on the fitting curve. The errors and $r^2$ values are also generated from the fitting curve.

Protein Expression and Purification of Brg1 Helicase Domains

To generate MBP fusion proteins of mouse Brg1 helicase domains, the DExx-box domain (D1) (amino acids 774-913 of Brg1), helicase-C domain (D2) together with C-terminal extension (CTE) (amino acids 1086-1310 of Brg1), as well as the entire helicase region (D1D2) (774-1310) are amplified by PCR and cloned into pMAL vector. MBP fusion proteins are induced by isopropyl-b-D-thiogalactoside (IPTG) and purified by amylose resin (E8021S, NEB).

Nucleosome Assembly and Amylose Pull-Down

Nucleosome assembly is per-formed by using EPIMARK Nucleosome Assembly Kit (E53505, NEB) following the manufacturer's instruction.[64] In brief, recombinant human core histone octamer, which consists of the 2:1 mix of histone H2A/H2B dimer and histone H3.1/H4 tetramer, are mixed with purified 5S rDNA (208 bp; N1202S, NEB), Neo (512 bp, amplified from pST18-Neo; 1175025, ROCHE), Myh6 core promoter (596 bp, −426 to +170) and Mhrt core promoter (a3/a4, 596 bp, −2290 to −1775) DNA at 2 M NaCl. PCR primers to amplify Neo are CGATGCGCTGCGAATCGGGA (SEQ ID NO: 55) and CACTGAAGCGGGAAGGGACT (SEQ ID NO: 56). The salt concentration is gradually lowered by dilution to allow the formation of nucleosomes. The EMSA assay is used to assess the efficiency of nucleosome assembly. For amylose pull-down assay, the amylose resin (E8021S, NEB) is washed thoroughly and equilibrated with binding buffer (10 mM Tris-HCl, pH 7.5, 150 mM NaCl) before incubation with purified MBP or MBP-D1D2 proteins for 2 h. Nucleosome mixture or naked DNA mixture of 5S rDNA, Neo and Myh6 promoter DNA are added for incubation at 4° C. for over-night. The resin is then washed excessively by washing buffer (20 mM Tris-HCl, pH 8.1, 150 mM NaCl, 2 mM EDTA, 1% Triton X-100, 0.1% SDS) before decross-linking and extraction of the DNA with phenol:chloroform:isoamyl alcohol. For competition assays, in vitro transcribed Mhrt779 is incubated with MBP-D1D2 in binding buffer (10 mM HEPES-KOH, pH 7.3, 10 mM NaCl, 1 mM MgCl2, 1 mM DTT) with ribonuclease inhibitor at room temperature for 30 min before adding nucleosomal DNA. The subsequent incubation, wash and DNA purification are performed as regular amylose pull-down assays. The qPCR signal of individual pull-down reaction is standardized to its own input RT-qPCR signal. qPCR primers are designed to amplify the 5S rDNA (CAAGCAAGAGCCTACGACCA (SEQ ID NO: 57); ATTC GTTGGAATTCCTCGGG (SEQ ID NO: 58), Neo (TAAAGCACGAGGAAGCGGTC (SEQ ID NO: 59)); TCGACCCCAAGCGAAACAT (SEQ ID NO: 60), Myh6 promoter (GCAGATAGCCAGGGTTGAAA (SEQ ID NO: 61)); TGGGTAAGGGTCACCTTCTC (SEQ ID NO: 62)) and Mhrt promoter (ATGCCAAATGGTTGCTCTTT (SEQ ID NO: 63); GAGCTTGAGAACCAGGCAGT (SEQ ID NO: 64)).

Cloning of Brg1 Truncation Constructs

For cloning of truncated Brg1 with deletion of amino acids 774-913 (ΔD1) or 108621246 (ΔD2), primers with an NheI restriction digestion site, which complement the downstream and upstream sequences of the truncated region (ΔD1: CCCGGGGCTAGCCTGCAGAACAAGCTACCGGAGCT (SEQ ID NO: 65) and CCCGGGGCTAGCCAGGTTGTTGTTGTACAGGGACA (SEQ ID NO: 66); ΔD2: CCCGGGGCTAGCATCAAGAAGTTCAAATTTCCC (SEQ ID NO: 67) and CCCGGGGCTAGCCTGCAGGCCATCCTGGAGCACGAGCAG (SEQ ID NO: 68)) are used to amplify from pActin-Brg1-IRES-eGFP by KOD XTREME Hot Start DNA Polymerase (NOVAGEN). After digestion with NheI, the linearized fragment is subject to ligation and transformation. The truncation constructs are sequenced to confirm the fidelity of the cloning. Western blot is further performed to assess the expression of the constructs. Monoclonal H-10 antibodies (SANTA CRUZ BIOTECH, sc-374197), which are raised against Brg1 N-terminal amino acids, are used in the experiments involving truncated Brg1.

Protein Sequence Analysis

Brg1 core helicase domain (774-1202) is applied for secondary structure prediction using the Fold & Function Assignment System (FFAS) server (<http://ffas.burnham.org/ffas-cgi/cgi/ffas.pl>). The output revealed that Brg1 core helicase domains are structural homologues of SF2 helicases: Vasa[78] (fruit fly, Protein Data Bank (PDB) accession number 2DB3), Rad54[63,79] (zebrafish PDB accession 1Z3I, *Sulfolobus solfataricus* PDB accession 1Z63) and Chd1[80] (yeast, PDB accession 3MWY). Those proteins, together with Brg1, are further employed for multiple sequence alignment with T-Coffee, which is a program allowing combination of the results obtained with several alignment methods (<http://www.ebi.ac.uk/Tools/msa/tcoffee/>).

RNA Secondary Structural Prediction

To predict the secondary structure for mouse Mhrt and human MHRT, the single-stranded sequence of Mhrt779 and human MHRT are analyzed on the VIENNA RNAFOLD web server (<http://rna.tbi.univie.ac.at/cgi-bin/RNAfold.cgi>) with calculation of minimum free energy.[65,81,82,83]

Human Heart Tissue Analysis

Human tissues are processed for RT-qPCR and strand-specific RT-PCR. The use of human tissues is in compliance with the regulation of Sanford/Burnham Medical Research Institute, Intermountain Medical Center, Stanford University, and Indiana University.

Primary Cardiomyocyte Culture

For functional studies in cardiomyocytes, neonatal rat ventricular cardiomyocytes are cultured as previously described.[84,85] Briefly, P0 or P1 Sprague-Dawley rats are used. The ventricles are excised and trypsinized for 15 min 4-5 times. Cells are then collected and resuspended in DMEM supplements with 10% FBS. The cells are plated for 1 h to allow the attachment of noncardiomyocyte cells. The remaining cardiomyocytes are plated at a density of $2\times10^5$ cells $ml^{-1}$. The cells are transfected with LIPOFECTAMINE® 2000 (INVITROGEN) after 48 h.

Example 2

Growth of Brg1-Null Myocardium

This example is illustrated in FIGS. 103, 104, 105, 106, 107, 108, 109, 110, 111 and 112 and shows that Brg1 promotes myocardial proliferation. FIG. 103 and FIG. 104 illustrate haematoxylin and eosin sections of E10.5 compact myocardium, the thickness of which being denoted by arrowheads. FIG. 105 and FIG. 106 shows BrdU immunostaining of E10.5 compact myocardium. FIG. 107 shows BrdU incorporation quantification. Letter "A" in FIG. 107 refers to number of areas examined. FIGS. 108 and 109 show Bmp10 in situ hybridization of E10.5 hearts. FIGS. 110 and 111 show $p57^{kip2}$ immunostaining of E10.5 hearts. FIG. 112 shows p57kip2 quantification. FIGS. 103, 104, 105, 106, 107, 108, 109, 110 and 111 are cropped from ×200 magnification. P values are calculated using the Student's t-test. Error bars are data±1 standard deviation (s.d.).

In the example, a Sm22α-cre transgene[23] is used to remove floxed alleles of Brg1 $(Brg1^f)^{24}$ in the mouse myocardium (cardiomyocytes) by embryonic day (E)9.5. Sm22α-cre;Brg1$^{f/f}$ embryos are grossly normal at E11.5, but died thereafter. At E10.5 the heart has thin compact myocardium and fails to form an interventricular septum, although the trabeculation is normal.[23] At E11.5, the trabeculation, cardiac jelly and vasculature remain normal despite the thin myocardium and absent septum. Loss of compact myocardium can reduce cardiac output, causing embryonic lethality.

These embryos have almost no myocardial apoptosis. The compact and septal primordial myocardium shows a marked decrease in cell proliferation at E10.5, whereas other heart layers are normal. Therefore, Brg1 is required for cell proliferation to form the compact and septal myocardium.

To identify genes responsible for these defects, RNA in situ hybridization is used in the example to survey crucial myocardial transcripts in E10-E11 Sm22α-cre;Brg1$^{f/f}$ hearts, including Nkx2.5, Gata4, Mef2c, Tbx3, TbxS, Cx43 (also known as Gja1), Irx1, Irx2, Nppa and Bmp10. No changes in these transcripts is found except for Bmp10, a key factor required for myocardial proliferation.[25] Bmp10 expression is nearly abolished in the compact myocardium of E10.5 Sm22α-cre;Brg1$^{f/f}$ embryos (FIGS. 108 and 109). Next, $p57^{kip2}$, a cyclin-dependent kinase inhibitor, is examined. The expression of $p57^{kip2}$ is normally suppressed by Bmp10.[25] The $p57^{kip2}$ level correlates inversely with normal cardiac cell proliferation. Also, $p57^{kip2}$ appears ectopically in E10.5 Sm22α-cre;Brg1$^{f/f}$ myocardium (FIGS. 110, 111 and 112), correlating with Bmp10 reduction and termination of myocardial cell proliferation. The Bmp10/$p57^{kip2}$-mediated proliferation is confirmed when myocardial proliferation in Sm22α-cre;Brg1$^{f/f}$ is rescued with recombinant BMP10 by whole embryo cultures.[26]

The Mef2c-cre line[27] is further used to delete Brg1 in the right ventricular myocardium, leaving Brg1 intact in the endocardium and left ventricle. Mef2c-cre;Brg1$^{f/f}$ embryos have hypoplastic outflow tracts and right ventricles. The Brg1-null right ventricle phenocopies the defects in Sm22α-cre;Brg1$^{f/f}$ ventricles, namely Bmp10 downregulation, ectopic $p57^{kip2}$ expression and proliferation reduction, whereas the Brg1-positive left ventricle is normal, demonstrating a primary and myocardially specific regulation of Bmp10/$p57^{kip2}$ by Brg1.

Example 3

Differentiation of Brg1-Null Myocardium

This example is illustrated in FIGS. 113, 114, 115, 116, 117, 118, 119, 120, 121, 122, 123 and 124 and shows that Brg1 suppresses myocardial differentiation. FIGS. 113 and 114 show electron microscopy (cropped from ×35,000 magnification) of the compact myocardium of E10.5 embryos. FIG. 115 shows quantitative RT-PCR of ventricular α-MHC and β-MHC at E10.5 and E11.5. In FIG. 116, "Ctrl" refers to control; "Mut" refers to Sm22α-cre;Brg1$^{f/f}$. FIG. 116 illustrates sequence alignment of the α-MHC locus from mouse, human and rat. In FIG. 116, Peak heights indicate degree of sequence homology. Black boxes (a1-a7) are regions of high sequence homology and are further analyzed by ChIP. Red regions are promoter elements. Pink regions are introns. Yellow regions are untranslated regions. FIG. 117 shows PCR analyses of Brg1-immunoprecipitated chromatin from E11.5 hearts. In FIG. 117, "anti-HRP" refers to anti-horse radish peroxidase antibody. FIG. 118 shows luciferase reporter assay of the proximal α-MHC promoter (−462 to +192) in SW13 cells. "TSA" refers to trichostatin A. FIG. 119 shows sequence alignment of the β-MHC locus from mouse, human and rat. Black boxes (b1-b5) are regions of high sequence homology and these regions are further analyzed by ChIP. Green, transposons/simple repeats. FIG. 120 shows PCR analysis of Brg1-immunoprecipitated chromatin from E11.5 hearts. FIG. 121 illustrates Luciferase reporter assays of the β-MHC proximal promoter (−835 to +222) in SW13 cells. FIG. 122 illustrates immunostaining (cropped from ×200 magnification) of HDAC1, HDAC2, HDAC3, HDAC5, HDAC6 and HDAC9 (brown shown as dark regions in FIG. 122) in E11.5 hearts. FIG. 123 shows co-immunoprecipitation of Brg1 with HDAC1, HDAC2 and HDAC9 in E11.5 hearts. FIG. 124 shows quantitative RT-PCR of α- and β-MHC of cultured embryos treated with dimethylsulphoxide (DMSO) or TSA. P values are calculated using the Student's t-test. All error bars are data±1 s.d.

In the example, whether the early termination of proliferation in Sm22α-cre;Brg1$^{f/f}$ myocardium is coupled with premature differentiation is examined. The myofibril formation of E10.5 cardiomyocytes is analyzed by α-actinin immunostaining and electron microscopy. Although control compact myocardial cells shows diffuse distribution of α-actinin, a component of Z-lines that demarcate sarcomeres, those of Sm22α-cre;Brg1$^{f/f}$ begin to show striated patterns. Electron microscopy confirms that Sm22α-cre;Brg1$^{f/f}$ myocardium has consecutive sarcomeres whereas controls only has short myofibrils (FIGS. 113 and 114).

Quantitative PCR is then used with reverse transcription (RT-PCR) to measure mRNA expression of the two MHC isoforms, α-MHC, which is mainly expressed by adult hearts, and fi-MHC, which is expressed primarily by embryonic hearts. E10.5 and E11.5 Sm22α-cre;Brg1$^{f/f}$ ventricles highly expressed α-MHC and downregulated β-MHC, thereby increasing the α- to β-MHC ratio by 7-12-fold (FIG. 115). Together with myofibril analysis, these data indicate that Brg1-null myocardial cells are highly differentiated and thus support a role of Brg1 in maintaining myocardial cells in an embryonic state of differentiation.

To test if Brg1 directly regulates MHC expression, Brg1 binding to MHC promoters is examined. With sequence alignment (<http://www.dcode.org>), seven regions are identified (a1-a7) in the mouse intergenic ~4 kilobase (kb) α-MHC promoter[28] that are evolutionarily conserved in mouse, rat and human (FIG. 116). Chromatin immunoprecipitation (ChIP) assay using E11.5 hearts with J1 anti-Brg1 antibody[23] shows that of the seven regions, Brg1 is strongly associated with the proximal promoter (a1) of α-MHC (FIG. 117). In contrast with α-MHC, none of the four conserved regions in the 5 kb upstream promoter of Bmp10 is associated with Brg1. To test Brg1/BAF transcriptional activity, different regions of the α-MHC promoter are cloned into chromatinized episomal reporter pREP429, resulting in different constructs. The different constructs are then transfected into SW13 cells,[23] which lack Brg1 and Brm.[30] The result shows that restoring Brg1 expression causes an approximately 65-75% reduction in the α-MHC reporter activity, and the proximal promoter (a1) is critical for α-MHC repression (FIG. 118). These observations support a direct repression of α-MHC by Brg1.

Because HDACs are chromatin modifiers that mediate transcriptional repression,[15] Brg1 may require HDACs to repress α-MHC. Indeed, Brg1 fails to repress the α-MHC reporter in SW13 cells treated with trichostatin A, an HDAC inhibitor (FIG. 118). Neither can HDAC repress the α-MHC reporter without Brg1 (FIG. 118). HDAC proteins, including class I HDAC1, HDAC2 and HDAC3 and class II HDAC5, HDAC6 and HDAC9, are present in myocardial nuclei (FIGS. 119 and 122), and Brg1 co-immunoprecipitated with HDAC1, HDAC2, HDAC3 and HDAC9 in E11.5 ventricles (FIG. 123). These findings indicate that Brg1 and HDACs co-repress α-MHC in the embryonic myocardium.

The 5.5 kb β-MHC promoter is further analyzed,[28] where five highly conserved regions are identified (b1-b5 in FIG. 119). Brg1 is widely associated with four of the five regions by ChIP experiments (FIG. 120). Restoring Brg1 expression in SW13 cells activates β-MHC reporters (FIG. 121). Deletional analysis of the β-MHC promoter shows that the proximal promoter (b1) is necessary for the Brg1-mediated β-MHC activation (FIG. 121). This activation of β-MHC did not require HDAC activity (FIG. 121); however, HDAC is necessary for the basal activity of β-MHC, as HDAC inhibition resulted in a reduction of β-MHC promoter activity (FIG. 121).

Further, whether HDAC inhibition in embryos causes premature α/β-MHC switches, as observed in Brg1-null myocardium, is investigated. The example shows that trichostatin-A-treated cultured embryos significantly upregulates α-MHC, whereas β-MHC is downregulated (FIG. 120). Overall, the biochemical studies, reporter assays and embryo culture experiments indicate that Brg1 and HDACs co-repress α-MHC but independently activate β-MHC.

Although trichostatin A causes MHC switches in embryos, HDAC inhibition does not reduce myocardial proliferation. Conversely, BMP10 rescues myocardial proliferation in Sm22α-cre;Brg1$^{f/f}$ embryos, but does not influence α/β-MHC expression. Therefore, Brg1 governs two parallel pathways to independently control myocardial growth and differentiation in embryos.

Example 4

Cardiac Hypertrophy and MHC Changes in Adult Hearts

Figure 127:
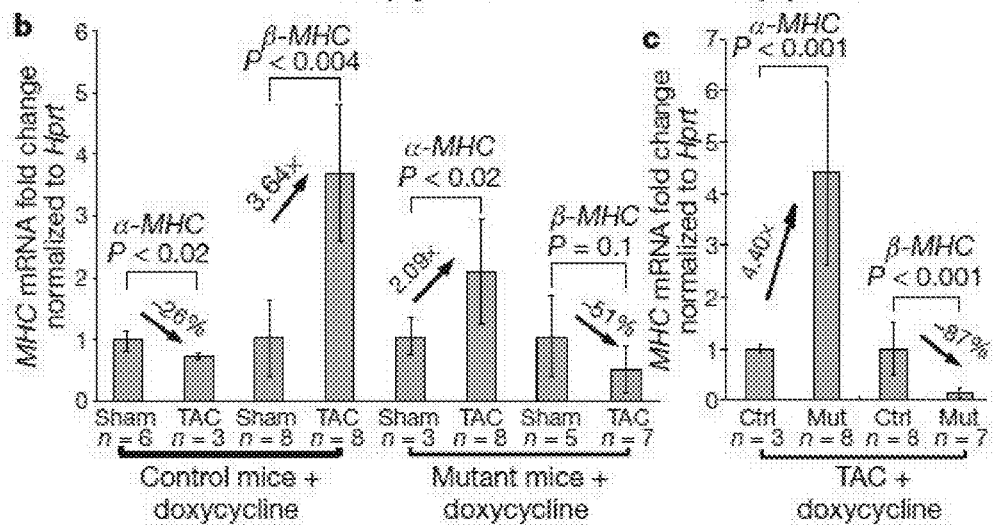

This example illustrates whether Brg1 is also critical for cardiac growth and differentiation in stressed adult hearts. FIGS. 125, 126 and 127 are a set of graphs showing that Brg1 is required for cardiac hypertrophy. FIG. 125 shows cardiomyocyte size quantification. "Ctrl" refers to control. "Mut" refers to Tnnt2-rtTA;Tre-cre;Brg1f/f. FIG. 126 and FIG. 127 show quantitative RT-PCR of α- and β-MHC in cardiac ventricles of doxycycline-treated control and Tnnt2-rtTA;Tre-cre;Brg1$^{f/f}$ mice 4 weeks after sham/TAC operation. P values are calculated using the Student's t-test. All error bars are data±1 s.d.

In this example, to bypass embryonic lethality, the doxycycline-inducible Tnnt2-rtTA;Tre-cre mouse line[31] is used to effect adult myocardial gene deletion. A 5-day doxycycline treatment is sufficient to activate a β-galactosidase reporter. The transverse aorta is surgically constricted (transverse aortic constriction (TAC)) to pressure-overload the heart and cardiac hypertrophy in control and Tnnt2-rtTA; Tre-cre;Brg1$^{f/f}$ littermates is induced. The transgene and doxycycline alone does not cause hypertrophy (FIG. 125).

Four weeks after surgery, the control and Tnnt2-rtta;Tre-cre; Brg1$^{f/f}$ mice on a normal diet develop severe cardiac hypertrophy with increased cardiomyocyte size (FIG. 125), ventricle: body-weight ratio, and cardiac fibrosis. In contrast, doxycycline-treated Tnnt2-rtTA;Tre-cre;Brg1$^{f/f}$ mice have only mild cardiac hypertrophy with a slight increase in cardiomyocyte size (FIG. 125) and ventricle: body-weight ratio, and without fibrosis. Overall, Brg1-null myocardium has a 63-73% reduction of cardiac hypertrophy. Thus, Brg1 is essential for the pressure-induced cardiac hypertrophy.

Whether Brg1 regulates MHC expression in hypertrophic hearts is next investigated. Control hypertrophic hearts undergo canonical MHC changes, namely α-MHC downregulation β-MHC upregulation (FIG. 126). In contrast, doxycycline-treated Tnnt2-rtTA;Tre-cre;Brg1$^{f/f}$ mice shows a 2.1-fold increase in α-MHC and a 51% reduction in β-MHC (FIG. 126). Consequently, the pressure-stressed Brg1-null myocardium shows a 4.4-fold increase in α-MHC expression and an 87% decrease in β-MHC expression compared with the control myocardium (FIG. 127). This reversal of MHC is not caused by reduced hypertrophy, which can only lessen but not reverse canonical MHC changes. Therefore, Brg1 is critical for the α/β-MHC switch in hypertrophic hearts.

FIGS. 128, 129, 130, 131, 132, 133, 134, 135, 136, 137, 138, 139 and 140 are a set of images and graphs showing MHC regulation by Brg1, PARP and HDAC. FIGS. 128, 129 and 130 illustrate Brg1 immunostaining (cropped from ×200 magnification) in ventricular myocardium of doxycycline-treated control and Tnnt2-rtTA;Tre-cre;Brg1$^{f/f}$ mice 1 week after sham/TAC operation. Arrows in FIGS. 128, 129 and 130 indicate cardiomyocyte nuclei. FIG. 131 is an image of Brg1 immunoblot of cardiac nuclear extracts from wild-type mice 2 weeks after TAC. FIG. 132 is a graph of quantitative RT-PCR of Brg1 mRNA in wild-type mice 2 weeks after TAC. FIG. 133 is an image of PCR of Brg1- and PARP1-immunoprecipitated chromatin from thymus and adult hearts 2 weeks after TAC. FIG. 134 is a graph of luciferase reporter assays of α-MHC promoter in SW13 cells with PARP inhibition. FIG. 135 is a graph of luciferase reporter assays of β-MHC promoter in SW13 cells with PARP inhibition. FIG. 136 and FIG. 137 are images of co-immunoprecipitation of Brg1, PARP1, HDAC2 and HDAC9 in TAC-treated adult hearts (FIG. 136) and in E11.5 hearts (FIG. 137). FIG. 138 is a graph of quantitative RT-PCR of α- and β-MHC of PJ-34-treated cultured embryos. FIG. 139 is an image of PCR of PARP1-immunoprecipitated chromatin from E11.5 hearts. FIG. 140 is an image of PCR of HDAC2-immunoprecipitated chromatin from adult hearts 2 weeks after TAC. P values are calculated using the Student's t-test. All error bars are data±1 s.d.

Although Brg1 is highly expressed in embryonic hearts, it is turned off in adult myocardium with some expression in endothelial or interstitial cells (FIG. 128). Brg1 becomes detectable in cardiomyocytes within 7 days after TAC by immunostaining (FIG. 129) con-firmed by western blot (FIG. 131), although it remains absent in Tnnt2-rtTA;Tre-cre;Brg1$^{f/f}$ myocardium (FIG. 130). Also, Brg1 mRNA increases by 1.8 fold within 2 weeks after TAC (FIG. 132), indicating that Brg1 reactivation by stress signals is essential for the hypertrophic process.

In the example, whether reactivated Brg1 controls MHC expression through the direct binding of MHC promoters is determined. ChIP analysis of TAC-treated hearts shows that Brg1 is highly enriched in the proximal promoters of both α-MHC and β-MHC, but not Bmp10 (FIG. 133). Furthermore, Brg1 binding to MHC promoters is detectable only in TAC-treated, but not sham-operated, hearts, consistent with Brg1 reactivation by pressure overload. The binding pattern is similar to that in embryonic hearts (FIGS. 117 and 120), indicating a common mechanism underlying the Brg1-mediated MHC control in embryonic and hypertrophic hearts.

Example 5

MHC Regulation by Brg1, HDAC and PARP

This example further illustrates that Brg1, HDAC and PARP regulate MHC.

Besides HDACs,[18,19,20] PARP1 is the only other chromatin-modifying enzyme[16] known to regulate cardiac hypertrophy.[17,22] However, it is unknown whether PARP1 binds to MHC promoters. ChIP analysis of TAC-treated hearts shows that PARP1 binds to the proximal promoters of α-MHC and β-MHC, but not Bmp10, a pattern similar to that of Brg1 (FIG. 133). Like Brg1, PARP1 binding occurs only in TAC-treated, but not sham-operated, hearts (data not shown). Furthermore, inhibiting PARP1 activity using PJ-34[32] reduces both Brg1-mediated α-MHC repression and fi-MHC activation in reporter assays in SW13 cells, indicating that Brg1 and PARP1 cooperate to regulate MHC (FIG. 134 and FIG. 124). Indeed, PARP1 and Brg1 co-immunoprecipitate in both TAC-treated hearts and E11.5 hearts (FIG. 136 and FIG. 137). Embryos cultured with PJ-34 have normal myocardial proliferation, but show α/β-MHCs switches characteristic of Brg1-null myocardium (FIG. 138). Immunostaining and ChIP analyses of E11.5 hearts show that PARP1 is present in myocardial nuclei and bound to the proximal promoters of α- and β-MHC but not Bmp10, a pattern similar to that of Brg1 (FIG. 139). These findings indicate that Brg1 complexes with PARP1 to regulate MHC in embryonic and stressed adult hearts.

Brg1 and PARP1 co-immunoprecipitated with HDAC1, HDAC2 or HDAC9 in E11.5 and stressed adult hearts (FIGS. 123, 136 and 137). Whether HDACs are present on MHC promoters is examined Using ChIP with two cross-linking steps[33] in TAC treated hearts, it is found that HDAC2 and HDAC9 are enriched in the α-MHC promoter but bound modestly to the β-MHC promoter (FIG. 140, described below), suggesting direct α-MHC and indirect β-MHC regulation by HDACs. Together with reporter assays (FIGS. 118, 121, 134 and 135), these biochemical studies indicate that Brg1, PARP and HDAC physically form a chromatin-remodeling complex on the α-MHC promoter to repress α-MHC, whereas Brg1 complexes with PARP on the β-MHC promoter to activate β-MHC.

Example 6

Implication for Human Cardiomyopathy

This example is illustrated in FIGS. 1, 141, 142 and 143 and implicates BRG1 activation in human cardiomyopathy. FIG. 141 is a set of graphs showing quantitative RT-PCR of α-MHC, β-MHC and BRG1 expression in normal and hypertrophic cardiomyopathy subjects (HCM). P values are calculated using the Student's t-test. Error bars are data±1 s.d. FIG. 142 is a graph of IVSd (y) plotted against the BRG1 RNA level (x). Regression curve 14210 is illustrated in FIG. 141. The letter "e" in the equation in FIG. 142 represents the base of the natural logarithm (~2.718). The arrow and dashed line refer to the inflection point. FIG. 143 is a graph of the β/α-MHC RNA ratio (y) plotted against the BRG1 RNA level (x). FIG. 1 is a model of developmentally activated and stress-induced assembly of BAF/HDAC/PARP complexes on the α-MHC promoter, and BAF/PARP complex on the β-MHC promoter.

To investigate if BRG1 is activated in human hypertrophic hearts, patients with hypertrophic cardiomyopathy of unknown aetiology are studied. These patients require surgical myectomy[34] to relieve cardiac obstruction caused by prominent ventricular or septal hypertrophy. The severity of hypertrophic cardiomyopathy is measured by the maximal thickness of the interventricular septum during diastole (IVSd). IVSd in hypertrophic cardiomyopathy patients is 2.02-fold that of the control group. Quantitative RT-PCR analyses show that hearts with hypertrophic cardiomyopathy have a 48-fold reduction of α-MHC, a 5.5-fold increase of β-MHC and a twofold increase of BRG1 expression (FIG. 141). The loss of α-MHC, gain of β-MHC and activation of BRG1 resemble the changes observed in mice with hypertrophy, indicating that BRG1 has a similar role in human disease. Consistent with this notion, the IVSd and β-MHC: α-MHC ratio correlate well with the BRG1 level in control and hypertrophic cardiomyopathy subjects, with sigmoidal regression curves inflecting at 1.50-fold and 1.45-fold of BRG1, respectively (FIGS. 142 and 143). At the inflection point of 1.50-fold BRG1, IVSd equals 1.54 cm, coinciding with a clinical criterion (IVSd>1.50 cm) in the diagnosis of hypertrophic cardiomyopathy.[35] Therefor, a 50% increase in BRG1 may be a threshold for disease development in certain patients.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

REFERENCES

The following references are referred to above and are incorporated herein by reference:
1. van Rooij, E. et al. Control of stress-dependent cardiac growth and gene expression by a microRNA. Science 316, 575-579 (2007).
2. Herron, T. J. & McDonald, K. S. Small amounts of α-myosin heavy chain isoform expression significantly increase power output of rat cardiac myocyte fragments. Circ. Res. 90, 1150-1152 (2002).
3. Krenz, M. & Robbins, J Impact of b-myosin heavy chain expression on cardiac function during stress. J. Am. Coll. Cardiol. 44, 2390-2397 (2004).
4. James, J. et al. Forced expression of α-myosin heavy chain in the rabbit ventricle results in cardioprotection under cardiomyopathic conditions. Circulation 111, 2339-2346 (2005).
5. Miyata, S., Minobe, W., Bristow, M. R. & Leinwand, L. A. Myosin heavy chain isoform expression in the failing and nonfailing human heart. Circ. Res. 86, 386-390 (2000).
6. Abraham, W. T. et al. Coordinate changes in myosin heavy chain isoform gene expression are selectively associated with alterations in dilated cardiomyopathy phenotype. Mol. Med. 8, 750-760 (2002).
7. Lowes, B. D. et al. Myocardial gene expression in dilated cardiomyopathy treated with b-blocking agents. N. Engl. J. Med. 346, 1357-1365 (2002).

8. Blaxall, B. C., Tschannen-Moran, B. M., Milano, C. A. & Koch, W. J. Differential gene expression and genomic patient stratification following left ventricular assist device support. J. Am. Coll. Cardiol. 41, 1096-1106 (2003).
9. Geisterfer-Lowrance, A. A. et al. A mouse model of familial hypertrophic cardiomyopathy. Science 272, 731-734 (1996).
10. Schmitt, J. P. et al. Cardiac myosin missense mutations cause dilated cardiomyopathy in mouse models and depress molecular motor function. Proc. Natl Acad. Sci. USA 103, 14525-14530 (2006).
11. Lowes, B. D. et al. Changes in gene expression in the intact human heart. Downregulation of α-myosin heavy chain in hypertrophied, failing ventricular myocardium. J. Clin. Invest. 100, 2315-2324 (1997).
12. McKinsey, T. A. & Olson, E. N. Toward transcriptional therapies for the failing heart: chemical screens to modulate genes. J. Clin. Invest. 115, 538-546 (2005).
13. Ho, L. & Crabtree, G. R. Chromatin remodelling during development. Nature 463, 474-484 (2010).
14. Bultman, S. et al. A Brg1 null mutation in the mouse reveals functional differences among mammalian SWI/SNF complexes. Mol. Cell 6, 1287-1295 (2000).
15. Backs, J. & Olson, E. N. Control of cardiac growth by histone acetylation/deacetylation. Circ. Res. 98, 15-24 (2006).
16. Schreiber, V., Dantzer, F., Ame, J. C. & de Murcia, G. Poly(ADP-ribose): novel functions for an old molecule. Nature Rev. Mol. Cell Biol. 7, 517-528 (2006).
17. Bartha, E. et al. PARP inhibition delays transition of hypertensive cardiopathy to heart failure in spontaneously hypertensive rats. Cardiovasc. Res. 83, 501-510 (2009).
18. Kong, Y. et al. Suppression of class I and II histone deacetylases blunts pressure-overload cardiac hypertrophy. Circulation 113, 2579-2588 (2006).
19. Antos, C. L. et al. Dose-dependent blockade to cardiomyocyte hypertrophy by histone deacetylase inhibitors. J. Biol. Chem. 278, 28930-28937 (2003).
20. Trivedi, C. M. et al. Hdac2 regulates the cardiac hypertrophic response by modulating Gsk3 beta activity. Nature Med. 13, 324-331 (2007).
21. Kee, H. J. et al Inhibition of histone deacetylation blocks cardiac hypertrophy induced by angiotensin II infusion and aortic banding. Circulation 113, 51-59 (2006).
22. Pillai, J. B. et al. Poly(ADP-ribose) polymerase-1-deficient mice are protected from angiotensin II-induced cardiac hypertrophy. Am. J. Physiol. Heart Circ. Physiol. 291, H1545-H1553 (2006).
23. Stankunas, K. et al. Endocardial Brg1 represses ADAMTS1 to maintain the microenvironment for myocardial morphogenesis. Dev. Cell 14, 298-311 (2008).
24. Sumi-Ichinose, C., Ichinose, H., Metzger, D. & Chambon, P. SNF2b-BRG1 is essential for the viability of F9 murine embryonal carcinoma cells. Mol. Cell. Biol. 17, 5976-5986 (1997).
25. Chen, H. et al. BMP10 is essential for maintaining cardiac growth during murine cardiogenesis. Development 131, 2219-2231 (2004).
26. Chang, C. P. et al. A field of myocardial-endocardial NFAT signaling underlies heart valve morphogenesis. Cell 118, 649-663 (2004).
27. Verzi, M. P., McCulley, D. J., De Val, S., Dodou, E. & Black, B. L. The right ventricle, outflow tract, and ventricular septum comprise a restricted expression domain within the secondary/anterior heart field. Dev. Biol. 287, 134-145 (2005).
28. Pandya, K. et al. Discordant on/off switching of gene expression in myocytes during cardiac hypertrophy in vivo. Proc. Natl Acad. Sci. USA 105, 13063-13068 (2008).
29. Liu, R. et al. Regulation of CSF1 promoter by the SWI/SNF-like BAF complex. Cell 106, 309-318 (2001).
30. Muchardt, C. & Yaniv, M. A human homologue of *Saccharomyces cerevisiae* SNF2/SWI2 and *Drosophila* brm genes potentiates transcriptional activation by the glucocorticoid receptor. EMBO J. 12, 4279-4290 (1993).
31. Wu, B. et al. Inducible cardiomyocyte-specific gene disruption directed by the rat Tnnt2 promoter in the mouse. Genesis 48, 63-72 (2009).
32. Szabo, G. et al. Poly(ADP-Ribose) polymerase inhibition reduces reperfusion injury after heart transplantation. Circ. Res. 90, 100-106 (2002).
33. Wang, Z. et al. Genome-wide mapping of HATs and HDACs reveals distinct functions in active and inactive genes. Cell 138, 1019-1031 (2009).
34. Morrow, A. G. & Brockenbrough, E. C. Surgical treatment of idiopathic hypertrophic subaortic stenosis: technic and hemodynamic results of subaortic ventriculomyotomy. Ann Surg. 154, 181-189 (1961).
35. Braunwald, E. Heart Disease: A Textbook of Cardiovascular Medicine (W.B. Saunders Company, 1997).
36. Kinugawa, K. et al. Regulation of thyroid hormone receptor isoforms in physiological and pathological cardiac hypertrophy. Circ. Res. 89, 591-598 (2001).
37. Molkentin, J. D. et al. A calcineurin-dependent transcriptional pathway for cardiac hypertrophy. Cell 93, 215-228 (1998).
38. Boucher, P., Gotthardt, M., Li, W. P., Anderson, R. G. & Herz, J. LRP: role in vascular wall integrity and protection from atherosclerosis. Science 300, 329-332 (2003).
39. RIKEN Genome Exploration Research Group and Genome Science Group (Genome Network Project Core Group) and the FANTOM Consortium. Antisense transcription in the mammalian transcriptome. Science 309, 1564-1566 (2005).
40. Haddad, F., Bodell, P. W., Qin, A. X., Giger, J. M. & Baldwin, K. M. Role of antisense RNA in coordinating cardiac myosin heavy chain gene switching. J. Biol. Chem. 278, 37132-37138 (2003).
41. Hang, C. T. et al. Chromatin regulation by Brg1 underlies heart muscle development and disease. Nature 466, 62-67 (2010).
42. Hung, T. et al. Extensive and coordinated transcription of noncoding RNAs within cell-cycle promoters. Nature Genet. 43, 621-629 (2011).
43. Lin, M. F., Jungreis, I. & Kellis, M. PhyloCSF: a comparative genomics method to distinguish protein coding and non-coding regions. Bioinformatics 27, i275-i282 (2011).
44. Ingolia, N. T., Brar, G. A., Rouskin, S., McGeachy, A. M. & Weissman, J. S. The ribosome profiling strategy for monitoring translation in vivo by deep sequencing of ribosome-protected mRNA fragments. Nature Protocols 7, 1534-1550 (2012).
45. Lompre, A. M. et al. Myosin isoenzyme redistribution in chronic heart overload. Nature 282, 105-107 (1979).
46. Schultz, J. J. et al. TGF-b1 mediates the hypertrophic cardiomyocyte growth induced by angiotensin II. J. Clin. Invest. 109, 787-796 (2002).
47. Molkentin, J. D. & Dorn, G. W. II. Cytoplasmic signaling pathways that regulate cardiac hypertrophy. Annu. Rev. Physiol. 63, 391-426 (2001).

48. López, B. et al. Osteopontin-mediated myocardial fibrosis in heart failure: a role for lysyl oxidase? Cardiovasc. Res. 99, 111-120 (2013).
49. Frey, N. & Olson, E. N. Cardiac hypertrophy: the good, the bad, and the ugly. Annu. Rev. Physiol. 65, 45-79 (2003).
50. Guttman, M. et al. Chromatin signature reveals over a thousand highly conserved large non-coding RNAs in mammals. Nature 458, 223-227 (2009).
51. Rando, O. J. & Chang, H. Y. Genome-wide views of chromatin structure. Annu. Rev. Biochem. 78, 245-271 (2009).
52. Hahn, M. A., Wu, X., Li, A. X., Hahn, T. & Pfeifer, G. P. Relationship between gene body DNA methylation and intragenic H3K9me3 and H3K36me3 chromatin marks. PLoS ONE 6, e18844 (2011).
53. Mikkelsen, T. S. et al. Genome-wide maps of chromatin state in pluripotent and lineage-committed cells. Nature 448, 553-560 (2007).
54. Musselman, C. A. et al. Molecular basis for H3K36me3 recognition by the Tudor domain of PHF1. Nature Struct. Mol. Biol. 19, 1266-1272 (2012).
55. Liu, R. et al. Regulation of CSF1 promoter by the SWI/SNF-like BAF complex. Cell 106, 309-318 (2001).
56. Muchardt, C. & Yaniv, M. A human homologue of Saccharomyces cerevisiae SNF2/SWI2 and Drosophila brm genes potentiates transcriptional activation by the glucocorticoid receptor. EMBO J. 12, 4279-4290 (1993).
57. Szabó, G. et al. Poly(ADP-ribose) polymerase inhibition reduces reperfusion injury after heart transplantation. Circ. Res. 90, 100-106 (2002).
58. Hesselberth, J. R. et al. Global mapping of protein-DNA interactions in vivo by digital genomic footprinting. Nature Methods 6, 283-289 (2009).
59. Gupta, M. P. Factors controlling cardiac myosin-isoform shift during hypertrophy and heart failure. J. Mol. Cell. Cardiol. 43, 388-403 (2007).
60. Clapier, C. R. & Cairns, B. R. The biology of chromatin remodeling complexes. Annu. Rev. Biochem. 78, 273-304 (2009).
61. Jankowsky, E. & Fairman, M. E. RNA helicases—one fold for many functions. Curr. Opin. Struct. Biol. 17, 316-324 (2007).
62. Mallam, A. L., Del Campo, M., Gilman, B., Sidote, D. J. & Lambowitz, A. M. Structural basis for RNA-duplex recognition and unwinding by the DEAD-box helicase Mss116p. Nature 490, 121-125 (2012).
63. Dürr H., Korner, C., Muller, M., Hickmann, V. & Hopfner, K. P. X-ray structures of the Sulfolobus solfataricus SWI2/SNF2 ATPase core and its complex with DNA. Cell 121, 363-373 (2005).
64. Feng, Y. et al. Histone H4 acetylation differentially modulates arginine methylation by an in cis mechanism. J. Biol. Chem. 286, 20323-20334 (2011).
65. Zuker, M. On finding all suboptimal foldings of an RNA molecule. Science 244, 48-52 (1989).
66. Wu, B. et al. Inducible cardiomyocyte-specific gene disruption directed by the rat Tnnt2 promoter in the mouse. Genesis 48, 63-72 (2010).
67. Wei, K., Kuhnert, F. & Kuo, C. J. Recombinant adenovirus as a methodology for exploration of physiologic functions of growth factor pathways. J. Mol. Med. (Berl.) 86, 161-169 (2008).
68. Kuhnert, F. et al. Essential regulation of CNS angiogenesis by the orphan G protein-coupled receptor GPR124. Science 330, 985-989 (2010).
69. Xiong, Y. et al. Brg1 governs a positive feedback circuit in the hair follicle for tissue regeneration and repair. Dev. Cell 25, 169-181 (2013).
70. Langmead, B. & Salzberg, S. L. Fast gapped-read alignment with Bowtie 2. Nature Methods 9, 357-359 (2012).
71. Li, H. et al. The Sequence Alignment/Map format and SAMtools. Bioinformatics 25, 2078-2079 (2009).
72. Quinlan, A. R. & Hall, I. M. BEDTools: a flexible suite of utilities for comparing genomic features. Bioinformatics 26, 841-842 (2010).
73. Trapnell, C. et al. Differential gene and transcript expression analysis of RNA-seq experiments with TopHat and Cufflinks. Nature Protocols 7, 562-578 (2012).
74. Khavari, P. A., Peterson, C. L., Tamkun, J. W., Mendel, D. B. & Crabtree, G. R. BRG1 contains a conserved domain of the SWI2/SNF2 family necessary for normal mitotic growth and transcription. Nature 366, 170-174 (1993).
75. Grote, P. et al. The tissue-specific lncRNA Fendrr is an essential regulator of heart and body wall development in the mouse. Dev. Cell 24, 206-214 (2013).
76. Klattenhoff, C. A. et al. Braveheart, a long noncoding RNA required for cardiovascular lineage commitment. Cell 152, 570-583 (2013).
77. van der Vlag, J., den Blaauwen, J. L., Sewalt, R. G., van Driel, R. & Otte, A. P. Transcriptional repression mediated by polycomb group proteins and other chromatin-associated repressors is selectively blocked by insulators. J. Biol. Chem. 275, 697-704 (2000).
78. Sengoku, T., Nureki, O., Nakamura, A., Kobayashi, S. & Yokoyama, S. Structural basis for RNA unwinding by the DEAD-box protein Drosophila Vasa. Cell 125, 287-300 (2006).
79. Thomä, N. H. et al. Structure of the SWI2/SNF2 chromatin-remodeling domain of eukaryotic Rad54. Nature Struct. Mol. Biol. 12, 350-356 (2005).
80. Hauk, G., McKnight, J. N., Nodelman, I. M. & Bowman, G. D. The chromodomains of the Chd1 chromatin remodeler regulate DNA access to the ATPase motor. Mol. Cell 39, 711-723 (2010).
81. Zuker, M. & Stiegler, P. Optimal computer folding of large RNA sequences using thermodynamics and auxiliary information. Nucleic Acids Res. 9, 133-148 (1981).
82. Gruber, A. R., Lorenz, R., Bernhart, S. H., Neubock, R. & Hofacker, I. L. The Vienna RNA websuite. Nucleic Acids Res. 36, W70-W74 (2008).
83. Wan, Y., Kertesz, M., Spitale, R. C., Segal, E. & Chang, H. Y. Understanding the transcriptome through RNA structure. Nature Rev. Genet. 12, 641-655 (2011).
84. Fu, X. M., Yao, Y. J., Yang, Z., Xiang, L. & Gao, J. [Alteration and its significance to expression of aquaporin-4 in cultured neonatal rat astrocytes in the model of hypoxic damage.] Sichuan Da Xue Xue Bao Yi Xue Ban 36, 641-644 (2005).
85. Yang, J. et al. C-reactive protein augments hypoxia-induced apoptosis through mitochondrion-dependent pathway in cardiac myocytes. Mol. Cell. Biochem. 310, 215-226 (2008).

It is intended that the invention not be limited to the particular embodiment disclosed herein contemplated for carrying out this invention, but that the invention will include all embodiments falling within the scope of the claims.

All documents, patents, journal articles and other materials cited in the present application are incorporated herein by reference. While the present invention has been disclosed with references to certain embodiments, numerous modification, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A composition comprising a nucleic acid encoding a modified myosin heavy-chain-associated RNA transcript, wherein the modified myosin heavy-chain-associated RNA transcript inhibits Brg1's genomic targeting and gene regulation function in a subject to whom the composition is administered,
    wherein the modified myosin heavy-chain-associated RNA transcript comprises SEQ ID NO: 2.

2. A composition comprising a nucleic acid encoding a modified myosin heavy-chain-associated RNA transcript, wherein the modified myosin heavy-chain-associated RNA transcript inhibits Brg1's genomic targeting and gene regulation function in a subject to whom the composition is administered,
    wherein the modified myosin heavy-chain-associated RNA transcript comprises SEQ ID NO: 4.

3. The composition of claim 1, wherein the nucleic acid is incorporated into a vector.

4. The composition of claim 3, wherein the vector comprises an expression cassette comprising a promoter operably linked to the nucleic acid encoding the modified myosin heavy-chain-associated RNA transcript, and wherein the promoter directs an expression of the nucleic acid to produce the modified myosin heavy-chain-associated RNA transcript.

5. The composition of claim 4, wherein the promoter comprises an inducible promoter.

6. The composition of claim 5, wherein the promoter comprises a tetracycline response element.

7. A non-human organism carrying a transgene comprising a promoter and a nucleic acid encoding a modified myosin heavy-chain-associated RNA transcript,
wherein the promoter regulates an expression of the nucleic acid to produce the modified myosin heavy-chain-associated RNA transcript in the organism, and
wherein the modified myosin heavy-chain-associated RNA transcript inhibits Brg1's genomic targeting and gene regulation function in the organism; and
wherein the modified myosin heavy-chain-associated RNA transcript is selected from the group consisting of: SEQ ID NO: 2 and SEQ ID NO: 4.

8. The non-human organism of claim 7, wherein the transgene is incorporated into a genome DNA of the organism.

9. The non-human organism of claim 7, wherein the promoter comprises an inducible promoter.

10. The non-human organism of claim 9, wherein the promoter comprises a tetracycline response element.

11. The non-human organism of claim 8, wherein the organism is a transgenic mouse carrying the transgene.

12. The non-human organism of claim 11, wherein the promoter comprises a tetracycline response element, and wherein the nucleic acid encoding the modified myosin heavy-chain-associated RNA transcript expresses the modified myosin heavy-chain-associated RNA transcript in cardiomyocytes of the transgenic mouse in the presence of tetracycline or a tetracycline analog.

13. A method comprising:
administering to a subject a composition comprising a nucleic acid encoding a modified myosin heavy-chain-associated RNA transcript to express the modified myosin heavy-chain-associated RNA transcript in the subject,
wherein the modified myosin heavy-chain-associated RNA transcript inhibits Brg1's genomic targeting and gene regulation function in the subject; and
wherein the modified myosin heavy-chain-associated RNA transcript is selected from the group consisting of: SEQ ID NO: 2 and SEQ ID NO: 4.

14. The method of claim 13, wherein the composition comprises a vector, and wherein the nucleic acid encoding the modified myosin heavy-chain-associated RNA transcript is incorporated in the vector.

15. The method of claim 14, wherein the vector comprises an expression cassette comprising a promoter operably linked to the nucleic acid encoding the modified myosin heavy-chain-associated RNA transcript, and wherein the promoter regulates an expression of the nucleic acid to produce the modified myosin heavy-chain-associated RNA transcript in the subject.

16. The method of claim 13, wherein the nucleic acid is incorporated into a genome DNA of the subject.

17. The method of claim 15, wherein the promoter comprises an inducible promoter.

18. The method of claim 17, wherein the promoter comprises a tetracycline response element.

19. The method of claim 17, wherein the nucleic acid expresses the modified myosin heavy-chain-associated RNA transcript in cardiomyocytes of the subject under an induction of doxycycline treatment.

20. The method of claim 15, wherein the composition is administered to the subject with a pharmaceutical carrier.

21. The method of claim 15, wherein the composition is administered to the subject via injection.

22. The method of claim 21, wherein the composition is administered to the subject through intravenously injection.

23. The method of claim 21, wherein the composition is administered to the subject through intracardiac injection.

24. A treatment delivery apparatus comprising a device and at least one dosage of a composition contained in the device,
wherein the composition comprises a nucleic acid encoding a modified myosin heavy-chain-associated RNA transcript,
wherein the modified myosin heavy-chain-associated RNA transcript inhibits Brg1's genomic targeting and gene regulation function in a subject to whom the composition is administered; and
wherein the modified myosin heavy-chain-associated RNA transcript is selected from the group consisting of: SEQ ID NO: 2 and SEQ ID NO: 4.

25. The treatment delivery apparatus of claim 24, wherein the composition comprises a vector, and wherein the nucleic acid encoding the modified myosin heavy-chain-associated RNA transcript is incorporated in the vector.

26. The treatment delivery apparatus of claim 25, wherein the vector comprises an expression cassette comprising a promoter operably linked to the nucleic acid encoding the modified myosin heavy-chain-associated RNA transcript, and wherein the promoter directs an expression of the nucleic acid to produce the modified myosin heavy-chain-associated RNA transcript.

27. A method comprising:
administering to a subject a composition comprising a modified myosin heavy-chain-associated RNA transcript;
wherein the modified myosin heavy-chain-associated RNA transcript inhibits Brg1's genomic targeting and gene regulation function in the subject; and
wherein the modified myosin heavy-chain-associated RNA transcript is selected from the group consisting of: SEQ ID NO: 2 and SEQ ID NO: 4.

28. The method of claim 27, wherein the composition comprises nanoparticles, and wherein the modified myosin heavy-chain-associated RNA transcript is packaged with the nanoparticles.

29. The composition of claim 2, wherein the nucleic acid is incorporated into a vector.

30. The composition of claim 29, wherein the vector comprises an expression cassette comprising a promoter operably linked to the nucleic acid encoding the modified myosin heavy-chain-associated RNA transcript, and wherein the promoter directs an expression of the nucleic acid to produce the modified myosin heavy-chain-associated RNA transcript.

31. The composition of claim 30, wherein the promoter comprises an inducible promoter.

32. The composition of claim 31, wherein the promoter comprises a tetracycline response element.

* * * * *